US011406656B2

(12) United States Patent
Helenek et al.

(10) Patent No.: US 11,406,656 B2
(45) Date of Patent: *Aug. 9, 2022

(54) METHODS AND COMPOSITIONS FOR ADMINISTRATION OF IRON

(71) Applicant: American Regent, Inc., Shirley, NY (US)

(72) Inventors: Mary Jane Helenek, Brookville, NY (US); Marc L. Tokars, Douglassville, PA (US); Richard P. Lawrence, Calverton, NY (US)

(73) Assignee: American Regent, Inc., Shirley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,681

(22) Filed: Nov. 15, 2018

(65) Prior Publication Data

US 2019/0083524 A1 Mar. 21, 2019

Related U.S. Application Data

(60) Continuation of application No. 15/958,930, filed on Apr. 20, 2018, which is a division of application No. 14/683,415, filed on Apr. 10, 2015, now Pat. No. 10,213,455, which is a continuation of application No. 13/847,254, filed on Mar. 19, 2013, now abandoned, which is a continuation of application No. 12/787,283, filed on May 25, 2010, now Pat. No. 8,431,549, which is a continuation of application No. 11/620,986, filed on Jan. 8, 2007, now Pat. No. 7,754,702, application No. 16/192,681, which is a continuation of application No. 14/683,415, filed on Apr. 10, 2015, now Pat. No. 10,213,455, which is a continuation of application No. 13/847,254, filed on Mar. 19, 2013, now abandoned, which is a continuation of application No. 12/787,283, filed on May 25, 2010, now Pat. No. 8,431,549, which is a continuation of application No. 11/620,986, filed on Jan. 8, 2007, now Pat. No. 7,754,702.

(60) Provisional application No. 60/757,119, filed on Jan. 6, 2006.

(51) Int. Cl.
*A61K 31/7135* (2006.01)
*A61K 31/715* (2006.01)
*A61K 31/721* (2006.01)
*C07H 23/00* (2006.01)

(52) U.S. Cl.
CPC ........ *A61K 31/7135* (2013.01); *A61K 31/715* (2013.01); *A61K 31/721* (2013.01); *C07H 23/00* (2013.01)

(58) Field of Classification Search
CPC . A61K 31/7135; A61K 31/721; A61K 31/715
See application file for complete search history.

(56) References Cited

U.S. PATENT DOCUMENTS

| 1,199,951 A | 10/1916 | webster |
| 2,807,610 A | 9/1957 | Zief et al. ..................... 260/209 |
| 3,065,138 A | 11/1962 | Lynch et al. |
| 3,076,798 A | 2/1963 | Mueller, et al. |
| 3,100,202 A | 8/1963 | Muller et al. ................. 260/209 |
| 3,151,107 A | 9/1964 | Heckel et al. |
| 3,395,229 A | 7/1968 | Feigh et al. |
| 3,536,696 A | 10/1970 | Alsop et al. |
| 3,574,184 A | 4/1971 | Alsop et al. |
| 3,639,588 A | 2/1972 | Alsop et al. .................. 424/180 |
| 3,821,192 A | 6/1974 | Montgomery et al. |
| 3,886,267 A | 5/1975 | Dahlberg et al. |
| 3,928,581 A | 12/1975 | Dahlberg et al. |
| 3,965,133 A | 6/1976 | Dahlberg et al. |
| 3,969,395 A | 7/1976 | Dahlberg et al. |
| 4,056,672 A | 11/1977 | Dahlberg et al. |
| 4,180,567 A | 12/1979 | Herb |
| 4,189,474 A | 2/1980 | Kurosaki et al. |
| 4,335,116 A | 6/1982 | Howard |
| 4,370,476 A | 1/1983 | Usher et al. |
| 4,599,405 A | 7/1986 | Muller et al. ................. 536/113 |
| 4,612,284 A | 9/1986 | Pickens |
| 4,689,235 A | 8/1987 | Barnes |

(Continued)

FOREIGN PATENT DOCUMENTS

| CA | 623411 | 7/1961 |
| CA | 2195283 | 1/1997 |

(Continued)

OTHER PUBLICATIONS

Paul et al., Bioconjugate Chem., 2004, 15, p. 394-401. (Year: 2004).*
Boruch, M., Starch/Starke, 1985, 3, pp. 91-98. (Year: 1985).*
Letter/Written Disclosure of Information Disclosure Statement, filed herewith on Dec. 3, 2018, 2 pages.
Agarwal et al., "Oxidative stress and renal injury with intravenous iron in patients with chronic kidney disease," Kidney International 65:2279-2289 (2004).
Ahsan et al., "Efficacy of Bolus Intravenous Iron Dextran Treatment in Peritoneal Dialysis Patients Receiving Recombinant Human Erythropoietin," Advances in Peritoneal Dialysis (Khanna ed.) 12:161-166 (1996).

(Continued)

*Primary Examiner* — Jonathan S Lau
(74) *Attorney, Agent, or Firm* — Sorell, Lenna & Schmidt, LLP

(57) ABSTRACT

The present invention generally relates to treatment of iron-related conditions with iron carbohydrate complexes. One aspect of the invention is a method of treatment of iron-related conditions with a single unit dosage of at least about 0.6 grams of elemental iron via an iron carbohydrate complex. The method generally employs iron carbohydrate complexes with nearly neutral pH, physiological osmolarity, and stable and non-immunogenic carbohydrate components so as to rapidly administer high single unit doses of iron intravenously to patients in need thereof.

30 Claims, 2 Drawing Sheets

(56) References Cited

U.S. PATENT DOCUMENTS

| | | | |
|---|---|---|---|
| 5,102,652 A | 4/1992 | Groman et al. | |
| 5,160,726 A | 11/1992 | Josephson et al. | |
| 5,204,457 A | 4/1993 | Maruno et al. | |
| 5,541,158 A | 7/1996 | Vance et al. | 514/8 |
| 5,624,668 A | 4/1997 | Lawrence et al. | |
| 5,635,611 A | 6/1997 | Ishiguro et al. | |
| 5,756,715 A | 5/1998 | Monte et al. | |
| 6,010,719 A | 1/2000 | Remon | |
| 6,219,440 B1 | 9/2001 | Andreasen et al. | 514/59 |
| 6,495,177 B1 | 12/2002 | deVries | |
| 6,587,550 B2 | 7/2003 | Council et al. | |
| 6,599,498 B1 | 7/2003 | Groman et al. | 424/9.34 |
| 6,690,571 B2 | 2/2004 | Shindo et al. | |
| 6,960,571 B2 | 11/2005 | Helenek et al. | 514/53 |
| 6,977,249 B1 | 12/2005 | Andreasen et al. | 514/59 |
| 7,612,109 B2 | 11/2009 | Geisser et al. | 514/502 |
| 7,754,702 B2 | 7/2010 | Helenek et al. | 514/54 |
| 7,871,597 B2 | 1/2011 | Groman et al. | |
| 8,071,542 B2 | 12/2011 | Connor | |
| 8,263,577 B2 | 9/2012 | Reim et al. | |
| 8,431,549 B2 | 4/2013 | Helenek et al. | 514/58 |
| 8,496,994 B2 | 7/2013 | Levecke | |
| 8,722,101 B2 | 5/2014 | Tanner-Baumgartner et al. | |
| 8,778,878 B2 | 7/2014 | Connor | |
| 8,809,424 B2 | 8/2014 | Feron | |
| 8,815,301 B2 | 8/2014 | Andreasen | 424/647 |
| 8,895,612 B2 | 11/2014 | Helenek et al. | 512/502 |
| 9,120,838 B2 | 9/2015 | Demchenko et al. | |
| 9,353,193 B2 | 5/2016 | Quettier | |
| 9,439,969 B2 | 9/2016 | Andreasen | 536/112 |
| 10,478,450 B2 | 11/2019 | Helenek | |
| 10,519,252 B2 | 12/2019 | Geisser | |
| 2003/0191090 A1 | 10/2003 | Andreasen | |
| 2003/0023208 A1 | 12/2003 | Groman et al. | |
| 2003/0232084 A1 | 12/2003 | Groman et al. | 424/486 |
| 2004/0131703 A1 | 7/2004 | Bach et al. | |
| 2004/0180849 A1 | 9/2004 | Helenek et al. | 514/53 |
| 2005/0163849 A1 | 7/2005 | Wong et al. | |
| 2006/0116349 A1 | 6/2006 | Helenek et al. | 514/54 |
| 2006/0134227 A1 | 6/2006 | Bortz et al. | |
| 2006/0205691 A1 | 9/2006 | Geisser et al. | 514/59 |
| 2007/0161600 A1 | 7/2007 | Helenek et al. | 514/54 |
| 2008/0214496 A1 | 9/2008 | Tanner-Baumgartner | |
| 2008/0234226 A1 | 9/2008 | Erichsen et al. | 514/59 |
| 2009/0028962 A1 | 1/2009 | Bortz et al. | |
| 2011/0144054 A1 | 6/2011 | Groman et al. | |
| 2011/0287033 A1 | 11/2011 | Connor et al. | |
| 2012/0316133 A1 | 12/2012 | Geisser et al. | |
| 2013/0230565 A1 | 9/2013 | Helenek et al. | |
| 2014/0121193 A1 | 5/2014 | Katz et al. | 514/210.16 |
| 2014/0187514 A1 | 7/2014 | Tanner-Baumgartner et al. | |
| 2014/0364598 A1 | 12/2014 | Andreasen | 536/112 |
| 2015/0320031 A1 | 11/2015 | Andreasen | 435/1.3 |
| 2016/0333118 A1 | 11/2016 | Andreasen | 536/112 |
| 2018/0235997 A1 | 8/2018 | Helenek et al. | 514/58 |
| 2019/0276563 A1 | 9/2019 | Geisser et al. | |
| 2020/0215097 A1 | 7/2020 | Helenek | |
| 2021/0054105 A1 | 2/2021 | Geisser et al. | |

FOREIGN PATENT DOCUMENTS

| | | |
|---|---|---|
| CA | 2493806 | 5/2004 |
| CH | 423744 | 11/1966 |
| CN | 101365458 | 2/2009 |
| DE | 370194 | 8/1963 |
| EP | 0051707 | 5/1982 |
| EP | 0 150 085 A2 | 7/1985 |
| EP | 0150085 A2 | 7/1985 |
| EP | 0 543 020 A1 | 5/1993 |
| EP | 0543020 A1 | 5/1993 |
| EP | 0634174 | 7/1994 |
| EP | 0634174 A1 | 1/1995 |
| EP | 0543020 B1 | 12/1997 |
| EP | 1554315 B1 | 7/2005 |
| EP | 1231903 B1 | 1/2006 |
| EP | 3339329 A1 | 6/2018 |
| ES | 282099 | 11/1962 |
| GB | 335965 | 10/1930 |
| GB | 748024 | 4/1956 |
| GB | 879441 A | 10/1961 |
| GB | 985206 A | 3/1965 |
| GB | 1199951 | 7/1970 |
| KR | 10-2005-0070014 | 7/2005 |
| WO | 199009182 | 8/1990 |
| WO | 9711711 | 4/1997 |
| WO | WO 1997/011711 | 4/1997 |
| WO | 97/17377 A1 | 6/1997 |
| WO | 1999048533 | 9/1999 |
| WO | 00/30657 | 6/2000 |
| WO | 2000030657 | 6/2000 |
| WO | WO 00/61191 A2 | 10/2000 |
| WO | 200006634 | 11/2000 |
| WO | WO 02/07700 A2 | 1/2002 |
| WO | 2002/046241 A2 | 6/2002 |
| WO | WO 2002/46241 | 6/2002 |
| WO | 2004037865 | 5/2004 |
| WO | WO 2004/037865 | 5/2004 |
| WO | WO 2004/037865 A2 | 5/2004 |
| WO | 2004/108121 | 12/2004 |
| WO | WO 2007/023154 | 3/2007 |
| WO | WO 2007/081744 | 7/2007 |
| WO | 2011/055374 A2 | 5/2011 |
| WO | WO 2014/058516 | 4/2014 |
| WO | 2016/151367 A1 | 9/2016 |
| WO | 2016/181195 A1 | 11/2016 |

OTHER PUBLICATIONS

Ali, O., "Commissioning cost-effective delivery of intravenous iron," Prescriber, Navigator Series, pp. 43-46 (2011).

Alvares et al., "Evaluation of cardiac function in iron deficiency anemia before and after total dose iron therapy," J. Assoc. Physicians India 48(2):204-206 (2000).

Andersson, "Clinical investigations on a new intramuscular haematinic," British Med. J. 2(5249):275-279 (1961).

"Report of the ACS Carbohydrate Division Nomenclature Committee," presented at the Annual Meeting of the ACS Committee on Nomenclature, Terminology and Symbols, Apr. 7, 2008, New Orleans, 1 page.

Arond and Frank, "Molecular weight, molecular weight distribution and molecular size of a native dextran," J. Phys. Chem. 58(11):953-957 (1954).

Aronoff, G.R., "Safety of intravenous iron in clinical practice: implications for anemia management protocols," Journal of the American Society of Nephrology 15:S99-S106 (2004).

Assignment documents U.S. Appl. No. 11/620,986, dated Mar. 1 and 2, 2007, 4 pages.

Auerbach et al., "Low-molecular weight iron dextran and iron sucrose have similar comparative safety profiles in chronic kidney disease," Kidney International 73:528-530 (2008).

Auerbach et al., "Safety and efficacy of total dose infusion of 1,020 mg of ferumoxytol administered over 15 min," Am J Hemat 88(11):944-947 (2013).

Auerbach et al., "Intravenous Iron Optimizes the Response to Recombinant Human Erythropoietin in Cancer Patients with Chemotherapy-Related Anemia: A Multicenter, Open-Label, Randomized Trial," J. Clinical Oncology 22(7):1301-1307 (2004).

Auerbach et al., "Clinical Use of Intravenous Iron: Administration, Efficacy, and Safety," American Society of Hematology 2010(1):338-347 (2010).

Bailie et al., "Hypersensitivity reactions and deaths associated with intravenous iron preparations," Nephrol. Dial. Transplant 20:1443-1449 (2005).

Bailie, G. R., "Efficacy and safety of ferric carboxymaltose in correcting iron-deficiency anemia: a review of randomized controlled trials across different indications," Arzneimittelforschung 60(6a):386-398 (2010).

Bailie, G. R., "Breaking New Ground in Intravenous Iron Therapy," European Haematology pp. 58-60 (2008).

(56) References Cited

OTHER PUBLICATIONS

Beshara et al., "Pharmacokinetics and red cell utilization of $^{52}$Fe/$^{59}$Fe-labelled iron polymaltose in anaemic patients using positron emission tomography," British J. of Haematology 120:853-859 (2003).
Bingham et al., "Increased transfer of iron to the fetus after total dose infusion of iron dextran during pregnancy," J. Clin. Pathol. 36(8):907-909 (1983).
British Pharmacopoeia, Entry for Iron Dextran Injection, vol. II, pp. 2252-2253 (2002).
Caligur, "Dextran and Related Polysaccharides," BioFiles 3.10, 17, 7 pages. (2008).
Certificate of Analysis, "Anaemex 100 mL HDPE vials," Jan. 14, 1998, 1 page.
Certified English Translation of International Patent Publication No. WO 2004/037865, dated May 27, 2015, 20 pages.
Chandler et al., "Intravenous Iron Sucrose: Establishing a Safe Dose," American Journal of Kidney Diseases 38(5):988-991 (2001).
Chertow et al., "On the relative safety of parenteral iron formulations," Nephrol. Dial. Transplant 19(6):1571-1575 (2004).
Crichton et al., "Iron Therapy with Special Emphasis on Intravenous Administration," UNI-MED, 2nd Ed., cover page, foreword, acknowledgements, preface and contents; and chapters 7, 9, 10 and 11, 40 pages (2005).
Crichton et al., "Iron Therapy with Special Emphasis on Intravenous Administration: Iron Therapy and Oxidative Stress," UNI-MED, 2nd Ed., 4 pages (2005).
Cisar et al., "Binding properties of immunoglobulin combining sites specific for terminal or nonterminal antigenic determinants in dextran," J Exp Med 142:435-459 (1975).
C57BL/6 Mice Nomenclature: C57BL/6NCrl, Charles River Laboratories International, Inc. Pamphlet, 4 pages (2011).
"Comparative Test vs. DI (U.S. Pat. No. 3,639,588)," 2 pages.
Cook, "Diagnosis and management of iron-deficiency anaemia," Best Practice & Research Clinical Haematology 18(2):319-332 (2005).
Seid et al., Blood 108(11):3739 (2006), obtained from the British Library with a public availability date stamp and covering letter showing availability to the public on Dec. 6, 2006, 6 pages.
"CosmoFer®," Package insert, Revised Mar. 10, 2005, 2 pages.
CosmoFer® Summary of Product Characteristics, Dec. 2005, 13 pages.
CosmoFer® Summary of Product Characteristics (SmPC), Sep. 2003, 10 pages.
CosmoFer® UK Product Leaflet, 2001, 2 pages.
Curriculum Vitae of Dr. Adriana Manzi, 12 pages.
Danielson B.G., "Structure, chemistry, and pharmacokinetics of intravenous iron agents," J Am Soc Nephrol 15 Suppl 2:S93-S98 (2004).
Decision of the Technical Board of Appeal, dated Mar. 1, 2006, in connection with European Patent No. 0679508, 17 pages.
Declaration of Robert Linhardt, dated Jun. 17, 2015, 112 pages.
Declaration of Richard P. Lawrence, dated Dec. 5, 2012, 4 pages.
Declaration of Robert Linhardt, dated Jun. 22, 2015, 112 pages.
Declaration of Adriana Manzi, dated Mar. 29, 2016, 47 pages.
Declaration, Deponent: Adriana Manzi, Manzi Errata Sheet, dated Jun. 3, 2016, 3 pages.
Corrected Declaration of Adriana Manzi, dated Apr. 21, 2016, 47 pages.
Deposition of Robert Linhardt, dated Mar. 2, 2016, 189 pages.
Dexferrum® (Iron dextran injection, USP) Rx Only, NDA 40-024/S-022, American Regent, Inc., pp. 3-11.
Dextran 1 for Injection, European Pharmacopoeia 5.0, pp. 1408-1409.
Drugs.com, "Gleptosil Injection (Canada)," [cited Nov. 15, 2017]; available from: <URL:drugs.com/vet/gleptosil-injection-can.html, 3 pages.
Egeli et al., "An evaluation of iron-dextran supplementation in piglets administered by injection on the first, third or fourth day after birth," Res. Vet. Sci. 66(3):179-184 (1999).

"Elephants," San Diego Zoo Animals [online], retrieved on Jun. 13, 2016 from: <URL: animals.sandiegozoo.org/animals/elephant, 3 pages.
Eschbach et al., "NKF-K/DOQI clinical practice guidelines for anemia of chronic kidney disease: update 2000," Am J Kidney Dis 37(1):S182-238 (2001).
European Search Report, dated Oct. 21, 2009 in EP 07716309, 8 pages.
Excerpt of prosecution history of European Patent Application EP1973549, 4 pages.
Excerpt of prosecution history of European Patent Application EP1973549, 7 pages.
Excerpt of prosecution history of U.S. Pat. No. 7,754,702, 99 pages.
Prosecution history of U.S. Pat. No. 8,431,549, 244 pages.
Excerpt of prosecution history of U.S. Pat. No. 8,431,549, 75 pages.
Prosecution history of U.S. Pat. No. 8,895,612, 237 pages.
Excerpt of prosecution history of U.S. Pat. No. 8,895,612, 48 pages.
Excerpt from Der Bund, edition of Apr. 13, 2005, 3 pages [in German].
Excerpt from Der Bund, edition of Apr. 13, 2005, 3 pages [English translation].
"Executive Bios," Luitpold Pharmaceuticals [online], retrieved on Oct. 7, 2015 from: <URL: luitpold.com/ExecutiveBios.aspx, 4 pages.
Extract of MHRA Public Assessment Report for Ferinject® 50mg iron/ml solution for injection/infusion (Ferric carboxymaltose), 6 pages.
Extract from ClinicalTrials.gov website showing the details of trial No. NCT02397057 for the treatment of Restless Legs Syndrome, entitled "Placebo-Controlled Study to Investigate the Efficacy & Safety of Injectafer in the Treatment of RLS," last updated Jan. 24, 2018, 8 pages.
Extract from ClinicalTrials.gov website showing the details of trial No. NCT00396292, entitled "Comparison of the Safety and Efficacy of Intravenous Iron Versus Oral Iron in Subjects Who Display Postpartum Anemia," last updated Feb. 5, 2018, 16 pages.
Extract from ClinicalTrials.gov website, showing the details of trial No. NCT00317239, entitled "VIT45 Versus Oral Iron in the Treatment of Anemia in Non-Dialysis Dependent Chronic Kidney Disease," retrieved on Jun. 5, 2018, first posted on Apr. 24, 2006, and last updated on Feb. 20, 2018, 4 pages.
European Medicines Agency Science Medicines Health, "CHMP Assessment Report: Rienso, Common name: Ferumoxytol," dated Apr. 19, 2012, 79 pages.
Falbe et al., "Rompp Lexikon Chemie," p. 213, Georg Thieme Verlag [original document in German with certified English translation], 5 pages (1997).
"Feraheme: ferumoxytol injection," revised Mar. 2015, AMAG Pharmaceuticals, Inc. Pamphlet, 4 pages.
New Drug Application (NDA) 22-054 for Injectafer (Ferric Carboxymaltose) for the treatment of iron deficiency anemia in patients with heavy uterine bleeding or postpartum patients, FDA Advisory Committee Briefing Document: Drug Safety and Risk Management Committee, Feb. 1, 2008, 63 pages.
FDA Drug Safety Communications: "FDA strengthens warnings and changes prescribing instructions to decrease the risk of serious allergic reactions with anemia drug Feraheme (ferumoxytol)," Mar. 30, 2015, 4 pages.
"Ferrosig: Iron polymaltose 50 mg/ml Drug Product Data Sheet, Zuellig Pharma Limited," [online], retrieved on Feb. 16, 2016 from: <URL:medsafe.govt.nz/Profs/Datasheet/f/Ferrosiginj, prepared Jul. 10, 2003, 6 pages.
Fielding, "Intravenous iron-dextrin in iron-deficiency anaemia," British Med. J pp. 279-283 (1961).
Fishbane, "Safety in iron management," Am J Kidney Dis 41(6 Suppl 5):S18-S26 (2003).
Fisons Pharmaceuticals, "Imferon," US drug monograph, 2 pages (1989).
Folb, P. I., "The safety of iron dextran and a comparison with iron sucrose for intravenous use: a short report to the World Health Organization Advisory Committee on the safety of medicines," dated Oct. 18, 2004, 5 pages.

(56) References Cited

OTHER PUBLICATIONS

Funk et al., "Physical and Chemical Characterization of Therapeutic Iron Containing Materials: A Study of Several Supraparamagnetic Drug Formulations with the β-FeOOH or Ferrihydrite Structure," Hyperfine Interactions 136:73-95 (2001).
Funk et al., "The new generation of intravenous iron: chemistry, pharmacology, and toxicology of ferric carboxymaltose," Arzneimittelforschung 60(6a):345-353 (2010).
Galenica Ltd., "Venofer® approved by FDA ahead of company expectations for use in USA for treatment of iron deficiency anemia in pre-dialysis patients," published Jun. 20, 2005 [online], retrieved on Jun. 19, 2017, from <URL: evaluategroup.com/Universal/View.aspx?type=Story&id=140890, 1 page.
Geisser et al., "Structure/histotoxicity relationship of parenternal iron preparations," Drug Research 42(2):1439-1452 (1992).
Geisser et al., "Investigation on the Dosage/Efficacy Relationship of Iron Dextran in Veal Calves," Drug Res. 41(I), Nr. 1: 32-37 (1991).
Google Scholar Citation Listing for "van Zyl Smit," [online], retrieved on Oct. 7, 2015 from: <URL: scholar.google.com/scholar?hl=en&q=Experience+with+the+use+of+an+iron+polymaltose+%28dextrin%29+complex+given+by+single+total+dose+in . . . , 4 pages.
"Guidelines for administration of IV iron polymaltose in chronic kidney disease via continuous intravenous infusion," Royal Perth Hospital, 3 pages.
Google Scholar Search Results for ""ferrum hausmann" or polyisomaltose "blood loss" or emergency," [online], retrieved on Jul. 11, 2017, 2 pages.
Google Scholar Search Results for "ferrum hausmann "blood loss" or emergency," [online], retrieved on Jul. 10, 2017, 2 pages.
Google Scholar Search Results for "iron "high dose" safety," [online] retrieved on Jul. 11, 2017, 2 pages.
Google Scholar Search Results for "iron high "total dose infusion" hausmann or isomaltose or isomaltoside or polyisomaltose," [online] retrieved on Jul. 14, 2017, 2 pages.
Google Scholar Search Results for "iron isomaltoside or isomaltose," [online] retrieved on Jul. 14, 2017, 2 pages.
Grimes, A.J. and Hutt, M.S.R., "Metabolism of $^{59}$Fe-dextran complex in human subjects," Br. Med. J. 2(5053):1074-1077 (1957).
Gupte et al., "Iron Deficiency Anemia: Management and Prevention in Children," JK Science 3(4):160-165 (2001).
Haines et al., "Delayed adverse reactions to total-dose intravenous iron polymaltose," Internal Med. J. 39:252-255 (2009).
Hamstra et al., "Intrvenous iron dextran in clinical medicine," JAMA 243(17):1726-1731 (1980).
Hood et al., "The Safety of Intravenous Iron Dextran (Dexferrum®) During Hemodialysis in Patients with End Stage Renal Disease," Nephrol. Nurs. J. 27(1):41-42 (2000).
Hunnius Pharmazeutisches Worterbuch, 8th Edition, catchword "injections," p. 710 (1998) [In German].
Hunnius Pharmazeutisches Worterbuch, 8th Edition, catchword "injections," p. 710 (1998) [English translation, 1 page].
Imferon® (iron dextran injection, USP), Fisons Pharmaceuticals, revised May 1989, 2 pages.
Injectafer® (ferric carboxymaltose injection), American Regent, Inc., Pamphlet revised Jul. 2013, 11 pages.
INFed (iron dextran injection, USP), Schein Pharmaceutical, Inc., revised Sep. 1996, 2 pages.
"Iron Sorbitol Injection," British Pharmacopoeia Omitted Monograph, 4 pages (2003).
Jahn et al., "A comparative study of the physicochemical properties of iron isomaltoside 1000 (Monofer®), a new intravenous iron preparation and its clinical implications," European J. of Pharmaceutics and Biopharmaceutics 78:480-491 (2011).
Johansson et al. "Intravenous iron isomaltoside 1000 (Monofer®) reduces postoperative anaemia in preoperatively non-anaemic patients undergoing elective or subacute coronary artery bypass graft, valve replacement or a combination thereof: a randomized double-blind placebo-controlled clinical trial (the Protect trial)," Vox Sang 109(3):257-266 (2015).
Kabat et al., "Dextran—An antigen in man," J Immunol 70:514-532 (1953).
Kalra et al., "Iron isomaltoside 1000: a new high dose option for parenteral iron therapy," Port. J. Hypert. 26(1):13-24 (2012).
Keating, G. M., "Ferric Carboxymaltose: A Review of its Use in Iron Deficiency," Drugs 75:101-127 (2015).
Kudasheva et al., "Structure of carbohydrate-bound polynuclear iron oxyhydroxide nanoparticles in parenteral formulations," J. Inorgan. Biochem. 98:1757-1769 (2004).
Kulnigg et al., "A novel intravenous iron formulation for treatment of anemia in inflammatory bowel disease: the ferric carboxymaltose (FERINJECT) randomized controlled trial," Am J Gastroenterol 103(5):1182-1192 (2008).
Lam-Po-Tang et al., "Icodextrin Hypersensitivity in a CAPD Patient," Peritoneal Dialysis International [online], retrieved on Mar. 25, 2016 from: <URL:pdiconnect.com, 3 pages.
Landry et al., "Pharmacokinetic study of Ferumoxytol: A new iron replacement therapy in normal subjects and hemodialysis patients," Am. J. Nephrol. 25:400-410 (2005).
Leuillet, M. and Salmon-Legagneur, E., "Sur L'Utilisation D'Un Composé De Fer Dextrane Hydrogéné Par Injection Chez La Truie En Gestation Et En Lactation," Ann. Zootech. 17(1):59-70 (1968) [In French].
Certified English language translation of Leuillet et al. (1968) Ann. Zootech. 17(1):59-70, 12 pages.
Lindvall and Andersson, "Studies on a new intramuscular haematinic, iron-sorbitol," Brit. J. Pharmacol. 17:358-371 (1961).
Linhardt and Gunay, "Production and Chemical Processing of Low Molecular Weight Heparins," Seminars in Thrombosis and Hemostasis 25 (Suppl. 3):5-16 (1999).
London, E., "The molecular formula and proposed structure of the iron-dextran complex, IMFERON," J. Pharm. Sci. 93(7):1838-1846 (2004).
Lyseng-Williamson et al., "Ferric Carboxymaltose—A review of its use in iron-deficiency anaemia," Drugs 69(6):739-756 (2009).
MacDougall, "Intravenous administration of iron in epoetin-treated haemodialysis patients-which drugs, which regimen?" Nephrol Dial Transplant 15:1743-1745 (2000).
MacDougall et al., "Use of intravenous iron supplementation in chronic kidney disease" Iranian J. Kidney Dis. 7(1):9-22 (2013).
MacDougall, I.C., "Strategies for iron supplementation: Oral versus intrvenous" Kidney International 55(69): S61-66 (1999).
Mamula et al., "Total Dose Intravenous Infusion of Iron Dextran for Iron-Deficiency Anemia in Children With Inflammatory Bowel Disease," Journal of Pediatric Gastroenterology & Nutrition 34(3):286-290 (2002).
Manley and McClaran, "Determination of VIT 45 (IND#63,243—American Regent) removal by closed loop in vitro hemodialysis system," Int. J. Artif. Organs 29(11):1062-1066 (2006).
Marchasin et al., "The treatment of iron-deficiency anemia with intravenous iron dextran," Blood 23(3):354-358 (1964).
IUPAC Polysaccharide Nomenclature Recommendations 1980, 4 pages.
McCurdy et al., "Parenteral Iron Therapy With Special Reference to a New Preparation for Intramuscular Injection," The New England Journal of Medicine 257(24):1147-1153 (1957).
McNaught, "Nomenclature of Carbohydrates," Pure & Appl. Chem. 68(10):1919-2008 (1996).
Merriam-Webster Medical Dictionary [online], "hematinic," retrieved on May 28, 2015 from: <URL:merriam-webster.com/medical/hematinic, 1 page.
Mehmood et al.,"Response to intravenous iron in patients with iron deficiency anemia (IDA) and restless leg syndrome (Willis-Ekbom disease)," Sleep Med. 15(12):1473-1476 (2014).
Monofer Summary of Product Characteristics, revised Mar. 10, 2017, 5 pages.
Pharmacosmos, "MonoFer, Summary of Product Characteristics," revised Mar. 10, 2014, 5 pages.
Morris et al., "Conformation and Intermolecular Interactions of Carbohydrate Chains," Journal of Supramolecular Structure 6:259-274 (1977).

(56) References Cited

OTHER PUBLICATIONS

National Kidney Foundation, "NKF-K/DOQI Clinical Practice Guidelines for Hemodialysis Adequacy: Update 2000," Am. J. Kidney Dis. 37:S7-S64 (suppl 1) (2001).
National Kidney Foundation, "KDOQI Clinical Practice Guidelines and Clinical Practice Recommendations for Anemia in Chronic Kidney Disease," Am. J. Kidney Dis. 47(5):S1-S145 (suppl 3) (2006).
Neiser et al., "Assessment of dextran antigenicity of intravenous iron products by an immunodiffusion assay," Port. J. Hypert. 25(3):219-224 (2011).
Neiser et al., "Physico-chemical properties of the new generation IV iron preparations ferumoxytol, iron isomaltoside 1000 and ferric carboxymaltose," Biometals, published online Mar. 24, 2015, doi: 10.1007/s10534-015-9845-9, 21 pages.
Neiser et al., "Reply to the letter to the editor by Johannes Ring and Rudi Valenta on the article "Assessment of dextran antigenicity of intravenous iron products by an immunodiffusion assay,"" Port. J. Hypert. 26(4):311-312 (2012).
Newnham et al."Safety of iron polymaltose given as a total dose iron infusion," Internal Med. J. 36(10):672-674 (2006).
Nissenson et al., "Controversies in iron management," Kidney International 64(87):S64-S71 (2003).
Nissim, J.A., "Deposition of Iron in the Testes After Administration of an Iron-dextran Complex," The Lancet 268:701-702 (1955).
NKR-K/DOQI Clinical Practice Guidelines for Anemia of Chronic Kidney Disease: update 2000, Am. J. Kidney Dis. 37(1):S182-238 (2001).
Notice of Recordation of Assignment, dated Mar. 29, 2006, in connection with U.S. Appl. No. 60/757,119, 7 pages.
"Orange Book: Approved Drug Products with Therapeutic Equivalence Evaluations, Ferumoxytol," [online] retrieved on Mar. 9, 2015 from: <URL:accessdata.fda.gov/scripts/cder/ob/docs/patexclnew.cfm?Appl_No=022180&Product_No=00 1&table1=OB_Rx, 4 pages.
"Orange Book: Approved Drug Products with Therapeutic Equivalence Evaluations, Ferric Carboxymaltose," [online] retrieved on Mar. 9, 2015 from: <URL:accessdata.fda.gov/scripts/cder/ob/docs/patexclnew.cfm?Appl_No=203565&Product_No=00 1&table1=OB_Rx, 4 pages.
Accessdata, "Orange Book: Approved Drug Products with Therapeutic Equivalence Evaluations," [cited Nov. 21, 2017]; [online] available from: <URL:accessdata.fda.gov/scripts/cder/ob/patent_info.cfm?Product_No=001&Appl_No=0221 . . . , 3 pages.
Parham, P., "The Immune System. Chapter 1: Elements of the immune system and their roles in defense," Garland Publishing/Elsevier Science Ltd., pp. 1-30 (2000).
Paschen, H. W., "Effective anemia treatment involving the administration of high intravenous doses of iron," Geburtshilfe Frauenheilkunde 9:604-616 [Original document in German and English language translation], 28 pages.
Peacock and Lindenfeld, "Clinical Practice Guidelines for Maintaining Adequate Iron Status With Intravenous Iron Dextran in Hemodialysis Patients," ANNA J. 26(3):337-343(1999).
Pink Sheet Pharma Intelligence "Fisons' Opticrom, Imferon may be off U.S. Market Until Late 1992 as the company upgrades U.K. manufacturing plant to meet FDA quality control concerns," [online] retrieved on Jun. 13, 2016 from <URL:pharmamedtechbi.com/publications/the-pink-sheet/53/051/fisons-opticrom-imferon-may-be-off-us-market-until-late-1992-as-the-company-upgrade . . . , posted Dec. 23, 1991, 3 pages.
"Polysaccharide Nomenclature," Pure & Appl.Chem., 54(8):1523-1526 (1982).
Preusser et al., "Effects of intravenous ABT-870 (iron (III)-hydroxide oligosaccharide) on mean arterial pressure and heart rate in the anaesthetized beagle: comparison with other iron-containing heamatinic agents," Clin. Exp. Pharmacol. Physiol. 32(12):1020-1026 (2005).
"Promit® dextran 1: Consumer Medicine Information," [online] retrieved from <URL:mydr.com.au/cmis/promit-injection, dated Feb. 7, 2003, Published by MIMS Apr. 2005, 2 pages.

Prosecution history of U.S. Appl. No. 14/683,415, 192 pages.
Prosecution history of U.S. Appl. No. 13/847,254, 251 pages.
Prosecution history of U.S. Pat. No. 7,754,702, 343 pages.
Pugh-Clarke et al., "An Evidence-based Approach to Anaemia Management in Predialysis Chronic Kidney Disease," Journal of Renal Care 35(52):29-31 (2009).
Reinisch et al., "A randomized, open-label, non-inferiority study of intravenous iron isomaltoside 1,000 (Monofer) compared with oral iron for treatment of anemia in IBD (PROCEED)," Am. J. Gastroenterol 108(12):1877-88 (2013).
Reinisch et al., "A 1-year trial of repeated high-dose intravenous iron isomaltoside 1000 to maintain stable hemoglobin levels in inflammatory bowel disease," Scand. J. Gastroenterol. 50(10):1226-1233 (2015).
Research Subject Information and Consent Form, entitled "Evaluation of the safety, tolerability and pharmacokinetic profiles of single rising doses and increasing administration rates of ABT-870 in ESRD subjects on chronic hemodialysis with iron deficiency anemia," Sponsored by Abbott Laboratories, dated Apr. 30, 2004, 10 pages.
Screenshot showing document properties of the reproduction of the speech given by Dr. Barbara von Eisenhart-Rothe entitled "Clinical Development Programme of VIT-45," given at a Press conference on Apr. 12, 2005, 1 page.
Richter, A. W., "Immune Complex Anaphylaxis Induced by Dextran and its Elimination by Hapten Inhibition," in New Trends in Allergy II, J. Ring et al. (eds.), Springer-Verlag Berlin Heidelberg, pp. 272-283 (1986).
Ring and Valenta, "Letter and Reply to: Neiser et al. (2011) Assessment of dextran antigenicity of intravenous iron products by an immunodiffusion assay," Port. J. Nephrol. Hypert. 26(4), 3 pages (2012).
Roe, F. J. C., "On Potential Carcinogenecity of the Iron Macromolecular Complexes," UICC Monograph Series: Potential Carcinogenic Hazards from Drugs 7:105-116 (1967).
Safety Data Sheet, "Dextran T1 Technical Quality," [online], retrieved on May 27, 2015 from: <URL:dextran.net/products/technical-quality/c-24/c-74, 6 pages.
Sax and Lewis, "Hawley's Condensed Chemical Dictionary, Eleventh Edition," Van Nostrand Reinhold Company Inc., New York, pp. 797, 1081, 1082 (1987).
Screenshot showing results of Google search for "eisenhart rothe vit-45," 1 page.
Screenshot of Luitpold Pharmaceuticals homepage (<URL:luitpold.com/), showing the relationship between Luitpold and American Regent Inc., 1 page.
Seid et al., "Safety Profile of Iron Carboxymaltose, a New High Dose Intravenous Iron in Patients with Iron Deficiency Anemia," Blood 108(11):3739, 4 pages (2006).
Sergejew et al., "Chelator-induced iron excretion in iron-overloaded marmosets," Br. J. Haematol. 110(4):985-992 (2000).
Singh et al., "A comparison between intravenous iron polymaltose complex (Ferrets Hausmann®) and oral ferrous fumarate in the treatment of iron deficiency anaemia in pregnancy," Eur. J. Haematol. 60:119-124 (1998).
Silverberg et al., "Erythropoietin should be part of congestive heart failure management," Kidney Int. 64(Suppl. 87):S40-S47 (2003).
Silverberg et al., "The role of anemia in the progression of congestive heart failure. Is there a place for erythropoietin and intravenous iron?" J. Nephrol. 17(6):749-761 (2004).
Sipe et al., "Brain iron metabolism and neurodegenerative disorders," Dev. Neurosci. 24(2-3):188-196 (2002).
Sofic et al., "Increased iron (III) and total iron content in post mortem substantia nigra of parkinsonian brain," J. Neural. Transm. 74:199-205 (1988).
Speech given by Dr. Barbara von Eisenhart-Rothe at Galenica Press Conference 5005 on Apr. 12, 2005, Subject: "Clinical Development Programme of VIT-45," 3 pages.
Spinowitz et al., "The safety and efficacy of ferumoxytol therapy in anemic chronic kidney disease patients," Kidney International 68:1801-1807 (2005).
Syner-Med, "Summary of Product Characteristics; Ferinject," (2009), 8 pages.

(56) References Cited

OTHER PUBLICATIONS

Tagboto et al., "The efficacy of a single dose of intravenous ferric carboxymaltose (Ferinject®) on Anaemia in a pre-dialysis population of chronic kidney disease patients," Journal of Renal Care pp. 18-22 (2009).
Test for Iron Absorption, British Pharmacopoeia, p. 1364 (1968).
The Merck Index: An Encylopedia of Chemicals, Drugs and Biologicals, 14th Edition, O'Neil et al. editors, Merck Research Laboratories, pp. 501-502 (2006).
Transcript of the video deposition of Adrian. Manzi, Ph.D., dated May 12, 2016, Washington, D.C., 117 pages.
Transcript of the deposition of Robert Linhardt, Ph.D., Case: *Pharmacosmos A/S -v- Luitpold Pharmaceuticals, Inc.* (PTAB), dated Mar. 2, 2016, New York, New York, 189 pages.
UBS Report on Galenica's Financial Results, dated Apr. 15, 2004, 15 pages.
Ullmann's Encyclopedia of Industrial Chemistry, Sixth Edition, vol. 10, pp. 435-440 (2003).
Ullmann's Encyclopedia of Industrial Chemistry, Fifth Edition, vol. A8, pp. 449-454 (1987).
USP Pharmacists' Pharmacopeia, 2nd Edition, The United States Pharmacopeial Convention, Inc., 166 pages (2009).
"USP28-NF23, Official Monographs/Dextran," pp. 601-602, The United States Pharmacopeial Convention, Inc. (2004).
USPTO Patent Full-Text and Image Database, "Help on the Quick Search Page," 5 pages.
Van Wyck et al., "Making sense: a scientific approach to intravenous iron therapy," J. Am. Soc. Nephrol. 15(2):591-592 (2004).
Van Wyck et al., "Labile iron: manifestations and clinical implicaations," J. Am. Soc. Nephrol. 15(2):S107-S111 (2004).
Van Wyck et al., "Labile iron in parenteral iron formulations: a quantitative and comparative study," Nephrol. Dial. Transplant. 19:561-565 (2004).
Van Wyck et al., "A randomized, controlled trial comparing IV iron sucrose to oral iron in anemic patients with nondialysis-dependent CKD," Kidney International 68:2846-2856 (2005).
Van Wyck et al., "Intravenous Ferric Carboxymaltose Compared with Oral Iron in the Treatment of Postpartum Anemia," Obstetrics & Gynecology 110(2), Part 1, pp. 267-278 (2007).
Van Zyl Smit et al., "Experience with the use of an iron polymaltose (Dextrin) complex given by single total dose infusion to stable chronic haemodialysis patients," Nephron 92:316-323 (2002).
Vollhardt and Schore, "Organic Chemistry Structure and Function. Chapter 24: Carbohydrates Polyfunctional Compounds in Nature," Fifth Edition, W.H. Freeman and Company, New York, pp. 1096-1138 (2007).
Wallerstein, R. O., "Intravenous Iron-Dextran Complex," Blood 32(4):690-695 (1968).
Walters and Van Wyck, "Benchmarking iron dextran sensitivity: reactions requiring resuscitative medication in incident and prevalent patients," Nephrol. Dial. Transplant. 20:1438-1442 (2005).
Wang et al., "Comparative Risk of Anaphylactic Reactions Associated with Intavenous Iron Products," JAMA 314(19):2062-2068 (2015).
Wang et al., Supplementary Online Content for "Comparative Risk of Anaphylactic Reactions Associated with Intavenous Iron Products," JAMA 314(19):2062-2068 (2015), 19 pages.
Webster's Ninth New Collegiate Dictionary, pp. 19, 20, 985, 994 (1986), 6 pages.
Zager et al., "Parenteral iron nephrotoxicity: Potential mechanisms and consequences," Kidney International 66:144-156 (2004).
Zhang et al., "Tandem MS can Distinguish Hyaluronic Acid from N-Acetylheparosan," J. Am. Soc. Mass Spectrom. 19(1):82-90 (2008).
"21 Years later . . . One group, two strategies. Separation scheduled for Q4 2016," Galenica Group Presentation, Apr. 2016, 48 pages.
American Regent Press Release, "American Regent Announces Enrollment of First Patient in Phase 3 Trial to Investigate Injectafer® (Ferric Carboxymaltose) as Treatment for Heart Failure with Iron Deficiency," Published Apr. 24, 2017 [online]; Retrieved on Oct. 17, 2017, from <URL:americanregent.com/Documents/ARNews/American_Regent_HEART-FID_Clinical_Trial_FPI_Press_Release_FINAL-4_21.pdf , 3 pages.
Luitpold Press Release, "American Regent Announces an FDA Pediatric Indication Exclusivity for Venofer (Iron Sucrose Injection, USP)," Published Oct. 19, 2012 [online]; Retrieved on Oct. 16, 2017, from <URL:luitpold.com/documents/news/SlaqafRbOnQomqzQJHcw==.pdf, 16 pages.
Luitpold Press Release, "American Regent announces a new FDA-Approved Pediatric Indication for Venofer® (Iron Sucrose Injection, USP)", Published Sep. 26, 2012 [online]; Retrieved on Oct. 16, 2017, from <URL:luitpold.com/documents/news/1NMbGpxMEVk=.pdf, 16 pages.
Luitpold Press Release, "American Regent announces FDA approval for Venofer® in the treatment of iron deficiency anemia in peritoneal dialysis patients," Published Oct. 17, 2005 [online]; Retrieved on Oct. 16, 2017, from <URL:luitpold.com/documents/news/TdpFxv064UU=.pdf, 2 pages.
Luitpold Press Release, "American Regent announces new PDUFA action date for Injectafer® (ferric carboxymaltose injection) NDA for the treatment of iron deficiency anemia," Published Apr. 8, 2013 [online]; Retrieved on Oct. 16, 2017, from <URL:luitpold.com/documents/news/GvrNvPISehlqdL9Ldjhgkw==.pdf, 2 pages.
Luitpold Press Release, "American Regent's Injectafer® (Ferric Carboxymaltose Injection) Assigned Q Code by Centers for Medicare and Medicaid Services," Published May 1, 2014 [online]; Retrieved on Oct. 16, 2017, from <URL:luitpold.com/documents/news/lE7UsdIztevebKp+Zgn07w==.pdf, 5 pages.
Luitpold Press Release, "American Regent Resumes Shipment of Injectable Products," Published May 6, 2011 [online]; Retrieved on Oct. 16, 2017, from <URL:luitpold.com/documents/news/NSQdwNibxrY=.pdf, 2 pages.
Luitpold Press Release, "American Regent Resumes Shipment of Venofer® (iron sucrose injection, USP)," Published May 3, 2011 [online]; Retrieved on Oct. 16, 2017, from <URL:luitpold.com/documents/news/lKZCDYvETdw=.pdf, 1 page.
Luitpold Press Release, "FDA Advisory Committee Supports Favorable Risk-Benefit Profile for Injectafer™ (Ferric Carboxymaltose Injection) Under Certain Indications for Use," Published Feb. 4, 2008 [online]; Retrieved on Oct. 16, 2017, from <URL:luitpold.com/documents/news/z+dV+KHfJMc=.pdf, 2 pages.
Luitpold Press Release, "FDA Assigns PDUFA Date for Injectafer® (ferric carboxymaltose injection) NDA," Published Dec. 15, 2011 [online]; Retrieved on Oct. 16, 2017, from <URL:luitpold.com/documents/news/MIPDRvQ+mjk=.pdf, 2 pages.
Luitpold Press Release, "Important Drug Product Notice: Luitpold Pharmaceuticals, Inc. Announces Temporary Suspension of Distribution and Manufacture of Drug Products," Published Apr. 21, 2011 [online]; Retrieved on Oct. 16, 2017, from <URL:luitpold.com/documents/news/0eLJIVKb5rc=.pdf, 1 page.
Luitpold Press Release, "Injectafer® (ferric carboxymaltose injection) receives US FDA approval for the treatment of Iron Deficiency Anemia," Published Jul. 25, 2013 [online]; Retrieved on Oct. 16, 2017, from <URL:luitpold.com/documents/news/9Fo4fHAOE0SHYfSyNdTbkw==.pdf, 3 pages.
Luitpold Press Release, "Luitpold Pharmaceuticals/American Regent and Fresenius Medical Care sign agreements for exclusive sublicense of Venofer® in U.S.," Published Jul. 9, 2008 [online]; Retrieved on Oct. 16, 2017, from <URL:luitpold.com/documents/news/VysTqXcRR2s=.pdf, 2 pages.
Luitpold Press Release, "Luitpold Pharmaceuticals/American Regent announces closing of exclusive sublicense of Venofer® by Fresenius Medical Care in U.S.," Published Sep. 16, 2008 [online]; Retrieved on Oct. 16, 2017, from <URL:luitpold.com/documents/news/YHGinfwHwlE=.pdf, 2 pages.
Luitpold Press Release, "Luitpold Pharmaceuticals Injectafer™ (ferric carboxymaltose injection) receives non-approvable letter from FDA," Published Mar. 12, 2008 [online]; Retrieved on Oct. 16, 2017, from <URL:luitpold.com/documents/news/wSxUljvMZ08=.pdf, 2 pages.
Luitpold Press Release, "Luitpold Pharmaceuticals, Inc. Receives Complete Response Letter for Injectafer® from the U.S. Food and

(56) References Cited

OTHER PUBLICATIONS

Drug Administration," Published Jul. 26, 2012 [online]; Retrieved on Oct. 16, 2017, from <URL:luitpold.com/documents/news/RGFqg0SyN9s=.pdf, 2 pages.
Luitpold Press Release, "Luitpold Pharmaceuticals, Inc. submits Injectafer® NDA to the U.S. Food and Drug Administration," Published Oct. 13, 2011 [online]; Retrieved on Oct. 16, 2017, from <URL:luitpold.com/documents/news/MC0f+G2pkOM=.pdf, 2 pages.
Luitpold Press Release, "Venofer® (iron sucrose injection, USP) receives FDA approval for the treatment of iron deficiency anemia in pre-dialysis patients," American Regent, Jun. 17, 2005, 2 pages.
Office Action, dated Dec. 15, 2009, in connection with U.S. Appl. No. 11/620,986, 21 pages.
Response, dated Jan. 8, 2010, in connection with U.S. Appl. No. 11/620,986, 13 pages.
Notice of Allowance, dated Apr. 5, 2010, in connection with U.S. Appl. No. 11/620,986, 12 pages.
Petition for Inter Partes Review of U.S. Pat. No. 7,754,702, mailed Jun. 24, 2015, in connection with U.S. Appl. No. 11/620,986, 65 pages.
Patent Owner Preliminary Response, mailed Oct. 12, 2015, in connection with U.S. Appl. No. 11/620,986, 39 pages.
Decision, dated Jan. 8, 2016, in connection with U.S. Appl. No. 11/620,986, 20 pages.
Order Conduct of the Proceedings, mailed Mar. 11, 2016, in connection with U.S. Appl. No. 11/620,986, 6 pages.
Patent Owner Response, mailed Mar. 29, 2016, in connection with U.S. Appl. No. 11/620,986, 47 pages.
Patent Owner Exhibit List as of Mar. 29, 2016, mailed Mar. 29, 2016, in connection with U.S. Appl. No. 11/620,986, 7 pages.
Motion to Amend, mailed Mar. 29, 2016, in connection with U.S. Appl. No. 11/620,986, 48 pages.
Petitioner's Notice of Objections to Evidence, mailed Apr. 5, 2016, in connection with U.S. Appl. No. 11/620,986, 5 pages.
Corrected Patent Owner Exhibit List as of Apr. 25, 2016, mailed Apr. 25, 2016, in connection with U.S. Appl. No. 11/620,986, 7 pages.
Corrected Motion to Amend, mailed Apr. 25, 2016, in connection with U.S. Appl. No. 11/620,986, 48 pages.
Petitioner's Reply to Patent Owner Response, mailed Jun. 20, 2016, in connection with U.S. Appl. No. 11/620,986, 32 pages.
Petitioner's Opposition to Patent Owner's Motion to Amend, mailed Jun. 20, 2016, in connection with U.S. Appl. No. 11/620,986, 31 pages.
Objections to Petitioner's Reply and Opposition Evidence, mailed Jun. 27, 2016, in connection with U.S. Appl. No. 11/620,986, 5 pages.
Patent Owner Reply to Opposition to Motion to Amend, mailed Jul. 19, 2016, in connection with U.S. Appl. No. 11/620,986, 20 pages.
Patent Owner Motion to Exclude, mailed Aug. 9, 2016, in connection with U.S. Appl. No. 11/620,986, 19 pages.
Order Conduct of the Proceedings, mailed Aug. 19, 2016, in connection with U.S. Appl. No. 11/620,986, 3 pages.
Order for Trial Hearing, mailed Aug. 22, 2016, in connection with U.S. Appl. No. 11/620,986, 5 pages.
Petitioner's Opposition to Patent Owner's Motion to Exclude, mailed Aug. 23, 2016, in connection with U.S. Appl. No. 11/620,986, 19 pages.
Patent Owner Reply to Opposition to Motion to Exclude, mailed Aug. 30, 2016, in connection with U.S. Appl. No. 11/620,986, 9 pages.
Record, dated Nov. 3, 2016, of Oral Hearing, held Sep. 22, 2016, in connection with U.S. Appl. Nos. 11/620,986 and 12/787,283, 104 pages.
Final Written Decision, dated Jan. 4, 2017, in connection with U.S. Appl. No. 11/620,986, 52 pages.
Notice of Federal Circuit Appeal, filed Mar. 2, 2017 by Luitpold Pharmaceuticals, Inc., in connection with U.S. Pat. No. 7,754,702, 5 pages.
Order for Case Dismissal of PTAB Appeal No. IPR2015-01490, filed Apr. 12, 2018, in connection with U.S. Pat. No. 7,754,702, 2 pages.
Notice of Entry of Judgement Without Opinion and Judgement, entered Apr. 12, 2018, in connection with PTAB Appeal Nos. IPR2015-01490 (U.S. Pat. No. 7,754,702) and IPR2015-01493 (U.S. Pat. No. 8,431,549), 5 pages.
Application for Patent Term Extension, filed Jul. 24, 2009, in connection with U.S. Pat. No. 6,599,498, 121 pages.
Application for Patent Term Extension, filed Sep. 19, 2013, in connection with U.S. Pat. No. 7,612,109, 75 pages.
Amendment and Response, dated Jun. 9, 2014, and Office Action, dated Feb. 7, 2014, in connection with U.S. Appl. No. 14/100,717, 34 pages.
Amendment and Response, dated Jun. 9, 2014, to Office Action, dated Feb. 7, 2014, in connection with U.S. Appl. No. 14/100,717, 19 pages.
Notice of Federal Circuit Appeal, filed Mar. 1, 2017 by Luitpold Pharmaceuticals, Inc., in connection with U.S. Pat. No. 8,431,549, 4 pages.
Office Action, dated Jun. 6, 2012, in connection with U.S. Appl. No. 12/787,283, 13 pages.
Response, dated Dec. 6, 2012, to Office Action, dated Jun. 6, 2012, in connection with U.S. Appl. No. 12/787,283, 34 pages.
Applicant-Initiated Interview Summary, dated Feb. 6, 2013, in connection with U.S. Appl. No. 12/787,283, 4 pages.
Notice of Allowance, dated Feb. 28, 2013, in connection with U.S. Appl. No. 12/787,283, 14 pages.
Certifcate Extending Patent Term, in connection with U.S. Pat. No. 6,599,498, dated Mar. 26, 2014, 144 pages.
Petition of Inter Partes Review of U.S. Pat. No. 8,431,549, mailed Jun. 24, 2015, in connection with U.S. Appl. No. 12/787,283, 67 pages.
Patent Owner Preliminary Response, mailed Oct. 12, 2015, in connection with U.S. Appl. No. 12/787,283, 65 pages.
Order Conduct of the Proceedings, entered Oct. 14, 2015, in connection with U.S. Appl. No. 12/787,283, 4 pages.
Notice of Response in lieu of Motion, mailed Oct. 20, 2015, in connection with U.S. Appl. No. 12/787,283, 4 pages.
Petitioner's Objection to Patent Owner Response in Lieu of Motion, mailed Oct. 30, 2015, in connection with U.S. Appl. No. 12/787,283, 4 pages.
Inter. Partes Review Decision, entered Jan. 8, 2016, in connection with U.S. Appl. No. 12/787,283, 24 pages.
Request for Rehearing, mailed Jan. 22, 2016, in connection with U.S. Appl. No. 12/787,283, 8 pages.
Patent Owner Objections to Evidence, mailed Jan. 27, 2016, in connection with U.S. Appl. No. 12/787,283, 4 pages.
Revised Patent Owner Notice of Deposition of Dr. Linhardt, mailed Feb. 19, 2016, in connection with U.S. Appl. No. 12/787,283, 3 pages.
Decision Denying Petitioner's Request for Rehearing, entered Feb. 26, 2016, in connection with U.S. Appl. No. 12/787,283, 5 pages.
Order re Conference Call on Mar. 9, 2016, entered Mar. 11, 2016, in connection with U.S. Appl. No. 12/787,283, 6 pages.
Patent Owner Exhibit List as of Jul. 19, 2016 in connection with U.S. Appl. No. 12/787,283, 7 pages.
Patent Owner Reply to Opposition to Motion to Amend, mailed Jul. 19, 2016, in connection with U.S. Appl. No. 12/787,283, 20 pages.
Order of Rehearing, mailed Aug. 22, 2016, in connection with U.S. Appl. No. 12/787,283, 5 pages.
Inter Partes Review Final Written Decision, filed Dec. 28, 2016, in connection with U.S. Appl. No. 12/787,283, 28 pages.
Examiner's Report, dated Jun. 28, 2017, in connection with Canadian Patent Application No. 2,953,964, 9 pages.
Brief of Appellant Luitpold Pharmaceuticals, Inc., filed Jul. 27, 2017, in connection with U.S. Pat. Nos. 7,754,702 and 8,431,549, 164 pages.
Principal and Response Brief of Appellee and Cross-Appellant Pharmacosmos A/S, filed Sep. 5, 2017, in connection with U.S. Pat. Nos. 7,754,702 and 8,431,549, 86 pages.

(56) References Cited

OTHER PUBLICATIONS

Corrected Response and Reply Brief of Appellant Luitpold Pharmaceuticals, Inc., filed Oct. 30, 2017, in connection with U.S. Pat. Nos. 7,754,702 and 8,431,549, 62 pages.
Citation of Supplemental Authority, filed Nov. 2, 2017 by Pharmacosmos A/S in connection with U.S. Pat. Nos. 7,754,702 and 8,431,549, 2 pages.
Response, filed Nov. 6, 2017 by Luitpold Pharmaceuticals, Inc., to the Citation of Supplemental Authority, filed Nov. 2, 2017 by Pharmacosmos A/S in connection with U.S. Pat. Nos. 7,754,702 and 8,431,549, 2 pages.
Reply Brief of Cross-Appellant Pharmacosmos A/S, filed Nov. 13, 2017, in connection with U.S. Pat. Nos. 7,754,702 and 8,431,549, 23 pages.
Mandate, issued May 21, 2018, in connection with Appeal Nos. IPR2015-01493 (U.S. Pat. No. 8,431,549) and IPR2015-01490 (U.S. Pat. No. 7,754,702), 1 page.
Office Action, dated Apr. 7, 2014, in connection with U.S. Appl. No. 13/847,254, 17 pages.
Response, dated Jul. 3, 2014, to Office Action, dated Apr. 7, 2014, in connection with U.S. Appl. No. 13/847,254, 18 pages.
Final Office Action, dated Oct. 14, 2014, in connection with U.S. Appl. No. 13/847,254, 14 pages.
Office Action, dated Feb. 7, 2014, in connection with U.S. Appl. No. 14/100,717, 15 pages.
Response, filed Jun. 9, 2014, to Office Action, dated Feb. 7, 2014, in connection with U.S. Appl. No. 14/100,717, 19 pages.
Notice of Allowance, dated Sep. 22, 2014, in connection with U.S. Appl. No. 14/100,717, 14 pages.
Petition for Inter Partes Review of U.S. Pat. No. 8,895,612, filed Jun. 24, 2015, in connection with U.S. Appl. No. 14/100,717, 68 pages.
Patent Owner Preliminary Reponse, dated Oct. 12, 2015, to Petition for Inter Partes Review, filed Jun. 24, 2015, in connection with U.S. Appl. No. 14/100,717, 70 pages.
Decision Denying Institution of Inter Partes Review, entered Jan. 8, 2016, in connection with U.S. Appl. No. 14/100,717, 23 pages.
Office Action, dated Jul. 26, 2017, in connection with U.S. Appl. No. 14/683,415, 59 pages.
Response, filed Jan. 26, 2018, to Office Action, dated Jul. 26, 2017, in connection with U.S. Appl. No. 14/683,415, 62 pages.
Notice of Allowance, dated Jun. 8, 2018, in connection with U.S. Appl. No. 14/683,415, 13 pages.
Corrected Notice of Allowability, dated Jun. 25, 2018, in connection with U.S. Appl. No. 14/683,415, 6 pages.
Notice of Allowability, dated Sep. 13, 2018, in connection with U.S. Appl. No. 14/683,415, 7 pages.
Corrected Notice of Allowability, dated Oct. 11, 2018, in connection with U.S. Appl. No. 14/683,415, 4 pages.
International Search Report and Written Opinion, dated Sep. 12, 2007, in connection with International Patent Application No. PCT/US07/00176, 6 pages.
Office Action, dated Sep. 15, 2011, in connection with Australian Patent Application No. 2007205167, 3 pages.
Response, dated May 17, 2013, to Office Action, issued in connection with Australian Patent Application No. 2007205167, 28 pages.
Notice of Acceptance, dated Jun. 4, 2013, in connection with Australian Patent Application No. 2007205167, 1 page.
Examination Report, dated Apr. 13, 2015, in connection with Australian Patent Application No. 2013206429, 4 pages.
Response, dated Mar. 22, 2016, to Examination Report, dated Apr. 13, 2015, in connection with Australian Patent Application No. 2013206429, 36 pages.
Notice of Acceptance, dated Apr. 14, 2016, in connection with Australian Patent Application No. 2013206429, 3 pages.
Examination Report, dated Jan. 11, 2017, in connection with Australian Patent Application No. 2016205002, 5 pages.
Response, filed Jan. 10, 2018, to Examination Report, dated Jan. 11, 2017, in connection with Australian Patent Application No. 2016205002, 23 pages.
Notice of Acceptance, dated Jan. 11, 2018, in connection with Australian Patent Application No. 2016205002, 2 pages.
Notice of Opposition by Pharmacosmos Holding A/S, issued Apr. 30, 2018, in connection with Australian Patent Application No. 2016205002, 3 pages.
Statement of Grounds and Particulars, filed Jul. 30, 2018, in support of the Notice of Opposition, filed Apr. 30, 2018 by Pharmacosmos Holding A/S, in connection with Australian Patent Application No. 2016205002, 25 pages.
Declaration by Dr. Kim Nordjfeld of Pharmacosmos A/S (Denmark), dated Sep. 11, 2018, submitted in connection with the Opposition to Australian Patent Application No. 2016205002, 3 pages.
Declaration by Hans Berg Andreasen of Pharmacosmos A/S (Denmark), dated Sep. 13, 2018, submitted in connection with the Opposition to Australian Patent Application No. 2016205002, 1 page.
Declaration by Kathryn Barbara Morris of Griffith Hack, dated Oct. 25, 2018, submitted in connection with the Opposition to Australian Patent Application No. 2016205002, 16 pages.
Amended Statement of Grounds and Particulars, dated Oct. 3, 2018, in support of the Notice of Opposition, filed Apr. 30, 2018 by Pharmacosmos Holding A/S, in connection with Australian Patent Application No. 2016205002, 43 pages.
Joint Appendix, filed Nov. 17, 2017, in connection with U.S. Pat. Nos. 7,754,702 and 8,431,549, 723 pages.
Office Action, dated Jan. 4, 2013, in connection with Canadian Patent Application No. 2,635,894, 4 pages.
Response, dated Jul. 4, 2013, to Examiner's Report, dated Jan. 4, 2013, in connection with Canadian Patent Application No. 2,635,894, 26 pages.
Examiner's Report, dated Oct. 17, 2013, in connection with Canadian Patent Application No. 2,635,894, 4 pages.
Response, dated Apr. 16, 2014, to Examiner's Report, dated Oct. 17, 2013, in connection with Canadian Patent Application No. 2,635,894, 33 pages.
Examiner's Report, dated Oct. 10, 2014, in connection with Canadian Patent Application No. 2,635,894, 7 pages.
Response, dated Apr. 8, 2015, to Examiner's Report, dated Oct. 10, 2014, in connection with Canadian Patent Application No. 2,635,894, 30 pages.
Examiner's Report, dated Sep. 29, 2015, in connection with Canadian Patent Application No. 2,635,894, 8 pages.
Response, dated Mar. 23, 2016, to Examiner's Report, dated Sep. 29, 2015, in connection with Canadian Patent Application No. 2,635,894, 19 pages.
Examiner's Report, dated May 16, 2016, in connection with Canadian Patent Application No. 2,635,894, 8 pages.
Response, dated Nov. 15, 2016, to Examiner's Report, dated May 16, 2016, in connection with Canadian Patent Application No. 2,635,894, 24 pages.
Notice of Allowance, dated Mar. 8, 2017, in connection with Canadian Patent Application No. 2,635,894, 1 page.
Response, filed Dec. 28, 2017, to Examiner's Report, dated Jun. 28, 2017, in connection with Canadian Patent Application No. 2,953,964, 36 pages.
Examiner's Report, dated Mar. 9, 2018, in connection with Canadian Patent Application No. 2,953,964, 5 pages.
Response, filed Sep. 10, 2018, to Examiner's Report, dated Mar. 9, 2018, in connection with Canadian Patent Application No. 2,953,964, 43 pages.
Office Action, dated Apr. 30, 2010, in connection with Chinese Patent Application No. CN200780002006 [English translation], 7 pages.
Invalidation Request, filed Jun. 20, 2016, in connection with Chinese Patent Application No. 200780002006 [English translation, document as filed in Chinese and Notice of acceptance of invalidation request as issued in Chinese], 174 pages.
Response, filed Aug. 23, 2016, to Invalidation Request, filed Jun. 20, 2016, in connection with Chinese Patent Application No. 200780002006 [English instructions, document as filed in Chinese and claims as filed in English], 118 pages.

(56) References Cited

OTHER PUBLICATIONS

Notice of Oral Hearing, issued Aug. 31, 2016, in connection with Chinese Patent Application No. 200780002006 [English translation], 5 pages.
Post Hearing Observations, filed Dec. 8, 2016, on Response, filed Aug. 23, 2016, to Invalidation Request, filed Jun. 20, 2016, in connection with Chinese Patent Application No. 200780002006 [English instructions for response, document as filed in Chinese and English translation of filed claims], 57 pages.
Extended Search Report, dated Oct. 21, 2009, in connection with European Patent Application No. 07716309.5, 8 pages.
Examination Report, dated May 10, 2011, in connection with European Patent Application No. 07716309.5, 6 pages.
Response, dated Nov. 9, 2011, to Search Report, dated May 10, 2011, in connection with European Patent Application No. 07716309.5, 12 pages.
Official Communication, dated Jun. 4, 2012, in connection with European Patent Application No. 07716309.5, 5 pages.
Response, dated Dec. 14, 2012, to Examination Report, dated Jun. 4, 2012, in connection with European Patent Application No. 07716309.5, 17 pages.
Examination Report, dated Jul. 5, 2013, in connection with European Patent Application No. 07716309.5, 5 pages.
Patent Term Extension Application, filed Sep. 19, 2013, in connection with U.S. Pat. No. 7,612,109, 16 pages.
Response, dated Jan. 15, 2014, to Examination Report, dated Jul. 5, 2013, in connection with European Patent Application No. 07716309.5, 19 pages.
Third Party Observations, submitted Oct. 31, 2014, and Communication pursuant to Rule 114(2) EPC, dated Nov. 10, 2014, in connection with European Patent Application No. 07716309.5 [Third party observations, Communication and cited references], 22 pages.
Summons to Attend Oral Proceedings, dated Feb. 9, 2015, issued in connection with European Patent Application No. 07716309.5, 4 pages.
Response, dated Oct. 30, 2015, to Summons to Attend Oral Proceedings, dated Feb. 9, 2015, in connection with European Patent Application No. 07716309.5, 98 pages.
Third Party Observations, submitted Nov. 11, 2015, and Communication maintaining the date/time for oral proceedings, dated Nov. 12, 2015, in connection with European Patent Application No. 07716309.5, 4 pages.
Response, dated Nov. 27, 2015, to Notice Concerning the Oral Proceedings, dated Nov. 19, 2015, in connection with European Patent Application No. 07716309.5, 67 pages.
Decision to Grant, dated Jun. 23, 2016, issued in connection with European Patent Application No. 07716309.5, 2 pages.
Notice of Opposition to a European Patent, submitted by Hoffman Eitle Patent—und Rechtsanwalte PartmbB on Apr. 10, 2017, in connection with European Patent No. 1 973 549, 20 pages.
Notice, dated Apr. 24, 2017, of Opposition to a European Patent, submitted by Pharmacosmos Holding A/S on Apr. 13, 2017, in connection with European Patent No. 1 973 549, 30 pages.
Notice of Opposition, submitted by Teva Pharmaceutical Industries Ltd. on Apr. 18, 2017, in connection with European Patent No. 1 973 549, 15 pages.
Notice of Opposition, submitted by HGF Limited on Apr. 19, 2017, in connection with European Patent No. 1 973 549, 20 pages.
Notice of Opposition, submitted by STADA Arzneimittel AG on Apr. 20, 2017, in connection with European Patent No. 1 973 549, 42 pages [In German].
Notice of Opposition, submitted by STADA Arzneimittel AG on Apr. 20, 2017, in connection with European Patent No. 1 973 549 [English translation], 26 pages.
Notice of Opposition, submitted by Taylor Wessing LLP on Apr. 20, 2017, in connection with European Patent No. 1 973 549, 29 pages.
Notice of Opposition, submitted by Generics (U.K.) Limited on Apr. 20, 2017, in connection with European Patent No. 1 973 549, 25 pages.
Reply of the Patent Proprietor Vifor (International) AG, filed Feb. 2, 2018, to the Notices of Opposition, dated May 26, 2017, in connection with European Patent No. 1 973 549, 169 pages.
Response of Opponent Pharmacosmos Holding A/S, filed Mar. 9, 2018, to Reply of Patent Proprietor Vifor (International) AG, filed Feb. 2, 2018, in connection with European Patent No. 1 973 549, 15 pages.
Summons to Attend Oral Proceedings Pursuant to Rule 115(1) EPC, dated Jun. 5, 2018, in connection with European Patent No. 1973549, 8 pages.
Third Party Observation for Application No. EP20070716309, submitted Jul. 23, 2018, in connection with European Patent No. 1973549, 3 pages.
Written Submissions of Taylor Wessing LLP, filed on Sep. 3, 2018, in response to the Reply of the Patent Proprietor Vifor, dated Feb. 2, 2018, to the Notices of Opposition, in connection with European Patent No. 1 973 549, 18 pages.
Written Submission of HGF Limited, filed on Sep. 21, 2018, in connection with the Opposition to European Patent No. 1 973 549, 10 pages.
Search Report, dated Jul. 8, 2013, in connection with European Patent Application No. 13166988.9, 8 pages.
Examination Report, dated Apr. 7, 2014, in connection with European Patent Application No. 13166988.9, 4 pages.
Response, dated Oct. 17, 2014, to Examination Report, dated Apr. 7, 2014, in connection with European Patent Application No. 13166988.9, 13 pages.
Third Party Observations, submitted Nov. 3, 2014, in connection with European Patent Application No. 13166988.9, 2 pages.
Summons to Attend Oral Proceedings, dated Feb. 10, 2015, in connection with European Patent Application No. 13166988.9, 6 pages.
Response, dated Oct. 30, 2015, to Summons to Attend Oral Proceedings, dated Feb. 10, 2015, in connection with European Patent Application No. 13166988.9, 91 pages.
Third Party Observations, submitted Nov. 11, 2015, and Communication maintaining the date/time for oral proceeding, dated Nov. 12, 2015, in connection with European Patent Application No. 13166988.9, 4 pages.
Response, dated Nov. 23, 2015, to Summons to Attend Oral Proceedings, dated Feb. 10, 2015, in connection with European Patent Application No. 13166988.9, 13 pages.
Response, dated Nov. 27, 2015, to Communication from the Patent Office in connection with European Patent Application No. 13166988.9, 65 pages.
Communication from the Patent Office, dated Nov. 30, 2015, in connection with European Patent Application No. 13166988.9, 1 page.
Intention to Grant, dated Dec. 22, 2015, in connection with European Patent Application No. 13166988.9, 7 pages.
Extended European Search Report, dated Aug. 3, 2016, in connection with European Patent Application No. 16172826.6, 13 pages.
Office Action, dated May 28, 2013, in connection with Korean Patent Application No. 10-2008-701-6352 [English translation and original document in Korean], 13 pages.
Office Action, dated Aug. 30, 2016, in connection with Korean Patent Application No. 10-2014-7024469 [English translation], 7 pages.
Notice of Preliminary Rejection, dated Jun. 21, 2017, in connection with Korean Patent Application No. 10-2017-7005732 [English translation and original document in Korean], 22 pages.
Response, filed Dec. 21, 2017, to Notice of Preliminary Rejection, dated Jun. 21, 2017, in connection with Korean Patent Application No. 10-2017-7005732 [English instructions, original document as filed in Korean and English translation of amended claims], 55 pages.
Notice of Final Rejection, dated Apr. 30, 2018, in connection with Korean Patent Application No. 10-2017-7005732 [English translation and original document in Korean; Ref. 1 = US 2004/0180849; Ref. 2 = Spinowitz et al., Kidney International 68:1801-1807 (2005); Ref. 3 = KR 10-2005-0070014], 9 pages.
Response, filed May 30, 2018, to Notice of Final Rejection, dated Apr. 30, 2018, in connection with Korean Patent Application No.

(56) References Cited

OTHER PUBLICATIONS 10-2017-7005732 [English instructions, response as filed in Korean and English translation of amended claims], 24 pages.
Letters Patent, issued Sep. 28, 2018, in connection with Korean Patent Application No. 10-2017-7005732 [English translation and original document in Korean], 3 pages.
Notice of Preliminary Rejection, dated Sep. 18, 2018, in connection with Korean Patent Application No. 10-2018-7018660 [English translation and original document in Korean], 11 pages.
International Search Report and Written Opinion, dated Aug. 25, 2016, in connection with International Patent Application No. PCT/US2016/034608, 7 pages.
Corrected Notice of Allowability, dated Nov. 26, 2018, in connection with U.S. Appl. No. 14/683,415, 7 pages.
Letter/Written Disclosure of the Supplemental Information Disclosure Statement, filed herewith on Dec. 21, 2018, 2 pages.
Written Submission of Hoffman Eitle Patent, filed on Nov. 28, 2018, in response to the Summons to Attend Oral Proceedings Pursuant to Rule 115(1) EPC, dated Jun. 5, 2018, in connection with the Opposition to corresponding European Patent No. 1 973 549, 16 pages.
Written Submission of Opponent Pharmacosmos Holding A/S, filed on Nov. 29, 2018, in response to the Summons to Attend Oral Proceedings Pursuant to Rule 115(1) EPC, dated Jun. 5, 2018, in connection with the Opposition to corresponding European Patent No. 1 973 549, 37 pages.
Written Submission of Patent Proprietor Vifor (International) AG, filed Nov. 30, 2018, in response to the Summons to Attend Oral Proceedings Pursuant to Rule 115(1) EPC, dated Jun. 5, 2018, in connection with the Opposition to corresponding European Patent No. 1 973 549, 187 pages.
Written Submission of Opponent Generics (U.K.) Limited, filed on Nov. 30, 2018, in response to the Summons to Attend Oral Proceedings Pursuant to Rule 115(1) EPC, dated Jun. 5, 2018, in connection with the Opposition to corresponding European Patent No. 1 973 549, 6 pages.
Response, filed Dec. 14, 2018, to the Notice of Preliminary Rejection, dated Sep. 18, 2018, in connection with corresponding Korean Patent Application No. 10-2018-7018660 [English instructions, original document as filed in Korean, and English translation of amended claims], 47 pages.
Review Decision, issued Mar. 20, 2017, in connection with the Invalidation Request filed in connection with corresponding Chinese Patent Application No. 200780002006.0 [Machine-generated English translation and original document in Chinese], 51 pages.
Letter/Written Disclosure of the Supplemental Information Disclosure Statement, filed herewith on Apr. 8, 2019, 2 pages.
Declaration by Kathryn Barbara Morris of Griffith Hack, dated Jan. 22, 2019, submitted in connection with the Opposition to Australian Patent Application No. 2016205002 [Exhibits KBM-5, KBM-6, KBM-7, KBM-8 AND KBM-9 appended], 225 pages.
Declaration of Vito Ferro, dated Jan. 29, 2019, submitted in connection with the Opposition to Australian Patent Application No. 2016205002 [Exhibits VF-1, VF-2, VF-3, VF-4, VF-5, VF-6, VF-7, VF-8, VF-9, VF-10, VF-11, VF-12 AND VF-13 appended], 266 pages.
Declaration of Simon David Roger, dated Feb. 27, 2019, submitted in connection with the Opposition by Pharmacosmos Holding A/S to Australian Patent Application No. 2016205002 [Exhibits SDR-01 to SDR-10 appended], 232 pages.
Protest under Section 10 of the Patent Rules, filed on Dec. 5, 2018 by ROBIC, L.L.P., against Canadian Patent Application No. 2,953,964, 42 pages.
Examiner's Report, dated Mar. 13, 2019, in connection with Canadian Patent Application No. 2,953,964, 6 pages.
Written Submission of Opponent Taylor Wessing LLP, submitted Jan. 23, 2019, in connection with the Opposition to European Patent No. 1 973 549, 24 pages.
Written Submission of Patent Proprietor Vifor (International) AG, submitted Jan. 28, 2019, in preparation of the oral proceedings and in response to the submission of Opponent Pharmacosmos Holding A/S, dated Nov. 29, 2018, in connection with the Opposition to European Patent No. 1 973 549, 7 pages.
Information about the result of the Oral Proceedings of Jan. 30, 2019, dated Jan. 31, 2019, in connection with the Opposition to European Patent No. 1 973 549, 1 page.
Interlocutory Decision in Opposition proceedings (Art. 101(3)(a) and 106(2) EPC), dated Feb. 28, 2019, in connection with the Opposition to European Patent No. 1 973 549, 78 pages.
Letter/Written Disclosure of the Supplemental Information Disclosure Statement, filed herewith on Oct. 8, 2019, 7 pages.
Defendant Sandoz Inc.'s Answer, Defenses, and Counterclaims, filed Sep. 11, 2019, to the Complaint for Patent Infringement, filed by Plaintiffs Vifor (International) AG and American Regent, Inc. on Aug. 2, 2019, in connection with U.S. Pat. No. 7,612,109, 7,754,702, 8,895,612 and 9,376,505 [Document 12 appended], 58 pages.
Plaintiffs/Counterclaim Defendants Vifor (International) AG and American Regent, Inc.'s, Answer, filed Sep. 26, 2019, to Defendant Sandoz Inc.'s Counterclaims, filed Sep. 11, 2019, in the U.S. District Court for the District of New Jersey, in connection with U.S. Pat. Nos. 7,612,109, 7,754,702, 8,895,612 and 9,376,505 [Document 13-1 appended], 32 pages.
Plaintiffs/Counterclaim Defendants Vifor (International) AG and American Regent, Inc.'s, Answer, filed Aug. 30, 2019, to Defendant Mylan Laboratories Ltd.'s Counterclaims, filed Jul. 26, 2019, in the U.S. District Court for the District of New Jersey, in connection with U.S. Pat. Nos. 7,612,109, 7,754,702, 8,895,612 and 9,376,505 [Document 31-1 appended], 17 pages.
Order requiring a Statutory Disclaimer for claims 28 and 29 of U.S. Pat. No. 7,754,702, entered Aug. 23, 2019, in connection with PTAB Appeal No. IPR2015-01490, 4 pages.
Patent Owner American Regent, Inc., Preliminary Response, filed Sep. 19, 2019, to the Petition of Pharmacosmos A/S, filed Jun. 14, 2019, in connection with U.S. Pat. No. 8,431,549 (Case No. IPR2019-01142), 29 pages.
Office Action, dated Aug. 30, 2019, in connection with U.S. Appl. No. 16/438,340, 12 pages.
Statement of Grounds and Particulars, dated Sep. 13, 2019, in support of the Notice of Opposition, filed Aug. 13, 2019 by Opponent Pharmacosmos Holding A/S, in connection with Australian Patent Application No. 2016205002 [cited documents D1-D7 appended], 504 pages.
Correspondence, dated Sep. 16, 2019, from IP Australia Oppositions and Hearings, inquiring as to whether the parties wish to file evidence or request an oral hearing, in connection with the Opposition to Australian Patent Application No. 2016205002, 1 page.
Opponent Pharmacosmos Holding A/S's Intentions re Evidence and Request for Oral Hearing, dated Sep. 18, 2019, responsive to IP Australia's Correspondence of Sep. 16, 2019, in connection with Australian Patent Application No. 2016205002, 1 page.
Direction in the Opposition Proceedings, issued Oct. 2, 2019, by IP Australia, in connection with Australian Patent Application No. 2016205002, 1 page.
Response, filed Sep. 13, 2019, to Examiner's Report, dated Mar. 13, 2019, in connection with Canadian Patent Application No. 2,953,964, 253 pages.
Appeal Brief, filed Aug. 28, 2019, further to the Notice of Appeal, filed Jul. 29, 2019, to Notice of Final Rejection, issued Apr. 29, 2019, in connection with Korean Patent Application No. 10-2018-7018660 [English instructions and original document as filed in Korean], 33 pages.
Response, dated Oct. 3, 2019, to Examination Report, dated May 24, 2019, in connection with European Patent Application No. 16172826.6, 19 pages.
Petitioner Pharmacosmos A/S's Reply, dated Oct. 7, 2019, to Patent Owner's Preliminary Response, filed Sep. 19, 2019, in connection with U.S. Pat. No. 8,431,549 (Case No. IPR2019-01142), 13 pages.
Letter/Written Disclosure of the Supplemental Information Disclosure Statement, filed herwith on Jul. 12, 2019, 12 pages.
Certified File History of U.S. Appl. No. 12/787,283 (issued as U.S. Pat. No. 8,431,549), certified on Mar. 27, 2019, 362 pages.
Complaint for Patent Infringement, filed Jun. 20, 2019 in the U.S. District Court for the Northern District of West Virginia, by Plain-

(56) References Cited

OTHER PUBLICATIONS tiffs Vifor (International) AG and American Regent, Inc., against Defendant Mylan Laboratories Ltd., in connection with U.S. Pat. Nos. 7,612,109, 7,754,702, 8,895,612 and 9,376,505 [Exhibits A-D and documents 1-5, 2, 3, 4 and 6 appended], 79 pages.
Complaint for Patent Infringement, filed Jun. 18, 2019 in the U.S. District Court for the District of New Jersey, by Plaintiffs Vifor (International) AG and American Regent, Inc., against Defendant Mylan Laboratories Ltd., in connection with U.S. Pat. Nos. 7,612,109, 7,754,702, 8,895,612 and 9,376,505 [Exhibits A-D, documents 1-5, 1-6 and documents 2 to 6 appended], 82 pages.
Curriculum Vitae of Robert Linhardt, Ph.D., 115 pages.
Declaration of Robert Linhardt, dated Jun. 22, 2015, 29 pages.
Expert Declaration of Robert Linhardt, Ph.D., dated Jun. 13, 2019, 20 pages.
Material Specification Sheet for Dextran T1, retrieved May 27, 2015, 6 pages.
Notice of Paragraph IV Certification, re: Ferric Carboxymaltose, dated May 7, 2019, in connection with U.S. Pat. Nos. 7,612,109, 7,754,702, 8,895,612 and 9,376,505 [referenced WIPO publications and published papers appended], 421 pages.
Patent Assignment recorded at Reel: 048067 Frame: 0271— Assignment and Change of Name from Luitpold Pharmaceuticals, Inc. to American Regent, Inc., execution date Jan. 2, 2019, 6 pages.
Petition for Inter Partes Review of U.S. Pat. No. 8,431,549, submitted by Petitioner Pharmacosmos A/S on Jun. 14, 2019 (Case No. IPR2019-01142), 44 pages.
Voluntary Amendment, filed Apr. 24, 2019, in connection with Australian Patent Application No. 2016205002, 11 pages.
Letter, dated May 20, 2019, from IP Australia, indicating that a Stay of the Opposition to Australian Patent Application No. 2016205002, requested in the Voluntary Amendment filed Apr. 24, 2019, will be granted, 2 pages.
Comments, filed May 21, 2019, by Opponent Pharmacosmos Holding A/S, in response to the Voluntary Amendment, filed Apr. 24, 2019, by Applicant American Reagent, Inc., in connection with the Opposition to Australian Patent Application No. 2016205002, 4 pages.
Response of Opponent Pharmacosmos Holding A/S, filed May 24, 2019, to the intention to grant a stay in the Opposition Proceedings in connection with Australian Patent Application No. 2016205002, dated May 20, 2019, 1 page.
Direction made to stay the Opposition to Australian Patent Application No. 2016205002, dated May 30, 2019, 1 page.
Letter, dated Jun. 3, 2019, from IP Australia, indicating that leave to amend the specification, requested in the Voluntary Amendment filed Apr. 24, 2019, will be granted, in connection with Australian Patent Application No. 2016205002, 1 page.
Examination Report, dated Jun. 15, 2019, in connection with corresponding Australian Patent Application No. 2018202715, 5 pages.
Notice of Appeal, filed by Opponent Pharmacosmos Holding A/S on Apr. 12, 2019, against the Interlocutory Decision, dated Feb. 28, 2019, in connection with the Opposition to European U.S. Pat. No. 1 973 549, 5 pages.
Notice of Appeal, filed by Opponent Teva Pharmaceutical Industries Ltd. on Apr. 23, 2019, against the Interlocutory Decision, dated Feb. 28, 2019, in connection with the Opposition to European Patent No. 1 973 549, 3 pages.
Notice of Appeal, filed by Opponent Taylor Wessing LLP on Apr. 26, 2019, against the Interlocutory Decision, dated Feb. 28, 2019, in connection with the Opposition to European Patent No. 1 973 549, 3 pages.
Notice of Appeal, filed by Opponent STADA Arzneimittel AG on May 2, 2019, against the Interlocutory Decision, dated Feb. 28, 2019, in connection with the Opposition to European Patent No. 1 973 549 [machine-generated English language translation and original document in German], 10 pages.

Notice of Appeal, filed by Opponent Generics [UK] Limited on May 3, 2019, against the Interlocutory Decision, dated Feb. 28, 2019, in connection with the Opposition to European Patent No. 1 973 549, 4 pages.
Notice of Appeal, filed by Opponent Hoffmann Eitle Patent on May 7, 2019, against the Interlocutory Decision, dated Feb. 28, 2019, in connection with the Opposition to European Patent No. 1 973 549, 5 pages.
Notice of Appeal, filed by Patent Proprietor Vifor (International) AG on May 10, 2019, against the Interlocutory Decision, dated Feb. 28, 2019, in connection with the Opposition to European Patent No. 1 973 549, 5 pages.
Statement of Grounds of Appeal, filed by Opponent Teva Pharmaceutical Industries Ltd. on Jul. 2, 2019, further to the Notice of Appeal, filed on Apr. 23, 2019, against the Interlocutory Decision, dated Feb. 28, 2019, in connection with the Opposition to European Patent No. 1 973 549 [D72 appended; D13=WO 2007/081744; D33=U.S. Appl. No. 60/757,119; D2a=U.S. Pat. No. 7,612,109; D2b-WO 2004/037865; D2c=CA 2493806; D3=Marchasin et al. (1964) *Blood* 23(3):354-358; D4=U.S. 2003/0232084; D12= Spinowitz et al. (2005) *Kidney International* 68:1801-1907; and D14=Landry et al. (2005) *American Journal of Nephrology* 25(4):400-410], 18 pages.
Statement of Grounds of Appeal, filed by Opponent Taylor Wessing LLP on Jul. 5, 2019, further to the Notice of Appeal, filed on Apr. 26, 2019, against the Interlocutory Decision, dated Feb. 28, 2019, in connection with the Opposition to European Patent No. 1 973 549 [D64-Extract of MHRA Public Assessment Report for Ferinject® 50mg iron/ml solution for injection/infusion; D9=Speech given by Dr. Barbara von Eisenhart-Rothe at Galenica Press Conference 5005 on Apr. 12, 2005, Subject: "Clinical Development Programme of VIT-45;" D9d-U.S. 2006/0116349; D9e=Manley and McClaran (2006) *Int. J. Artif. Organs* 29(11):1062-1066; D27=Seid et al. (2006) *Blood* 108(11):3739; D59=Copy of Seid et al. (2006) *Blood* 108(11):3739 with a public availability date stamp; D2a=U.S. Pat. No. 7,612,109; D2b=WO 2004/037865; D2c=CA 2493806; D1=U. S. Pat. No. 3,639,588; and D32=U.S. 2004/0180849], 18 pages.
Statement of Grounds of Appeal, filed by Opponent Generics [UK] Ltd. on Jul. 8, 2019, further to the Notice of Appeal, filed on May 3, 2019, against the Interlocutory Decision, dated Feb. 28, 2019, in connection with the Opposition to European Patent No. 1 973 549 [D27=Seid et al. (2006) *Blood* 108(11):3739; D2a=U.S. Pat. No. 7,612,109; D1=U.S. Pat. No. 3,639,588; D3=Marchasin et al. (1964) *Blood* 23(3):354-358; D5=Preusser et al. (2005) *Clin. Expr. Pharmacol. Physiol.* 32:1020-1026; and D32=U.S. 2004/0180849], 11 pages.
Notice of Final Rejection, dated Apr. 29, 2019, in connection with Korean Patent Application No. 10-2018-7018660 [English translation and original document in Korean; Ref. 1= U.S. 2004/0180849; Ref. 2= Spinowitz et al. (2005) *Kidney International* 68:1801-1807], 8 pages.
Motion to Stay the Second-Filed Suit in the Northern District of West Virginia against Defendant Mylan Laboratories Ltd., filed on Jul. 10, 2019 by Plaintiffs Vifor (International) AG and American Regent, Inc., in in connection with U.S. Pat. Nos. 7,612,109, 7,754,702, 8,895,612 and 9,376,505 [Exhibits 1-7 appended], 148 pages.
Letter/Written Disclosure of the Supplemental Information Disclosure Statement, filed herewith on Aug. 23, 2019, 10 pages.
Complaint for Patent Infringement, filed Aug. 2, 2019 in the U.S. District Court for the District of New Jersey, by Plaintiffs Vifor (International) AG and American Regent, Inc., against Defendant Sandoz Inc., in connection with U.S. Pat. Nos. 7,612,109, 7,754,702, 8,895,612 and 9,376,505 [Exhibits A-D, and documents 1-5 and 1-6 appended], 78 pages.
Mylan Laboratories Ltd.'s Answer, Separate Defenses, and Counterclaims to Vifor (International) AG and American Regent, Inc.'s Complaint, filed Jul. 26, 2019 in the U.S. District Court for the District of New Jersey, in connection with U.S. Pat. Nos. 7,612,109, 7,754,702, 8,895,612 and 9,376,505 [Documents 16-1 and 17 appended], 31 pages.
Order Granting Plaintiffs' Unopposed Motion to Stay the Second-Filed Suit in the Northern District of West Virginia and Staying the

(56) References Cited

OTHER PUBLICATIONS

Case, dated Jul. 26, 2019, in connection with U.S. Pat. Nos. 7,612,109, 7,754,702, 8,895,612 and 9,376,505, 2 pages.
Notice of Opposition, filed Aug. 13, 2019, by Opponent Pharmacosmos Holding A/S, to the allowance of the amendment to Australian Patent Application No. 2016205002, filed Apr. 24, 2019, 2 pages.
Withdrawal of Appeal, filed by Opponent STADA Arzneimittel AG on Jul. 10, 2019, in connection with the Opposition to European Patent No. 1 973 549 [machine-generated English language translation and original document in German], 6 pages.
Statement of Grounds of Appeal, filed by Patent Proprietor Vifor (International) AG on Jul. 10, 2019, further to the Notice of Appeal, filed on May 10, 2019, against the Interlocutory Decision, dated Feb. 28, 2019, in connection with the Opposition to European Patent No. 1 973 549, 231 pages.
Communication pursuant to Article 94(3) EPC (Examination Report), dated May 24, 2019, in connection with European Patent Application No. 16172826.6 [D3=WO 2004/037865; D8=MacDougall, I.C. (1999) *Kidney International* 55(69):S61-66; and D13=Fishbane, S. (2003) *Am. J. Kidney Dis.* 41(6 Suppl 5):S18-S26], 5 pages.
Letter/Written Disclosure of the Supplemental Information Disclosure Statement for the above-referenced application, filed Jan. 22, 2020, 15 pages.
Joint Status Report, filed Jan. 7, 2020 in the U.S. District Court for the Northern District of West Virginia, by Plaintiffs Vifor (International) AG and American Regent, Inc., and Defendant Mylan Laboratories Ltd., in connection with U.S. Pat. Nos. 7,612,109, 7,754,702, 8,895,612 and 9,376,505, 3 pages.
Order Requiring a Showing of Good Cause Why Claim 15 Should Not Be Deemed Unpatentable, entered Dec. 18, 2019, in connection with U.S. Pat. No. 8,431,549 (IPR2015-01493), 5 pages.
Patent Owner Exhibit List as of Jan. 6, 2020, in connection with U.S. Pat. No. 8,431,549 (IPR2015-01493) [Exhibits 2128-2130 appended], 15 pages.
Patent Owner's Response to Order Requiring a Showing of Good Cause Why Claim 15 Should Not Be Deemed Unpatentable, filed Jan. 6, 2020, in connection with U.S. Pat. No. 8,431,549 (IPR2015-01493), 12 pages.
Petitioner Pharmacosmos A/S's Updated Exhibit List as of Jan. 6, 2020, in connection with U.S. Pat. No. 8,431,549 (IPR2015-01493), 6 pages.
Petitioner Pharmacosmos A/S's Response to Order Requiring a Showing of Good Cause Why Claim 15 Should Not Be Deemed Unpatentable, filed Jan. 6, 2020, in connection with U.S. Pat. No. 8,431,549 (IPR2015-01493), 7 pages.
Decision Denying Institution of *Inter Partes* Review, entered Dec. 18, 2019, in connection with U.S. Pat. No. 8,431,549 (IPR2019-01142), 17 pages.
Letter, dated Jan. 3, 2020, stating that Applicant does not wish to rely on evidence in answer, in connection with the Opposition to corresponding Australian Patent Application No. 2016205002, 1 page.
Letter, dated Jan. 15, 2020, from IP Australia, requesting confirmation that a hearing is required, in connection with corresponding Australian Patent Application No. 2016205002, 1 page.
Applicant Response, dated Jan. 16, 2020, to the Letter from IP Australia, dated Jan. 15, 2020, in connection with corresponding Australian Patent Application No. 2016205002, 1 page.
Opponent Pharmacosmos Holding A/S's Request for Hearing, dated Jan. 21, 2020, responsive to IP Australia's Letter of Jan. 15, 2020, in connection with corresponding Australian Patent Application No. 2016205002, 2 pages.
Petition for Post Grant Review of U.S. Pat. No. 10,478,450, filed by Petitioner Pharmacosmos A/S Jan. 6, 2020, Exhibits 1001-1105 appended (Part 1 of 6, pp. 1-688 of 2977 pages).
Petition for Post Grant Review of U.S. Pat. No. 10,478,450, filed by Petitioner Pharmacosmos A/S Jan. 6, 2020, Exhibits 1001-1105 appended (Part 2 of 6, pp. 689-1213 of 2977 pages).
Petition for Post Grant Review of U.S. Pat. No. 10,478,450, filed by Petitioner Pharmacosmos A/S Jan. 6, 2020 (Case No. PGR2020-00009), Exhibits 1001-1105 appended (Part 3 of 6, pp. 1214-1526 of 2977 pages).
Petition for Post Grant Review of U.S. Pat. No. 10,478,450, filed by Petitioner Pharmacosmos A/S Jan. 6, 2020 (Case No. PGR2020-00009), Exhibits 1001-1105 appended (Part 4 of 6, pp. 1527-1934 of 2977 pages).
Petition for Post Grant Review of U.S. Pat. No. 10,478,450, filed by Petitioner Pharmacosmos A/S Jan. 6, 2020 (Case No. PGR2020-00009), Exhibits 1001-1105 appended (Part 5 of 6, pp. 1935-2230 of 2977 pages).
Petition for Post Grant Review of U.S. Pat. No. 10,478,450, filed by Petitioner Pharmacosmos A/S Jan. 6, 2020 (Case No. PGR2020-00009), Exhibits 1001-1105 appended (Part 6 of 6, pp. 2231-2977 of 2977 pages).
Letter/Written Disclosure of the Supplemental Information Disclosure Statement for the above-referenced application, filed herewith on Dec. 6, 2019, 5 pages.
Statutory Disclaimer in U.S. Pat. No. 7,754,702 for claims 28 and 29, dated Sep. 9, 2019, in connection with PTAB Appeal No. IPR2015-01490, 3 pages.
Certificate of Correction in U.S. Pat. No. 7,754,702, dated Oct. 8, 2019, 1 page.
*Inter Partes* Review Certificate, issued Nov. 18, 2019, in connection with PTAB Case No. IPR2015-01490, 2 pages.
Sur-Reply, filed Oct. 15, 2019, to Petitioner's Reply to Patent Owner's Preliminary Response, dated Oct. 7, 2019, in connection with U.S. Pat. No. 8,431,549 (Case No. IPR2019-01142), 17 pages.
Office Action, dated Nov. 12, 2019, in connection with U.S. Appl. No. 15/958,930, 16 pages.
Response, filed Oct. 10, 2019, to Office Action, dated Aug. 30, 2019, in connection with U.S. Appl. No. 16/438,340, 7 pages.
Notice of Allowance, dated Nov. 25, 2019, in connection with U.S. Appl. No. 16/438,340, 9 pages.
Direction in the Opposition Proceedings, dated Nov. 4, 2019, by IP Australia, in connection with corresponding Australian Patent Application No. 2016205002, 1 page.
Protest under Section 12 of the Patent Rules, filed Nov. 14, 2019, by ROBIC, L.L.P., against corresponding Canadian Patent Application No. 2,953,964 [cited documents D9-D13 appended], 247 pages.
Letter, dated Nov. 26, 2019, from the Canadian Intellectual Property Office, advising Applicant of a Protest, in connection with corresponding Canadian Patent Application No. 2,953,964, 3 pages.
Imferon® Package Insert, 1988, 1989, 2 pages.
INFeD® (IRON DEXTRAN INJECTION, (USP) Package Insert, Sep. 1996, 2 pages.
INJECTAFER® Orange Book: Approved Drug Products with Therapeutic Equivalence Evaluations Excerpts, Mar. 6, 2015, 4 pages.
INJECTAFER® (ferric carboxymaltose injection), for intravenous use, Highlights of Prescribing Information, Revised Apr. 2018, 4 pages.
IPR2015-01490 in connection with U.S. Pat. No. 7,754,702, Notice of Filing Date Accorded to Petition and Time for Filing, Patent Owner Preliminary Response, Paper No. 4, dated Jul. 10, 2015, 3 pages.
IPR2015-01490 in connection with U.S. Pat. No. 7,754,702, Decision, Paper No. 11, entered Jan. 8, 2016, 20 pages.
IPR2015-01490 in connection U.S. Pat. No. 7,754, Erratum, Paper No. 13, entered Jan. 21, 2016, 3 pages.
IPR2015-01490 in connection with U.S. Pat. No. 7,754,702, Final Written Decision, Paper No. 54, filed Jan. 4, 2017, 52 pages.
IPR2015-01490 in connection with U.S. Pat. No. 7,754,702, Order Conduct of the Proceeding, Paper No. 57, entered Aug. 23, 2019, 4 pages
IPR2015-01490 in connection with U.S. Pat. No. 7,754,702 and IPR2015-01493 in connection with U.S. Pat. No. 8,431,549, Amendment to Scheduling Order, Paper No. 17, entered Feb. 17, 2016, 3 pages.
IPR2015-01490 in connection with U.S. Pat. 7,754,702; IPR2015-01493 in connection with U.S. Pat. No. 8,431,549; and IPR2015-01495 in connection with U.S. Pat. No. 8,895,612, Order Conduct of the Proceedings, Paper No. 8, entered Oct. 14, 2015, 4 pages.

(56) References Cited

OTHER PUBLICATIONS

IPR2015-01490 in connection with U.S. Pat. No. 7,754,702 and IPR2015-01493 in connection with U.S. Pat. No. 8,431,549, Order Conduct of the Proceeding, Paper No. 21, entered Mar. 11, 2016, 6 pages.
IPR2015-01490 in connection with U.S. Pat. No. 7,754,702 and IPR2015-01493 in connection with U.S. Pat. No. 8,431,549, Order Conduct of the Proceeding, Paper No. 45, Entered Aug. 19, 2016, 3 pages.
IPR2015-01490 in connection with U.S. Pat. No. 7,754,702 and IPR2015-01493 in connection with U.S. Pat. No. 8,431,549, Order Trial Hearing, Paper No. 46, Dated Aug. 22, 2016, 5 pages.
IPR2015-01490 in connection with U.S. Pat. No. 7,754,702 and IPR2015-01493 in connection with U.S. Pat. No. 8,431,549, Record of Oral Hearing, Paper No. 53, Nov. 3, 2016, 104 pages.
IPR2015-01490 in connection with U.S. Pat. No. 7,754,702 and IPR2015-01493 in connection with U.S. Pat. No. 8,431,549, Scheduling Order, Paper No. 12, entered Jan. 8, 2016, 7 pages.
IPR2015-01490 in connection with U.S. Pat. No. 7,754,702 and IPR2015-01493 in connection with U.S. Pat. No. 8,431,549, Order Conduct of Proceeding, Paper No. 22, entered Mar. 11, 2016, 6 pages.
IPR2015-01493 in connection with U.S. Pat. No. 8,431,549, Notice of Filing Date Accorded to Petition and Time for Filing Patent Owner Preliminary Response, Paper No. 4, mailed Jul. 10, 2015, 3 pages.
IPR2015-01493 in connection with U.S. Pat. No. 8,431,549, Decision Institution of Inter Partes Review, Paper No. 11, entered Jan. 8, 2016, 24 pages.
IPR2015-01493 in connection with U.S. Pat. No. 8,431,549, Decision Denying Petitioner's Request for Rehearing, Paper No. 21, entered Feb. 26, 2016, 5 pages.
IPR2015-01493 in connection with U.S. Pat. No. 8,431,549, Final Written Decision, Paper No. 54, filed Dec. 28, 2016, 28 pages.
IPR2015-01493 in connection with U.S. Pat. No. 8,431,549, Panel Change Order, Paper No. 56 entered Dec. 18, 2019, 3 pages.
IPR2015-01493 in connection with U.S. Pat. No. 8,431,549, Order Conduct of the Proceeding—Requiring a Showing of Good Cause Why Claim 15 Should Not Be Deemed Unpatentable, Paper No. 57 entered Dec. 18, 2019, 5 pages.
IPR2015-01493 in connection with U.S. Pat. No. 8,431,549, Order Conditionally Granting Petitioner's Unopposed Motion to Withdraw and Substitute Counsel, Paper No. 59 entered Dec. 23, 2019, 4 pages.
IPR2015-01495 in connection with U.S. Pat. No. 8,895,612, Notice of Filing Date Accorded to Petition and Time for Filing Patent Owner Preliminary Response, Paper No. 4, mailed Jul. 10, 2015, 3 pages.
IPR2015-01495 in connection with U.S. Pat. No. 8,895,612, Decision Denying Institution of Inter Partes Review, Paper No. 11, entered Jan. 8, 2016, 23 pages.
IPR2019-01142 in connection with U.S. Pat. No. 8,431,549, Notice of Filing Date Accorded to Petition and Time for Filing Patent Owner Preliminary Response, Paper No. 3, mailed Jun. 19, 2019, 5 pages.
IPR2019-01142 in connection with U.S. Pat. No. 8,431,549, Order Granting Petitioner's Motions for Pro Hac Vice Admission of Vanessa Park-Thompson and Ryan P. Johnson, Paper No. 9, entered Sep. 18, 2019, 4 pages.
IPR2019-01142 in connection with U.S. Pat. No. 8,431,549, Decision Denying Institution of Inter Partes Review, Paper No. 13, entered Dec. 18, 2019, 17 pages.
Iron Sorbitol Injection, British Pharmacopeia Omitted Monograph, unknown date, 4 pages.
Issue Notification and other documents related to the prosecution of U.S. Pat. No. 8,431,549, 244 pages.
Issue Notification and other documents related to the prosecution of U.S. Pat. No. 8,895,612, 237 pages.
IV Iron Products, Iron Corner pamphlet, Nov. 2013, 3 pages.

Geisser, Safety and Efficacy of Iron(III)-hydroxide Polymaltose Complex, Drug Research, 2007, 57 (6a): 439-452.
Geissler, et al, The Pharmacokinetics and Pharmacodynamics of Iron Preparations, Pharmaceutics 2001, 3, 12-33.
Geisser, et al., Issue Notification and Portions of file wrapper of U.S. Pat. No. 9,376,505, (dated Jun. 28, 2016) pp. 1-346.
Groman, et al. Certificate Extending Patent Term for U.S. Pat. No. 6,599,498, pp. 1-144 (Mar. 26, 2014).
Royal Perth Hospital, Guidelines for administration of IV iron polymaltose in chronic kidney disease via continuous intravenous infusion, 3 pages (2002).
Journal of the America Society of Nephrology, vol. 14, 2003, p. 705A.
Jacobs, Peter et al., Comparative Bioavailability of Ferric Polymaltose and Ferrous Sulphate In Iron-Deficient Blood Donors, Journal of Clinical Apheresis, vol. 8, Issue 2, 1993, pp. 89-95.
Jankiewicz Barbara, et al., The Influence of molar mass of oligosaccharides on their ability to disperse iron hydroxide (III)., Acta Poloniae Pharmaceutica Dec. 31, 1993, 51(2):187-189.
Jankiewicz Barbara, et al., Complexing of Iron (III) Hydroxide With Polymaltose and Products of Its Electrochemical Oxidation, Acta Poloniae Pharmaceutica vol. 6, 1988, pp. 517-522.
Jankiewicz Barbara, et al., Electrochemical Oxidation of Low Molecular Dextran, Chemia Stosowana, XXXII, 2, 293-299, 1988.
Jayaseean, T., et al, Cost Comparison, Efficacy and Safety of Intravenous Iron Infusion Versus Push In Maintenance Haemodialysis Patients In A Tertiary Care Centre, Indian Journal of Nephrology, 2005; 15: 232-234.
Jeanes, Allene, Molecular Association In Dextran and In Branched Amylaceouscarbohydrates, J. Biol. Chem. 1948 176: 617-.
Johnson, Glynis, et al., Bioavailability and the Mechanisms of Intestinal Absorption of Iron from Ferrous Ascorbate and Ferric Polymaltose in Experimental Animals, Exp. Hematol. 18:1064-1069 (1990) International Society for Experimental Hematology.
United States Patent and Trademark Office Before The Patent Trial And Appeal Board *Pharmacosmos A/S*, Petitioner, V. *American Regent, Inc.*, Patent Owner Case IPR2019-01142 U.S. Pat. No. 8,431,549 Declaration of Ryan P. Johnson In Support Of Petitioner Pharmacosmos A/S's Motion For Admission PRO HAC VICE IPR2019.
Resume/CV of Lee Josephson, 139 Oak Street Reading, MA 01867.
United Stated Patent and Trademark Office Before The Patent Trial And Appeal Board *Pharmacosmos A/S*, Petitioner, V. *American Regent, Inc.*, Patent Owner. U.S. Pat. No. 10,478,450 Declaration Of Lee Josephson, PH.D.
Dahdah, Khalil, et al. "Intravenous Iron Dextran Treatment in Predialysis Patients with Chronic Renal Failure," Amer. J. of Kidney Diseases, vol. 36, No. 4, Oct. 2000, pp. 775-782.
Danielson, Bo G., et al. Iron Therapy with Special Emphasis on Intravenous Administration. First Ed. 1996 Vifor (International) Inc. ISBN 3-85819-223-6.
Data Sheet—Ferrosig. From Medsafe—New Zealand Medicines and Medical Devices Safety Authority. Feb. 16, 2010, from Internet URL: www.medsafe.govt.nz/profs/datasheet/f/ferrosiginj.htm.
de Belder, A.N. Dextran. Amersham Biosciences, Ed. AA. 2003.
de Nooy, Arjan, et al. "On the Use of Stable Organic Nitroxyl Radicals for the Oxidation of Primary and Secondary Alcohols," Synthesis. Oct. 1996.
Dreary, Michael E., et al. "Evidence for Cyclodextrin Dioxiranes," Carbohydrate Research, vol. 309, Apr. 17, 1998, pp. 17-29.
Decision Summary for Ferrlecit: Intravenous Iron Therapy (CAG-00046N) Jul. 9, 2019.
DeMaeyer, E.M., et al. Preventing and Controlling Iron Deficiency Anemia Through Primary Health Care. World Health Organization, Geneva. 1989.
"Dextran I." United States Pharmacopeia—National Formulary. Official Compendia of Standards. 23rd Ed. Jan. 1, 2005.
Dextran TI Technical Quality. Pharmacosmos A/S. May 27, 2015.
O'Neill, Maryadele J., et al. "Dextranase," The Merck Index: Encyclopedia of Chemicals, Drugs and Biologicals, 14th Ed. Merck & Co. Inc. New Jersey 2006.
Dixon, H.B.F. "Polysaccharide Nomenclature" Pure & Appl. Chem. vol. 54, No. 8, 1982, pp. 1523-1526.

(56) References Cited

OTHER PUBLICATIONS

Dokic, P. et al. "Molecular characteristics of maltodextrins and rheological behavior of diluted and concentrated solutions," Colloids and Surfaces A: Physiochemical and Engineering Aspects. vol. 141, 1998, 435-440.
Dresch, et al. "Comparison due Metabolisme de Deux Preparations de Fer Injectable," "Blood Cells" Nouvelle Revue Francaise d'Hemotologie. vol. 16, No. 1, Jun. 1976.
Driss, F., et al. "Effects of Intravenous Polymaltose Iron on Oxidate Stress and Non-Transferrin Bound Iron in Hemodialysis Patients,"Nephron Clin. Pract. 2005: 99: c63-c67.
"Polimaltosa Ferrica—Iron Polymaltose,"Medicamentos para Veterinaria—Medicamentos de Actualidad—Drugs of Today—vol. 12, No. 10, 1976.
Eriksson, Hans, et al. "Pharmacological Studies on a Iron-poly (sorbitol-gluconic acid) Complex for Parenteral Treatment of Iron Deficient Anemia,"Scand J Haemotol (1977) Suppl 32; 38-49.
"Iron overload: Molecular clues to its cause" Frontlines. TIBS-24, May 1999.
Ersoy, H., et al. "Original Report: Blood Pool MR Angiography of Aortic Stent-Graft Endoleak" Amer J Roentgenology, vol. 182, No. 5, May 2004.
Esposito, B. P., et al. "Labile iron parenteral iron formulations and its potential for generating plasma nontransferrin bound iron in dialysis patients," Eur J Clin Investigation, vol. 32, Supp. 1, 2002.
CosmoFer 50 mg/ml package insert, Rev. Mar. 10, 2005.
"Experience with the use of an iron polymaltose (dextran) complex given by single total dose infusion to stable chronic haemodialysis patients" Google search results. Oct. 7, 2015.
Crichton, Robert R., et al. "Chapter 7. Iron Therapy," Iron Therapy with Special Emphasis on Intravenous Administration. UniMed 2017.
"Rules and Regulations," Federal Registry vol. 34 No. 31, Feb. 14, 1969, Washington DC, pp. 2173-2235.
FDA Drug Safety Communications—Safety Announcement "FDA strengthens warning and changes prescribing instructions to decrease risk of serious allergic reactions with anemia drug Feraheme (ferumoxytol)" Mar. 30, 2015.
Feraheme ferumoxytol injection package insert. Rv. Mar. 2015. AMAG Pharmaceuticals, Waltham, MA.
Ferinject (ferric carboxymaltose) 50 mg iron/ ml solution for injection/infusion. Vifor France SA. Jun. 2012.
"Iron Corner: IV Iron Products," Society for Advancement of Blood Management, Inc., Englewood, NJ, Nov. 2013, URL: www.iron.sabm.org.
Ferrlecit package insert NDA 20-955/S-003 Watson Pharmaceuticals Inc and R & D Laboratories Inc., 2001.
Fessenden, Ralph J., et al. "Carbohydrates" Organic Chemistry, 6th Ed. 1998 Brooks/Cole Publishing, Pacific Grove, CA.
Fielding, J. "Intravenous Iron Dextrin in Iron Deficient Anaemia," New Intramuscular Haematinic. Jul. 29, 1961, pp. 279-284.
Fishbane, S., et al. "The comparative safety of intravenous iron dextran, iron saccharate and sodium ferric gluconate," Comparative Safety of IV, Nov./Dec. 2000, pp. 382-386.
Fishbane, S. et al. "Sodium ferric gluconate complex in the treatment of iron deficiency in patients on dialysis," Amer J Kidney Diseases, vol. 37, No. 5, May 2001.
Fleming, L. et al. "Dextran antibodies, complement conversion and circulating immune complexes after intravenous iron dextran therapy in dialysed patients," Nephrol. Dial. Transplants, vol. 7 (1992) pp. 35-39.
Floor, M., et al. "Preparations and calcium complexation of oxidized polysaccharides," Starch/starke, vol. 41, No. 9, 1989, pp. 348-354.
Frank, Michael, M., et al. "Chapter 58: Immune Complexes and Allergic Disease," Middleton's Allergy: Principles and Practice, 6th Ed., vol. 2., 2003, ISBN 0-323-014259.
Frankenfield, D., et al. "Anemia management of adult hemodialysis patients in the US: Results from the 1997 ESRD Core Indicators Project," Kidney International, vol. 57 (2000) pp. 578-589.
Crichton, Robert R., et al. "Chapter 3. Laboratory Evaluation of Iron Status," Iron Therapy with Special Emphasis on Intravenous Administration. UniMed 2008.
"Preisermassigung," Praxis, No. 22, Jun. 1950.
"Definitions" Webster's Ninth New Collegiate Dictionary. Merriam Webster Inc. 1986.
Excerpts from Merriam Webster's Collegiate Dictionary, 11th Ed. 2005 Merriam Webster Inc., pp. 864, 961.
File Wrapper, U.S. Appl. No. 13/847,254, filed Mar. 19, 2013, first named inventor Helenek.
Excerpt from European Journal of Haemotology, vol. 98, No. 3, Mar. 2017.
Complaint for Patent Infringement, filed Feb. 7, 2020 in the U.S. District Court for the District of New Jersey, 3:20-cv-01350-BRM-LHG, by Plantiff American Regent, Inc., against Defendant Pharmacosmos Therapeutics Inc. and Pharmacosmos A/S, in connection with U.S. Pat. Nos. 8,431,549 and 10,478,450 [Exhibits 1-13, and documents 1-5], 138 pages.
Corporate Disclosure Statement of Plaintiff American Regent, Inc. for Patent Infringement, filed Feb. 7, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 1 page.
Report on the Filing or Determination of an Action regarding a Patent or Trademark for Patent Infringement, filed Feb. 7, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 1 page.
Summons for Patent Infringement, filed Feb. 7, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 2 pages.
Notice of Appearance of J. Brugh Lower on behalf of American Regent, Inc., filed Feb. 20, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 1 page.
Notice of Appearance of Guillermo Carlo Artiles on behalf of Pharmacosmos A/S, Pharmacosmost Therapeutics Inc., filed Feb. 21, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 2 pages.
Notice of Appearance of Omar A. Bareentto on behalf of Pharmacosmos A/S, Pharmacosmost Therapeutics Inc., filed Feb. 21, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 2 pages.
Letter from William P. Deni, Jr. to the Honorable Brian R. Martinotti, U.S.D.J. re: Proposed Stipulation and Order, filed Feb. 21, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450 [Document 1], 4 pages.
Stipulation and Order, filed Feb. 24, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 3 pages.
Docket Report List Transaction Receipt, retrieved Mar. 25, 2020 in the U.S. District Court for the District of New Jersey, 3:20-cv-01350-BRM-LHG, by Plaintiff American Regent, Inc., against Defendant Pharmacosmos Therapeutics Inc. and Pharmacosmos A/S, in connection with U.S. Pat. Nos. 8,431,549 and 10,478,450, 3 pages.

(56) References Cited

OTHER PUBLICATIONS

Auerbach, Michael, et al. "Intravenous Iron Optimizes the Response to Recombinant Human Erythropoietin in Cancer Patients With Chemotherapy-Related Anemia: A Multicenter, Open-Label, Randomized Trial" Journal of Clinical Oncology, vol. 22, No. 7 (Apr. 1, 2004).

Coe, Emma M., et al. "An Investigation into the Size of an Iron DextranComplex," Journal of Inorganic Chemistry, vol. 60, No. 2, 1995, pp. 149-153.

Code of Federal Regulation (21 CFR § 184.144) 2002.

Danielson, Bo G. "Structure, Chemistry, and Pharmacokinetics of Intravenous Iron Agents" J Am Soc Nephrol, vol. 15; S93-S98, 2004.

Funk, Felix, et al. "Physical and Chemical Characterization of Therapeutic Iron Containing Materials: A Study of Several Superparamagnetic Drug Formulations with the β-FeOOH or Ferrihydrite Structure," Hyperfine Interactions 36; pp. 73-95, 2001.

Geisser, P., et al. "Investigation on the Dosage/Efficacy Relationship of Iron Dextran in Veal Calves," Therapeutics for States of Deficiency. Arzneim-Forsch/Drug Res. 41 (I), No. 1 (1991).

Geisser, P., et al. "Structure/Histotoxicity Relationship of Parenteral Iron Preparations" Therapeutics for States of Deficiency. Arzneim-Forsch/Drug Res. 42 (II), No. 12 (1992).

Jahn, M.R., et al. "A Comparative Study of the Physicochemical Properties of Iron Isomaltoside 1000 (Monofer®), a New Intravenous Iron Preparation and Its Clinical Implications" European Journal of Pharmaceutics and Biopharmaceutics 78 (2011) 480-491.

Neiser, Susann, et al. "Physico-Chemical properties of the new generation IV iron preparations ferumoxytol, iron isomaltoside 1000 and ferric carbxoymaltose," Biometals (2015) 28:615-635.

Perkins, John J. Principles and Methods of Sterilization in Health Sciences. Charles C Thomas Pub Limited, 1983.

Singh, K., et al. "A comparison between intravenous iron polymaltose complex (Ferrum Hausmann®) and oral ferrous fumarate in the treatment of iron deficiency anaemeia in pregnancy" Eur J Haematol, Feb. 1998;60(2):119-24.

Spinowitz, B.S., et al. "The Safety and Efficacy of Ferumoxytol Therapy in Anemic Chronic Kidney Disease Patients," Kidney International, 2005, vol. 68, pp. 1801-1807.

United States District Court, District of New Jersey. Defendants' Invalidity Contentions Regarding U.S. Pat. Nos. 7,612,109, 7,754,702, 8,895,612, 9,376,505, and 10,519,252 Made Under Local Patent Rules 3.3 and 3.6 [Redacted]; *VIFOR (International) AG and American Regent, Inc.*, Plaintiffs, v. *Mylan Laboratories Ltd. and Sandoz Inc.*, Defendants. (FLW) (DEA).

Hartsfield, J, Iron Status in the Female Blood Donor, Nutrition Bytes, 4 (1), 1998, pp. 1-6.

Umeki, K et al Structures of Multi-Branched Dextrins Produced by Saccharigying alpha-Amylase from Starch J. Biochem., 78, 897-903 (1975).

U.S. Court of Appeals Federal Circuit Judgement Affirmed in *Luitpold Pharmaceuticals, Inc.*, Appellant v. *Pharmacosmos A/S*, Cross-Appellant 2017-1715, 2017-1725 PR2015-01490, IPR2015-01493 (Apr. 12, 2018) 2 pages.

U.S. Court of Appeals Federal Circuit Mandate Issued in *Luitpold Pharmaceuticals, Inc.*, Appellant v. *Pharmacosmos A/S*, Cross-Appellant 17-1715, 17-1725 IPR2015-01490, IPR2015-01493 (May 21, 2018) 1 page.

U.S. Court of Appeals Federal Circuit Notice of Entry of Judgement without Opinion Issued in *Luitpold Pharmaceuticals, Inc.*, Appellant v. *Pharmacosmos A/S*, Cross-Appellant 17-1715, 17-1725, 17-1786 IPR2015-01490, IPR2015-01493 (Apr. 12, 2018) 1 page.

USPNF, Dextran Official Monographs, 601-606 (2005).

Declaration of Linhardt, Robert Filed on behalf of Pharmacosmos A/S, IPR2019-01142, Jun. 22, 2015, pp. 1-29 for U.S. Pat. No. 8,895,612.

USPNF, Maltodextrin Official Monographs, 2577-2579 (2002).

USPNF, Maltodextrin Official Monographs, 2789-2791 (2003).

United States Patent and Trademark Office Before The Patent Trial and Appeal Board *Pharmacosmos A/S*, Petitioner, v. *Luitpold Pharmaceuticals, Inc.*, Patent Owner. Case IPR2015-01493 (U.S. Pat. No. 8,431,549 B2) Objections to Petitioner's Reply and Opposition Evidence dated Jun. 27, 2016.

United States Patent and Trademark Office Non-Final Office Action, dated Oct. 23, 2008, U.S. Appl. No. 11/620,986, filed Jan. 8, 2007, First Named Inventor: Mary Jane Helenek.

United States Patent and Trademark Office Non-Final Office Action, dated Mar. 23, 2012, U.S. Appl. No. 12/787,283, filed May 25, 2010, First Named Inventor: Mary Jane Helenek.

United Stated Patent and Trademark Office Non-Final Office Action, dated Feb. 7, 2014, U.S. Appl. 14/100,717, filed Dec. 9, 2013, First Named Inventor: Mary Jane Helenek.

The Merck Index—An Encyclopedia of Chemicals, Drugs, and Biologicals, Fourteenth Edition, Maryadele J. O'Neil, Editor, Merck & Co., Inc. Whitehouse Station, NJ, USA 2006, Library of Congress Catalog Card Number 89-60001, ISBN Number 0-911910-00-X, ISB Number 978-0-911910-00-1, Dextranase—2949-2950.

Erni, I., et al., Chemical Characterization of Iron (111)-Hydroxide-Dextrin Complexes, A comparative study of commercial preparation with alleged reproductions used in the examination of bioavailability Arzeimittel Forschung/Drug Res. 34 (II), Nr. II (1984) 1555-1559.

Owens III, Donald E., et al., Opsonization, Biodistribution, And Pharmacokinetics of Polymeric Nanoparticles, International Journal of Pharmaceutics, 307 (2006) 93-102.

van Zyl-Smit, R., et al., "Experience with the Use of an Iron Polymaltose (Dextrin) Complex Given by Single Total Dose Infusion to Stable Chronic Haemodialysis Patients," Nephron 92, 2002, pp. 316-323.

van Zyl-Smit, R., et al., "Experience with the Use of an Iron Polymaltose (Dextrin) Complex Given by Single Total Dose Infusion to Stable Chronic Haemodialysis Patients," Nephron, 2002, Web printout, 4 pages.

Vannotti, A., chairman of Colloquia Geigy on "Iron Deficiency, Pathogenesis-Clinical aspects-Therapy," 1970, 648 pages.

Weiss, G., et al., "Anemia of Chronic Disease," N Engl. J. Med. 352, Mar. 10, 2005, pp. 1011-1023.

White, Jr., D.R., et al., "Dextrin characterization by high-performance anion-exchange chromatography-pulsed amperometric detection and size-exclusion chromatography-multi-angle light scattering-refractive index detection," Journal of Chromatography A, 997 (2003) pp. 79-85.

Wikstrom, B., et al., "Iron isomaltoside 1000: a new intravenous iron for treating iron deficiency in chronic kidney disease," J NephroL 2011; 24 (05), pp. 589-596.

Woodman, J., et al., "A Surveillance Programme on a Long-established Product:Imferon (Iron Dextran BP)," Pharmaceut. Med. (1987), I, pp. 289-296.

WO20040375865, Certified Translation from German into English, May 27, 2015, 20 pages.

Wu, "Impact of Geographic and Cross-cultural Differences on Spontaneous Adverse Events Reporting," Drug Information Journal, vol. 33, 1999, pp. 921-931.

Yessayan, L., et al., "Intravenous Iron Dextran as a Component of Anemia Management in Chronic Kidney Disease: A Report of Safety and Efficacy," Int J Nephrol, 2013, published on line, 18 pages.

Yessayan, L., et al., "Intravenous Iron Dextran as a Component of Anemia Management in Chronic Kidney Disease: A Report of Safety and Efficacy," International Journal of Nephrology vol. 2013, Article ID 703038, 10 pages.

Zager, R.A., et al., "Parenteral Iron Formulations: A Comparative Toxicologic Analysis and Mechanisms of Cell Injury," American Journal of Kidney Diseases, vol. 40, No. 1 (Jul.), 2002: pp. 90-103.

Zolezzi, M., Intravenous Iron Saccharate Complex: Guidelines for its use in the Management of Anemia of Renal Disease, Saudi J. Kidney Dis. Transplant 2003;14(2), pp. 129-133.

Zou, P., "Physicochemical Characterization of Iron Carbohydrate Colloid Drug Products," The AAPS Journal, vol. 19, No. 5, Sep. 2017, pp. 1359-1379.

Hamstra, RD, Intravenou iron dextran in clinical medicine, JAMA. May 2, 1980;243(17):1726-31.

(56) References Cited

OTHER PUBLICATIONS

Handbook of Pharmaceutical Excipients, Third Edition, 2000, Maltodextrin 317-319.
Hartsfield, Jershonda, Iron Status in the Female Blood Donor, eScholarship UCLA Department of Biological Chemisty, UCLA, David Geffen School of Medicine Nutrition Bytes vol. 4, Issue 1 1998.
Hedin, Harriet, et al., Pathomechanisms of Dextran-Induced Anaphylactoid/Anaphylactic Reactions in Man, Int Arch Allergy Immunol 1982; 68: 122-126.
Helenek, Mary Jane, et al., U.S.PTO File Wrapper dated Nov. 25, 2019—U.S. Appl. No. 11/620,986, filed Jan, 8, 2007, U.S. Pat. No. 7,754,702, Issue Date of Patent: Jun. 13, 2010.
Helenek, Mary Jane, et al., U.S. Provisional Appl. No. 60/757,119, filed Jan. 6, 2006.
Helenek, Mary Jane, et al., U.S. Appl. No. 11/620,686, Non Final Office Action, dated Oct. 23, 2008.
Helenek, Mary Jane, et al., U.S.PTO File Wrapper—U.S. Appl. No. 11/620,986, filed Jan. 8, 2007, U.S. Pat. No: 7,754,702, issue date of Patent: Jul. 13, 2010.
Helenek, Mary Jane, et al., U.S. Appl. No. 12/787,283, Non Final Office Action, dated Mar. 23, 2012.
Helenek, Mary Jane, et al., U.S. Provisional Appl. No. 60/757,119 as filed Jan. 6, 2006.
Helenek, Mary Jane, et al., U.S. Appl. No. 11/620,986, Non Final Office Action dated Oct. 23, 2008.
Helenek, Mary Jane, et al., U.S.PTO File Wrapper—U.S. Appl. No. 13/847,254, filed Dec. 9, 2013.
Helenek, Mary Jane, et al., U.S. Appl. No. 14/100,717, Non Final Office Action, dated Feb. 7, 2014.
Helenek, Mary Jane, et al., U.S.PTO File Wrapper—U.S. Appl. No. 14/683,415, filed Apr. 10, 2015, U.S. Pat. No. 10,478,450, dated Nov. 19, 2019.
Merriam Webster.com Dictionary, May 28, 2015, Definition of hematinic: an agent that tends to stimulate blood cell formation or to increase the hemoglobin in the blood.
Highlights of Prescribing Information, These highlights do not include all the information needed to use Ferrlecit® safely and effectively. See full prescribing information for Ferrlecit, Ferrlecit® (sodium ferric gluconate complex in sucrose injection), for intravenous use Initial U.S. Approval: 1999.
Highlights of Prescribing Information, These highlights do not include all the information needed to use Venofer safely and effectively. See full prescribing information for Venofer. Venofer® (iron sucrose injection, USP) Initial U.S. Approval: 2000.
Kabat, Elvin A., et al., The Effect of Variation in Molecular Weigh on the Antigenicity of Dextran in Man, Archives Of Biochemistry And Biophysics 78, 306-318 (1958).
Kanton, Jonathan et al., Decreased Serum Ferritin is Associated With Alopecia in Women, The Journal of Investigative Dermatology, The Society for Investigative Dermatology, Inc., 2003, pp. 985-988.
Kardos, Nathalie et al., Sonochemistry of carbohydrate compounds, Carbohydrate Research 332 (2001) 115-131.
Keating, Gillian M., Ferric Carboxymaltose: A Review of Its Use in Iron Deficiency, Drugs (2015) 75:101-127.
Khalikova, Elivira et al., Microbial Dextran-Hydrolyzing Enzymes: Fundamentals and Applications, Microbiology And Molecular Biology Reviews, Jun. 2005, vol. 69, No. 2, pp. 306-325.
Handbook of Pharmaceutical Excipients, Third Edition, 2000, ISBN: 0-917330-96-X (USA) Maltodextrin, 317.
Kocakoc, Ercan et al., Pediatric Idiopathic Pulmonary Hemosiderosis Diagnosed by Sputum Analysis: Plain Radiography and Computed Tomography Findings, Med Princ. Pract. 2003; 129-132.
Konofal, MD, PhD, Eric, et al., Iron Deficiency in Children With Attention-Deficit/Hyperactivity Disorder, Arch Pediatr Adolesc Med/ vol. 158, Dec. 2004, 1113-1115.
European Journal of Haematology, Editor-In-Chief: Karl-Anton Kreuzer MD, vol. 98, No. 3, Mar. 2017.
Kumpf, Vanessa J. et al., Parental Iron Dextran Therapy, The Annals of Pharmacotherapy, Feb. 1990, vol. 24, 162-166.
Papanikolaou, G., et al., Iron metabolism and toxicity, Toxicology and Applied Pharmacology 202 (2005) 199-211.
Parkin, Jacqueline, et al., An Overview Of The Immune System, The Lancet, vol. 357, Jun. 2, 2001, 1777-1789.
United States Patent and Trademark Office Before The Patent Trial and Appeal Board *Pharmacosmos A/S*, Petitioner, v. *American Regent, Inc.*, Patent Owner, U.S. Pat. No. 8,431,549 Declaration Of Vanessa Park-Thompson In Support of Petitioner Pharmacosmos A/S's Motion For Admission Pro Hac Vice Executed at New York, NY Aug. 20, 2019.
Usher, Thomas C., CA, Patel NATU, US, Canadian Patent Application No. 2,195,283, filed Jan, 16, 1997, Title: Process For Manufacturing Iron Dextran Using Ultrafiltration.
Patel, Kanti M., et al., Total Dose Imferon (Iron-dextran Complex) Infusion Therapy in Severe Hookworm Anaemia, Brit. Med. J., 1967, 2, 605-607.
U.K. Provisional Patent Specification 335,965, Application dated Jun. 5, 1929, Inventor: Carpmael, Arthur, Title: Process For The Manufacture of Complex Lron Compounds.
U.K. Patent Specification 879, 441, Application dated May 26, 1959, No. 17695/59, date of filing Complete Specification: May 24, 1960, Complete Specification Published: Oct. 11, 1961, Inventor: Michael, Stephen Ernest, et al. Title: Improved Injectable Iron Preparations.
U.K. Patent Specification 918,737, date of Application and filing Complete Specification: Jun. 18, 1959. Application made in United States of America (No. 762230) on Sep. 22, 1958 Complete Specification Published: Feb. 20, 1963 Applicant: American Cyanamid Company, Title: Colloidal Ferric Hydroxide for Parenteral Administration.
U.K. Patent Specification 748,024, date of filing Complete Specification: Feb. 23, 1954, date of Application Feb. 27, 1953, Complete Specification Published: Apr. 18, 1956 Applicant: Benger's Limited, Title: Improved Therapeutic Preparations of Iron
U.K. Patent Specification 1377006, Application No. 38214/72, filed Aug. 16, 1972 Convention Application No. 172865, filed Aug. 18, 1971 In United States Of America, Complete Specification Published Dec. 11, 1974 Applicant: The Central Pharmacal Company, Title: Process For Preparing An Iron-Saccharide Complex.
Peacock, Eileen, et al., Clinical Practice Guidelines for Maintaining Adequate Iron Status With Intravenous Iron Dextran in Hemodialysis Patients, ANNA Journal Jun. 1999 vol. 26 No. 3.
United States Patent and Trademark Office Before The Patent Trial and Appeal Board *Pharmacosmos A/S*, Petitioner, v. *Luitpold Pharmaceuticals, Inc.*, Patent Owner. (U.S. Pat. No. 7,754,702 B2) (U.S. Pat. No. 8,431,549 B2) Petitioner's Notice Of Deposition Of Dr. Adriana Manzi, dated: Apr. 20, 2016.
United States Patent and Trademark Office Before The Patent Trial and Appeal Board *Pharmacosmos A/S*, Petitioner, v. *Luitpold Pharmaceuticals, Inc.*, Patent Owner. (U.S. Pat. No. 7,754,702 B2) (U.S. Pat. No. 8,431,549 B2) Petitioner's Corrected Notice Of Deposition Of Dr. Adriana Manzi, dated: Apr. 21, 2016.
United States Patent and Trademark Office Before The Patent Trial and Appeal Board *Pharmacosmos A/S*, Petitioner, v. *Luitpold Pharmaceuticals, Inc.*, Patent Owner U.S. Pat. No. 8,431,549, Petitioner Pharmacosmos A/S's Motion For Pro Hac Vice Admission Of Ryan P. Johnson Pursuant To 37 C.F.R. § 42.10(c) dated Jan. 6, 2020.
United States Patent and Trademark Office Before The Patent Trial and Appeal Board *Pharmacosmos A/S*, Petitioner, v. *American Regent, Inc.*, Patent Owner U.S. Pat. No. 8,431,549, Petitioner Pharmacosmos A/S's Motion For Pro Hac Vice Admission Of Ryan P. Johnson Pursuant To 37 C.F.R. § 42.10(c) dated Aug. 20, 2019.
United States Patent and Trademark Office Before The Patent Trial and Appeal Board *Pharmacosmos A/S*, Petitioner, v. *American Regent, Inc.*, Patent Owner U.S. Pat. No. 8,431,549, Petitioner Pharmacosmos A/S's Motion For Pro Hac Vice Admission Of Vanessa Park-Thompson Pursuant To 37 C.F.R. § 42.10(c) dated Aug. 20, 2019.
United States Patent and Trademark Office Before The Patent Trial and Appeal Board *Pharmacosmos A/S*, Petitioner, v. *Luitpold Phar-

(56) References Cited

OTHER PUBLICATIONS maceuticals, Inc., Patent Owner U.S. Pat. No. 8,431,549 B2 Petitioner's Motion For Withdrawal Of Counsel dated Dec. 19, 2019.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702 B2 Petitioner Pharmacosmos A/S's Notice Of Cross-Appeal, dated Mar. 8, 2017.
United States Patent and Trademark Office Before The Patent Trial and Appeal Board *Pharmacosmos A/S*, Petitioner, v. *Luitpold Pharmaceuticals, Inc.*, Patent Owner U.S. Pat. No. 7,754,702 B2; U.S. Pat. No. 8,431,549 B2 Petitioner's Notice Of Demonstrative, dated: Sep. 15, 2016.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702 B2; U.S. Pat. No. 8,431,549 B2 Petitioner's Notice Of Objections To Evidence, dated: Apr. 5, 2016.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702 B2; U.S. Pat. No. 8,431,549 B2; U.S. Pat. No. 8,895,612 B2, Petitioner's Objection to Patent Owner Response in Lieu of Motion (to Patent Owner Response in Lieu of Motion, Paper 9), dated: Oct. 30, 2015.
United States Patent and Trademark Office Before The Patent Trial and Appeal Board *Pharmacosmos A/S*, Petitioner, v. *Luitpold Pharmaceuticals, Inc.*, Patent Owner. Patent 7,754,702 B2; Patent 8,431,549 B2 Petitioner's Objections To Patent Owner's Demonstrative Exhibits, dated: Sep. 20, 2016.
United States Patent and Trademark Office Before The Patent Trial and Appeal Board *Pharmacosmos A/S*, Petitioner, v. *Luitpold Pharmaceuticals, Inc.*, Patent Owner Patent 7,754,702 B2; Title: Methods and Compositions For Administration Of Iron Inter Partes Review No. 2015-01490 Petitioner's Opposition To Patent Owner's Motion To Exclude, dated Aug. 23, 2016.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 B2 Petitioner's Opposition To Patent Owner's Motion To Amend, dated: Jun. 20, 2016.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 B2 Petitioner's Reply To Patent Owner's Response, dated: Jun. 20, 2016.
United States Patent and Trademark Office Before The Patent Trial and Appeal Board *Pharmacosmos A/S*, Petitioner, v. *Luitpold Pharmaceuticals, Inc.*, Patent Owner. Patent 7,754,702; Title: Methods and Compositions For Administration Of Iron Inter Partes Review No. 2015-01490, Petitioner's Request For Oral Argument, dated: Aug. 9, 2016.
United States Patent and Trademark Office Before The Patent Trial and Appeal Board *Pharmacosmos A/S*, Petitioner, v. *Luitpold Pharmaceuticals, Inc.*, Patent Owner. Patent No. 8,431,549 B2 Title: Methods And Compositions For Administration Of Iron Inter Partes Review No. 2015-01493 Petitioner's Request For Oral Argument, dated: Aug. 9, 2016.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 B2 Patent Owner Reply To Opposition To Motion To Amend, dated: Jul. 19, 2016.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 Petitioner's Revocation Of Power Of Attorney And New Power Of Attorney Pursuant To 37 C.F.R. §42.10(b), dated: Dec. 30, 2019.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 B2 Petitioner's Sur-Reply Responding To Patent Owner's Reply To Opposition To Motion To Amend, dated: Jul. 29, 2016.

United States Patent and Trademark Office Before The Patent Trial and Appeal Board *Pharmacosmos A/S*, Petitioner, v. *Luitpold Pharmaceuticals, Inc.*, Patent Owner. Patent 7,754,702 B2 Petitioner's Sur-Reply Responding To Patent Owner's Reply To Opposition To Motion To Amend, dated: Jul. 29, 2016.
United States Patent and Trademark Office Before The Patent Trial and Appeal Board *Pharmacosmos A/S*, Petitioner, v. *Luitpold Pharmaceuticals, Inc.*, Patent Owner. Patent 8,431,549 Petitioner Pharmacosmos A/S's Updated Exhibit List as of Jan. 6, 2020, dated: Jan. 6, 2020.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 8,431,549 Petitioner's Updated Mandatory Notice Information Under 37 C.F.R. §42.8, dated: Dec. 30, 2019.
United States Patent and Trademark Office Before The Patent Trial and Appeal Board *Pharmacosmos A/S*, Petitioner, v. *American Regent, Inc.*, Patent Owner. U.S. Pat. No. 10,478,450, Petition For Post Grant Review dated: Jan. 6, 2020.
*Pharmacosmos A/S v. American Regent, Inc.* Petitioner Ex. 1027—Highlights Of Prescribing Information Injectafer® (ferric carboxymaltose injection), for intravenous use Initial U.S. Approval: 2013.
*Pharmacosmos A/S v. American Regent, Inc.* Petitioner Ex. 1053—Ernster, Lars, Iron overload: molecular clues to its cause TIBS 24—May 1999 164-166.
United States Patent and Trademark Office Before The Patent Trial and Appeal Board *Pharmacosmos A/S*, Petitioner, v. *American Regent, Inc.*, Patent Owner. U.S. Pat. No. 10,478,450, dated: Jan. 17, 2020 Before Steven M. Amitrani, Trial Paralegal, Notice of Filing Date Accorded to Petition and Time for Filing Patent Owner Preliminary Response.
Physcians Desk Reference 36th Edition, 1982, Fisons Corporation 920-925.
Physcians Desk Reference 55th Edition, 2001, Ferrlecit®2878-2881.
Physcians Desk Reference 55th Edition, 2001, INFeD® Uron Dextron Injection, USP 2879-2881.
Physcians Desk Reference 56th Edition, 2002, American Regent Laboratories, Inc, Venofer®.
Picaud, J.C. et al., Supplementation en fer chez les enfants prematures traites par erythropoietine, Arch Pediatr 1999; 657-64.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702 B2, 1 Case, U.S. Pat. No. 8,431,549 B2 Patent Owner Notive Of Deposition Of Dr. Linhardt, dated: Feb. 17, 2016.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 8,431,549 B2 Patent Owner Exhibit List dated Mar. 29, 2016.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 8,431,549 B2 Patent Owner Exhibit List dated Jan. 6, 2020.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702 B2 Patent Owner Exhibit List dated Jul. 19, 2016.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 7,754,702, Patent Owner Mandatory Notices, dated: Jul. 15, 2015.
United States Patent and Trademark Office Before The Patent Trial and Appeal Board *Pharmacosmos A/S*, Petitioner, v. *Luitpold Pharmaceuticals, Inc.*, Patent Owner. U.S. Pat. No. 8,431,549 Patent Owner Mandatory Notices, dated: Jul. 15, 2015.
Lawrence, Richard Development and Comparison of Iron Dextran Products, J Pharm Sci and Tech 1998, 52190-197.
Leone, Roberto et al., Drug-Induced Anaphylaxis, Drug Safety 2005; 28 (6): 547-556.
Lewis, R, Practical Guide to Autoclave Validation, Pharmaceutical Engineering, Jul.-Aug. 2002 (pp. 1-8).

(56) References Cited

OTHER PUBLICATIONS

Declaration of Linhardt, Robert filed on behalf of Pharmacosmos A/S, Jun. 22, 2015, pp. 1-29.
Linhardt, Robert et al, Production and Chemical Processing of Low Molecular Weight Heparins, Seminars in Thrombosis and Hemostasis-vol. 25, Suppl. 3, 1999, pp. 5-16.
Lynch, R.E. et al. The Anemia of Vitamin E Deficiency in Swine; An Experimental Model of the Human Congenital Dyserythropoietic Anemias, American Journal of Hematology 2:145-158 (1977).
Nadarajan, Veera S. et al., Anaemia And Iron Status Among Blood Donors In A Blood Transfusion Unit in Malaysia, Malaysian Pathol 2002; 24(2):99-102
Nagpal, Jitender et al., Iron Formulations in Pediatric Practice, Indian Pediatrics 2004; 41:807-815.
National Kidney Foundation. K/DOQI Clinical Practice Guidelines for Anemia of Chronic Kidney Disease, 2000. Am J Kidney Dis 3 7 :S 182-S23 8, 2001 (suppl 1).
National Kidney Foundation, KDOQI Clinical Practice Guidelines and Clinical Practice Recommendations for Anemia in Chronic Kidney Disease. Am J Kidney Dis 47:SI-S146, 2006 (suppl 3).
NDA 17-441/S-171, INFeD® (Iron Dextran Injection USP) Rx Only Revised: Jul. 2009.
NDA 20-955/S-003, Ferrlecit® (sodium ferric gluconate complex in sucrose injection) pp. 3-11 (2001).
NDA 21-135, Venofer® (iron sucrose injection) pp. 1-9 (2000).
Neiser, Susann et al., Assessment of dextran antigenicity of intravenous iron products by an immunodiffusion assay, Port J Nephrol Hypert, Advance Access publications Sep. 27, 2012, 26(4).
Neiser, Susann et al., Assessment of dextran antigenicity of intravenous iron products by an immunodiffusion assay, Port J Nephrol Hypert 2011; 25(3): 219-224, Sep. 13, 2011.
Fielding, J., M.R.C.P., D.P.H., Intra Venous Iron-Dextrin in Iron-Ueficiency Anaemia, British Medical Journal, Jul. 29, 1961, 279-283.
New Zealand Data Sheet, Ferrum H solution for injection 100 mg/2mL ampoule (Apr. 18, 2019).
National Kidney Foundation. K/DOQI Clinical Practice Guidelines for Hemodialysis Adequacy, 2000. Am J Kidney Dis 37:S7-S64, 2001 (suppl 1).
De Nooy, Arjan E.J., et al, On the Use of Stable Organic Nitroxyl Radicals for the Oxidation of Primary and Secondary Alcohols, Synthesis, Oct. 1996, 1153-1174.
Nordmeier, Eckhard, Static and Dynamic Light-Scattering Solution Behavior of Pullulan and Dextran in Comparison, J, Phys. Chem. 1993, 97, 5770-5785.
United States Patent and Trademark Office Before The Patent Trial and Appeal Board *Pharmacosmos A/S*, Petitioner, v. *Luitpold Pharmaceuticals, Inc.*, Patent Owner. Notice (Regarding the Filing of Corrected Exhibits and Papers) (Apr. 25, 2016).
Notice of Correction of Certificate of Service for Petition for Inter Partes Review of U.S. Pat. No. 7,754,702 Inventor: Mary Jane Helenek et al., filed Jan. 8, 2007, dated Jul. 13, 2010, Title: Methods and Compositions for Administration of Iron.
Notice of Correction of Certificate of Service for Petition for Inter Partes Review of U.S. Pat. No. 8,431,549, Inventor: Mary Jane Helenek et al., filed May 25, 2010, dated Apr. 30, 2013, Title: Methods and Compositions for Administration of Iron.
Notice of Correction of Certificate of Service for Petition for Inter Partes Review of U.S. Pat. No. 8,895,612, Inventor: Mary Jane Helenek et al., filed Dec. 9, 2013, dated Nov. 25, 2014, Title: Methods and Compositions for Administration of Iron.
United States Patent and Trademark Office—Notice of Publication of Application, and Updated Filing Receipt dated Jul. 16, 2015, U.S. Appl. No. 14/683,415, filed Apr. 10, 2015, U.S. Pub. No. US-2015-0297630-A 1, dated Oct. 22, 2015, Title: Methods and Compositions for Administration of Iron.
Ferrum-Hausmann—Solution for Injection—Reg. No. HW:49420— Application form for entering a medicinal product in the Special Registry—Submitted to Budesgesundheitsamt (BGA) Federal Health Agency in Berlin German, dated Apr. 6, 1978.

Ahsan, Nasimul, et al. "Efficacy of Bolus Intravenous Iron Dextran Treatment in Peritoneal Dialysis Patients Recombinant Human Erythropoletin," Advances in Peritoneal Dialysis: Selected Papers from the 16th Annual Conference on Peritoneal Dialysis, Seattle Washington, Feb. 1996. vol. 12, 1996.
Report of ACS Carbohydrate Division, Nomenclature Committee. Annual Meeting of ACS Committee on Nomenclature, Terminology and Symbols, Apr. 7, 2008, New Orleans, LA. Luitpold Pharmaceuticals, Inc. Ex 2125, p.1. *Pharmacosmos A/S* vs. *Luitpold Ex. Pharmaceuticals Inc.* IPR 2015-01493.
Shearer, William T., et al. "Chapter 1: The Immune System," Adkinson Jr. M.D., N. Franklin, et al. Middleton's Allergy Principles and Practice, 6th Edition, vol. 1, Mosby 2003, pp.1-14.
Frank, Michael, et al. "Chapter 58: The Immune Complexes and Allergic Disease," Adkinson Jr. M.D., N. Franklin, et al. Middleton's Allergy Principles and Practice, 6th Edition, vol. 2, Mosby 2003, pp. 997-1014.
Adkinson Jr. M.D., N. Franklin, "Chapter 92: Drug Allergy," Adkinson Jr. M.D., N. Franklin, et al. Middleton's Allergy Principles and Practice, 6th Edition, vol. 2, Mosby 2003, pp. 1679-1694.
Adkinson Jr. M.D., N. Franklin, Curriculum Vitae, Jul. 9, 2019.
Declaration of N. Franklin Adkinson, Jr. M.D., Jan. 6, 2020, *Pharmacosmos A/S* v. *American Regent, Inc.* PGR 2020-00009, U.S. Pat. No. 10,478,450.
"Iron Polymaltose," and "Carnidazole," Medicaments de Actualidad (Drugs of Today), vol. 12, No. 10, 1976, pp. 423-426.
Al, M.D., Ragip A., et al. "*Intravenous* vs. *Oral Iron for Treatment of Anemia in Pregnancy*," Obstetrics and Gynecology, vol. 106, No. 6, Dec. 2003, pp. 1335-1340.
Alternative Dispute Resolution Statement, *Pharmacosmos A/S* v, *Luitpold Pharmaceuticals Inc.*, U.S. Pat. No. 7,754,702 and U.S. Pat. No. 8,431,549.
FDA Advisory Committee Briefing Document, Drug Safety and Risk Management Committee, Feb. 1, 2008, FDA New Drug Application (NDA) 22-054 for Injectafer (Ferrous Carboxymaltose). American Journal of Kidney Diseases, vol. 47, No. 5, Supplement 3, May 2006.
CZ Vereinaria SL Quality Department, Certificate of Analysis for Anaemex, Batch 98001, Jan. 14, 1998.
Anelli, P.L., et al. "Fast and Selective Oxidation of Primary Alcohols . . . ," J. Org. Chem. 1987, vol. 52, pp. 2559-2562.
Supplementary European Search Report of the European Patent Office, of European App. EP 017716309, dated Oct. 8, 2009.
Division of Gastrointestinal and Coagulation Drug Products, Review of Chemistry, Manufacturing and Controls, NDA 21-135, Oct. 27, 2000.
Amendment dated Feb. 4, 2008 in reply to Office Action dated Oct. 5, 2007 in U.S. Pat. No. 10,531,895, Remarks section.
USPTO Non Final Office Action dated Oct. 3, 2011 issued in U.S. Appl. No. 12/581,212, filed Oct. 19, 2009.
USPTO Final Office Action dated Nov. 5, 2013, issued in U.S. Appl. No. 13/556,733, filed Jul. 24, 2012.
Auerbach, M., et al. "How we diagnose and treat iron deficiency anemia," Amer. Journal of Hematology, vol. 91, No. 1, Jan. 2016.
Auberbach, M. et al. "The availble intravenous iron formulations: History, efficacy and toxicology," Hemodialysis International, 2017, vol. 21, pp. 583-592.
Avaltroni, F., et al. "Maltodextrin molecular weight distribution influence on . . . ," Carbohydrate Polymers, vol. 58 (2004) pp. 323-334.
Anvi, MD, Tomer, et al. "The Safety of Intravenous Iron Preparations: Systematic Review and Meta-Analysis," Mayo Clinic Proceedings, Jan. 2015:90 (1): 12-23, Mayo Foundation for Medical Education and Research.
Baille, George R., et al. "Parenteral Iron Use in the Management of Anemia in End-Stage Renal Disease Patients," Amer. J. Kidney Diseases, vol. 35, No. 1, Jan. 2000.
Fox, Sir Theodore, et al. (Ed.) "Rapid Administration of Iron Dextran in Late Pregnancy."The Lancet, vol. 1, Jan.-Jun. 1963. The Lancet Limited, London.
BeMiller, James N. "Polysaccharides"Enclycopedia of Life Sciences, 2001, John Wiley and Sons Ltd. www.els.net.

(56) References Cited

OTHER PUBLICATIONS

Besemer, Arie C., et al. ". . . Bromixe Oxidation and its Calcium Building Properties," Starch/starkle, vol. 46, No. 3 (1994) S. 95-101.
Besara, S., et al. "Pharmacosmos and red cell utilization of iron (III) hydroxide-sucrose complez in anaemic patients: a study using position emission tomography," British J. Hematology 199, 104, 246-302.
Auberbach, Michael, et al. "Clinical Use of the total dose intravenous infusion of iron dextran," J. Lab Clin Med, vol. 111, No. 5, May 1988.
Haines, M. L. et al. "Delayed adverse reactions to total dose intravenous iron polymaltose," Internal Medicine Journal, vol. 39 (2009) 252-255.
"Iron and Erythrocyces in Dialysis Patients" J Am Soc Nephrol 14:2003. PGR2020-00009 *Pharmacosmos A/S v. American Regent Inc.* Petitioner Ex. 1069-p. 1.
Blaustein, DA, et al. "Recent experience with high dose intravenous iron administration" Kidney International, 70 (2006) 526-529, International Society of Nephrology, 2006.
"Iron Deficiency and Impaired Child Development" BMJ, vol. 323 (Dec. 15, 2001) pp. 1377-8.
Broadhead, Joanne "Chapter 9: Parenteral dosage forms, " Pharmacology Preformulation and Formulation: A Practical Guide . . . 2001 IHS Health Group, ISBN 1-57491-120-1.
Brugnara, Carlo "Iron Deficiency and Erythropiesis: New diagnostic approaches" Clinical Chemistry 49:10 1573-1578 (2003).
Brunner, Walter, et al. "Sanz-Streiflicht Nr. 21" Mozaik 1995.
Brunner, Walter, et al. (English translation) "SANZ Highlight No. 21, Parenteral iron application: problems with iron dextran preparations" Mosaic (1995).
Burns, David L., et al. "Patenteral Iron Dextran Therapy: A Review," Nutrition, vol. 11, No. 5 (1995).
Burns, David L., et al. "Toxicity of Parenteral Iron Dextran Therapy" Kidney International, vol. 55, Supp. 69 (1999) S-119—S-124.
Cada, Dennis J. "Formulary Drug Review: Ferric Carboxymaltose" Hosp Pharm 2014; 49:1; 52-69, 2014 Thomas Land Publishers, Inc.
Carroll, Michael "The Complement system in regulation of adaptive immunity" Nature Immunology, vol. 5, No. 10, Oct. 2004. Nature Publishing Group 2004.
File History U.S. Appl. No. 11/620,986 filed Jan. 8, 2007, U.S. Pat. No. 7,754,702 dated Jul. 13, 2020.
Center for Drug Evaluation and Research, Division of Gastroenterology and Coagulation Drug Products, Application No. 21-135 (Applicant: Luitpold Pharaceuticals, Inc.) Chemistry Reviews, dated Oct. 27, 2000.
Corrected Motion to Amend, submitted to USPTO Patent Trial and Appeal Board, *Pharmacosmos v. Luitpold Pharmaceuticals, Inc.* in U.S. Pat. No. 7,754,702 B2.
Corrected Motion to Amend, submitted to USPTO Patent Trial and Appeal Board, *Pharmacosmos v. Luitpold Pharmaceuticals, Inc.* in U.S. Pat. No. 8,431,549 B2.
Corrected Patent Owner Exhibit List, submitted to USPTO Patent Trial and Appeal Board, *Pharmacosmos v. Luitpold Pharmaceuticals, Inc.* in U.S. Pat. No. 7,754,702 B2.
Corrected Patent Owner Exhibit List, submitted to USPTO Patent Trial and Appeal Board *Pharmacosmos v. Luitpold Pharmaceuticals, Inc.* U.S. Pat. No. 8,431,549 B2.
Coulson, J. et al. "Some observations on the immunochemistry of dextrans,"The Journal of Immunology, vol. 86, Baltimore, 1961.
Crichton, Robert R., et al. "Chapter 2. Iron Metabolism: Biological and Molecular Aspects," Iron Therapy with Special Emphasis on Intravenous Administration, 3rd ed. UniMed 2006.
United States Patent and Trademark Office Before The Patent Trial and Appeal Board *Pharmacosmos A/S* Petitioner, v. *American Regent, Inc.*, Patent Owner U.S. Pat. No. 8,431,549 Patent Owner Mandatory Notices, dated: Jul. 3, 2019.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 Patent Owner Motion to Exclude, dated: Aug. 9, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 Patent Owner's Notice of Appeal, dated: Mar. 2, 2017.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 Patent Owner's Notice of Appeal, dated: Mar. 2, 2017.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2 1 case, U.S. Pat. No. 8,431,549 B2 Patent Owner Notice of Deposition of Dr. Linhardt, dated: Feb. 17, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2 Patent Owner Notice of Disclaimer, dated: Sep. 27, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Notice of Disclaimer, dated: Sep. 27, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2 Patent Owner Ojections to Evidence, dated: Jan. 27, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2; U.S. Pat. No. 8,431,549 B2 Patent Owner Oral Hearing Demonstratives, dated: Sep. 15, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 dated Jul. 13, 2010 Title: Methods and Compositions for Administration of Iron Inter Partes Review No. 2015-01490 Patent Owner Preliminary Response dated: Oct. 12, 2015.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 dated: Apr. 30, 2013 Title: Methods and Compositions for Administration of Iron Inter Partes Review No. 2015-01493 Patent Owner Preliminary Response dated: Oct. 12, 2015.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,895,612 dated: Nov. 25, 2014 Title: Methods and Compositions for Administration of Iron Inter Partes Review No. 2015-01495 Patent Owner Preliminary Response dated: Oct. 12, 2015.
United States Patent and Trademark Office Before The Patent Trial and Appeal Board *Pharmacosmos A/S* Petitioner, v. *American Regent, Inc.*, Patent Owner U.S. Pat. No. 8,431,549 Patent Owner Preliminary Response dated: Sep. 19, 2019.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Reply to Opposition to Motion to Amend dated: Jul. 19, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Reply to Opposition to Motion to Exclude dated: Aug. 30, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2 Patent Owner Request for Oral Argument dated: Aug. 9, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Request for Oral Argument dated: Aug. 9, 2016.

(56) References Cited

OTHER PUBLICATIONS

United States Patent and Trademark Office Before The Patent Trial and Appeal Board *Pharmacosmos A/S* Petitioner, v. *Luitpold Pharmaceuticals, Inc.*, Patent Owner U.S. Pat. No. 7,754,702 B2 Patent Owner Response dated: Mar. 29, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Response dated: Mar. 29, 2016.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner's Response to Ultra Vires Order (Paper 57) Requiring a Showing of Good Cause Why Claim 15 of U.S. Pat. No. 8,431,549 Should Not Be Deemed Unpatentable dated: Jan. 6, 2020.
United States Patent and Trademark Office Before The Patent Trial and Appeal Board *Pharmacosmos A/S* Petitioner, v. *Luitpold Pharmaceuticals, Inc.*, Patent Owner U.S. Pat. No. 8,431,549 B2 Patent Owner Updated Mandatory Notices dated: Jan. 6, 2020.
Polysaccharide nomenclature (Provisional) Pure Appl. Chem., 1982, vol. 54, No. 8, pp. 1523-1526.
Pond, Wilson G., et al Cadmium-Induced Anemia In Growing Pigs: Protective Effect Of Oral Or Parenteral Iron, Journal of Animal Science, vol. 36, Issue 6, Jun. 1973, pp. 1122-1124.
Prakash, Sunil, et al. Experience With A Large Dose (500 Mg) Of Intravenous Iron Dextran And Iron Saccharate In Peritoneal Dialysis Patients, Peritoneal Dialysis International, vol. 21, pp. 290-295 (May 2001).
Preusser, Lee C. et al. Effects Of Intra Venous Abt-870 (Iron (111)-Hydroxide Oligosaccharide) On Mean Arterial Pressure And Heart Rate In the Anaesthetized Beagle: Comparison With Other Iron-Containing Haematinic Agents, Clinical and Experimental Pharmacology and Physiology (2005) 32, 1020-1026.
Prince, Martin R., et al. A pilot investigation of new superparamagnetic iron oxide (ferumoxytol) as a contrast agent for cardiovascular MRI, Journal of X-Ray Science and Technology II (2003) 231-240.
Principles and Methods of Sterilization—Principles of Steam Sterilization, Sterilizing Conditions Basis-Temperature Rather Than Pressure, 116-121 (1960).
SPC-Y A460/ AU/E06 Product Information Ferrum H® Injection, Vifor (International) Inc., pp. 1-7 (Jun. 2, 2015).
Australian Government Department of Health Therapeutic Goods Administration, Public Summary—68110 Ferrum H iron 100mg/2mL (as polymaltose) injection ampoule. Jun. 27, 1999.
Australian Goverment Department of Health Therapeutic Goods Administration, Public Summary—82435 Ferrosig Injection iron 100mg/2mL (as polymaltose) injection ampoule (Apr. 22, 2002).
Purina Pigemia, 100cc 50 dose (Injectable), Jul. 25, 1968 Ralston Purina Co., St. Louis 2, Missouri.
MacDougall and Roche, "Administration of Intravenous Iron Sucrose as a 2-Minute Push to CKD Patients: A Prospective Evaluation of 2,297 Injections" American Journal of Kidney Diseases, vol. 46, No. 2 (Aug.), 2005: pp. 283-289 (2005).
MacDougall and Vernon, "Complement Activation-Related Pseudo-Allergy: A Fresh Look at Hypersensitivity Reactions to Intravenous Iron" Am J Nephrol 2017;45:60-62 (2017).
MacDougall I.C., "Evolution of IV Iron Compounds Over the Last Century" Journal of Renal Care 2009 pp. 8-13 (2009).
Walport M.J., "Advances in Immunology" N. Engl. J. Med, vol. 344, No. 14, Apr. 5, 2001 pp. 1058-1066 (2001).
Falbe et al., "Rompp Lexikon Chemie," p. 2513, Maltodextrine [original document in German with certified English translation], 4 pages (1998).
Marchasin and Wallerstein, "The Treatment of Iron-Deficiency Anemia with Intravenous Iron Dextran", Blood, vol. 23, No. 3, (Mar.), 1964, pp. 354-358 (1964).
Marcy et al., "Injectable Ferric Hydroxide Polymaltose: I. Investigation of the Acute Toxicity of High and Very High Dosages in Rats and Mice" IRCS Medical Science: Drug Metabolism and Toxicology: Hermatology: Pharmacology, 5, 255 (1977).

McMurry J., "Fundamentals of Organic Chemistry", Fifth Edition pp. 119-121 (2003).
Meier et al. "Physicochemical and toxicological characterization of a new generic iron sucrose preparation." Arzneimittel-Forsch. 2011;61(2):112-9 (2011).
Merriam-Webster Collegiate Dictionary, pp. 864 and 961, 4 pages. (2005).
Mocan et al., "Breath holding spells in 91 children and response to treatment with iron", Arch Dis Child 1999;81:261-262 (1999).
Moore et al., "Uptake of Dextran-Coated Monocrystalline Iron Oxides in Tumor Cells and Macrophages", vol. 7, No. 6, JMRI, pp. 1140-1145 (1997).
Mollan and Celik, "Maltodextrin", Analytical Profiles of Drug Substances and Excipients, vol. 24, pp. 308-349 (1996).
Moride et al., "Under-reporting of adverse drug reactions in general practice", Br J Clin Pharmaco/ 1997; 43: 177-181 (1997).
Morton et al., "Refining procedures for the administration of substances", Laboratory Animals (2001) 35, 1-41 (2001).
Motion to Amend, dated Mar. 29, 2016, in connection with U.S. Appl. No. 12/787,283 (U.S. Pat. No. 8,431,549), 42 pages.
Munoz and Martfn-Montanez, "Ferric carboxymaltose for the treatment of iron deficiency anemia", Expert Opinion on Pharmacotherapy, 13:6, 907-921, DOI: 10.1517/1456566.2012.669373 (2012).
Mulder, M.B. "Comparison of hypersensitivity reactions of intravenous iron: iron isomaltoside-1000 (Monofer®) versus ferric carboxymaltose (Ferinject®). A single center, cohort studt," Br J Pharmacol (2019) vol. 85:385-392.
Qassim, A., et al. "Safety and Efficacy of Intravenous iron polymaltose, iron sucrose and ferric carboxymaltose in pregnancy: a systematic review," Aust NZ Obstet Gyn, vol. 58, 2018, pp. 22-39.
Registry Nos. 4600-00-4 through 12699-98-8. Chemical Abstract Service Registry Handbook—Number Section 1965-1971. American Chemical Society 1974.
Report of the ACS Carbohydrate Division Nomenclature Committee, Annual Meeting of the ACS Committee on Nomenclature, Terminology and Symbols. National Meeting in New Orleans, LA, Apr. 7, 2008.
Request for Rehearing Under 37 CFR 42.71(d) dated Jan. 22, 2016 in *Pharmacosmos A/S* v. *Luitpold Pharmaceuticals, Inc.* U.S. Pat. No. 8,431,549.
Response of Petition to Board's Dec. 18, 2019 Order Requiring a Showing of Good Cause. dated Jan. 6, 2020 in *Pharmacosmos A/S* v. *Luitpold Pharmaceuticals, Inc.* U.S. Pat. No. 8,431,549.
Revised Patent Owner Notice of Deposition of Dr. Linhardt, dated Feb. 19, 2016 in *Phamacosmos A/S* v. *Luitpold Pharmaceuticals, Inc.* U.S. Pat. Nos. 8,431,549 and 7,754,702,
Richter, W. "Minimal molecular size of dextran required to elicit heterologous passive cutaneous anaphylaxis in guinea pigs," Int. Arch Allergy 43: 252-268 (1972).
Richter, W. "Effect of Substitution on reactivity of B 512 dextran fractions with anti-B 512 dextran in heterologous passive cutaneous anaphylaxis," Int. Archs Allergy appl. Immun vol. 48:502-512 (1975).
Richter, W., et al "Dextran hypersensitivity," Immunology Today, vol. 3, No. 5, 1982, pp. 137-139.
Declaration of Ellen C. Reimschneider, dated Feb. 4, 2016.
Rockey, Don C., et al. "Evaluation of the Gastrointestinal Tract in Patients with Iron Deficiency Anemia," Gastrointestinal and Iron Deficient Anemia—Rocey and Cello. vol. 329, No. 23 (1993).
Roeser, H.P., et al. "The Role of Ceruloplasmin in Iron Metabolism," Journal of Clinical Investigation, vol. 49, 1970.
Rong, Y., et al. "Determination of dextrose equivalent value and number average molecular weight of maltodextrin by osmometry," Journal of Food Science, vol. 74, No. 1, 2009.
Rosse, Wendell, et al. "The Effect of Iron Therapy in Paroxysmal Nocturnal Hemoglobinuria," Blood. vol. 36, No. 5, Nov. 1970.
Rote List 1996 BPI Service GmbH.
Rutenberg, Morton, et al. "Chapter X: Starch Derivatives: Production and Uses." (1984).
Sabatie, J., et al. "Shear-induced structure in enzymaticall-synthesized dextran solutions," Rheol Acta. vol. 25: 287-295 (1986).

(56) References Cited

OTHER PUBLICATIONS

Sell, Stewart "Chapter 5: Antigenicity and Immunogenicity," Immunology, Immunopathology and Immunity, 4th Ed. 1987 Elsevier Science Publishing.
Shearer, W., et al. "Section A Immunology—Chapter 1: The Immune System," Middleton's Allergy Principles and Practice, 6th Ed. vol. 1, 2003, Mosby.
Shekunov, Boris, et al. "Particle size analysis in pharmaceutics: principles methods and applications," Pharm Res. vol. 24, No. 2, Feb. 2007.
Silverstein, Scott B., et al. "Parenteral Iron Therapy Options," Amer J. Hematology. vol. 76:74-78 (2004).
Sogbanmu, M.O., "Anaemia of pregnancy treated with total dose infusion of iron-polymaltose complex, Teferrol," Current Therapeutic Research, vol. 20, No. 2, Aug. 1976.
St. Peter, Wendy, et al. "Randomized cross over study of adverse reactions and cost implications of intavenous push compared with infusion of iron dextran in hemodialysis patients," Amer J Kidney Diseases, vol. 28, No. 4, Oct. 1996.
Starzynski, R., et al. "Iron supplementation in suckling piglets: How to correct iron deficiency anamia without affecting plasma hepcidin levels," Plos One, vol. 8, No. 5, May 2013. www.plosone.org
Stranz, Marc "A Review of pH and Osmolarity," Int J Pharm Compounding, Aug. 2013.
Stryer, Lubert "Chapter 18: Carbohydrates," Biochemistry, 4th Ed. 1995. W.H. Freeman and Co., New York.
Sur-Reply to Petitioners Reply to Patent Owner Preliminary Response. *Pharmacosmos A/S* v. *American Regent, Inc.* U.S. Pat. No. 8,431,549 (Oct. 15, 2019).
Svoboda, M., et al. "Intramuscular versus subcutaneous administration of iron dextran in suckling pigs," Acta. Vet. BRNO (2007) vol. 76:S11-S15.
Technical Quality Dextran, Pamphlet by Pharmacosmos, Apr. 2014, 6 pages.
Teuten, A., Letter from SagittariusIP European Law Firm to European Patent Office regarding European Patent Application No. 07716309.5, Jan. 15, 2014, 7 pages.
Teuten, A., Letter from SagittariusIP European Law Firm to European Patent Office regarding European Patent Application No. 07716309.5, Dec. 14, 2012, 4 pages.
Thaburet, JF et al., "TEMPO-mediated oxidation of maltodextrins and D-glucose: effect of pH on the selectivity and sequestering ability of the resulting polycarboxylates," Carbohydrate Research, 330 (2001) pp, 21-29.
Thaburet, JF et al., Abstract of "TEMPO-mediated oxidation of maltodextrins and D-glucose: effect of pH on the selectivity and sequestering ability of the resulting polycarboxylates," Carbohydrate Research 330 (2001) pp. 21-29, 1 page.
The Merck Index, Dextranase, 15th Edition, 2006, pp. 2959-2950.
The Official Compendia of Standards, Combined Index to USP 25 and NF 20, 2002, 30 pages.
The Official Compedia of Standards, Combined Index to USP 26 and NF 21,2003, 35 pages.
Thorek, D.L.J., et al., "Superparamagnetic Iron Oxide Nanoparticle Probes for Molecular Imaging," Annals of Biomedical Engineering, vol. 34, No. 1, Jan. 2006, pp 23-38.
Till, M.C. letter to Office of Regulatory Policy, Food and Drug Administration for application for patent term extension of U.S. Pat. No. 7,612,109, dated Oct. 22, 2014, 75 pages.
Till, M.C., letter regarding Patent Term Extension—Application for U.S. Pat. No. 6,599,498, recieved Mar. 26, 2014, 144 pages.
Tuomainen, T.P., et al., "Oral Supplementation with Ferrous Sulfate but not with Nonionic Iron Polymaltose Complex Increases the Susceptibility of Plasma Lipoproteins to Oxidation," Nutrition Research, vol. 19, No. 8, 1999, pp. 1121-1132.
Texas H.B. 1325, 86th legislature, 2019, v.1.
Texas H.B. 1325, 86th legislature, 2019, v.2.
United States District Court, District of New Jersey. Plaintiffs' Preliminary List of Proposed Claim Terms for Construction; *VIFOR (International) AG* and *American Regent, Inc.*, Plaintiffs v. *Mylan Laboratories Ltd.* and *Sandoz Inc.*, Defendants. (FLW) (DEA). Submitted to the Court dated Jun. 22, 2020.
United States District Court, District of New Jersey. Defendants Mylan Laboratories Ltd.'s and Sandoz Inc.'s Identification of Proposed Claim Terms for Construction; *VIFOR (International) AG* and *American Regent, Inc.*, Plaintiffs v. *Mylan Laboratories Ltd.* and *Sandoz Inc.*, Defendants. (FLW) (DEA). Submitted to the Court dated Jun. 22, 2020.
United States District Court, District of New Jersey. Joint Claim Construction and Prehearing Statement; *VIFOR (International) AG* and *American Regent, Inc.*, Plaintiffs v. *Mylan Laboratories Ltd.* and *Sandoz Inc.*, Defendants. (FLW) (DEA). Filed to the Court on Jul. 24, 2020.
Opposition Decision. IP Australia—Australian Patent Office *Pharmacosmos Holding A/S* v. *American Regent, Inc.* [2020]APO 36; Re: AU Patent Application:2016205002 for Methods and compositions for administration of iron. Patent Applicant: American Regent, Inc. Opponent: Pharmacosmos Holding A/S; Decision dated Jul. 29, 2020.
United States District Court, District of New Jersey. Plaintiffs' Preliminary Proposed Claim Construction and Identification of Evidence; *VIFOR (International) Ag* and *American Regent, Inc.*, Plaintiffs v. *Mylan Laboratories Ltd.* and *Sandoz Inc.*, Defendants. (FLW) (DEA). Dated Jul. 6, 2020.
United States District Court, District of New Jersey. Defendants Mylan Laboratories Ltd.'s and Sandoz Inc.'s Preliminary Claim Constructions; *VIFOR (International) Ag* and *American Regent, Inc.*, Plaintiffs v. *Mylan Laboratories Ltd.* and *Sandoz Inc.*, Defendants. (FLW) (DEA). Dated Jul. 6, 2020.
Danielson, Bo G., et al. Iron Therapy. Excerpt from Iron Therapy with Special Emphasis on Intravenous Administration. First Edition. Vifor International. 1996. 18 pages.
Fong, Singh K. A comparison between intravenous iron polymaltose complex (Ferrum Hausmann) and oral ferrous fumarate in the treatment of iron deficiency anaemia in pregnancy. Eur J Haematol 1998: 60; 119-124, 6 pages.
Fielding, J. Intravenous Iron-Dextrin in Iron-Deficiency Anaemia. British Medical Journal. Jul. 29, 1961, pp. 279-283.
Besemer, Arie C., et al. The Catalytic Effect of Bromide in the Hypochlorite Oxidation of Linear Dextrins and Inulin. starch/stiirke 46 (1994) Nr. 3, S. 101-106.
Collins, Peter M. (Ed.), et al. Excerpt from Dictionary of Carbohydrates. First Edition. 1998 Springer Science + Business Media Dordrecht. 5 pages.
Kearsley, M. W. and Dziedzic, S. Z., Editors. Excerpt from Handbook of Starch Hydrolysis Products and their Derivatives. First Edition. 1995 Springer Science + Business Media Dordrecht. 10 pages.
Dextrine. Wikipedia. 2 pages.
Anthony L. DeFranco, BioSketch, 2020.
Injectafer® Label, revised Feb. 2020.
Rodolfo Delfin! Cancado et al., Intravenous iron therapy how far have we come, REV BRAS HEMATOL Hemoter. 2011;33(6):461-9.
Sell, Stewart, Introduction to Part II, Immunology, Immunopathology and Immunity, sixth edition, 2001.
Crommelin et al., Different Pharmaceutical Products Need Similar Terminology, 16 The AAPS Journal 1: 11-14 (2013).
Preliminary Amendment A for PCT/EP2003/011596, received Apr. 20, 2005.
Amendment B for U.S. Appl. No. 10/531,895 in response to OA Oct. 5, 2007.
Iben Damager, Chemical synthesis of 6-alpha-maltotriosyl-maltohexaose as substrate for enzymes in starch biosynthesis and degradation, Carbohydrate Research 320 (1999) 19-30.
Shiro Kobayashi, Enzymatic Polymerization of alpha-D-maltosyl fluoride utilizing alpha-Amylase as the catalyst: A new approach for the synthesis of maltooligosaccharides, Macromolecules 1992, 25, 3237-3241.
Riichiro Uchida, New enzymatic synthesis of6/\3-modified maltooligosaccharides and their inhibitory activities for human alpha-amylases, Carbohydrate Research 307 (1998) 69-76.

(56) References Cited

OTHER PUBLICATIONS

Stefan Mühlebach & Beat Flühmann, Iron carbohydrate complexes: Characteristics and regulatory challenges, in Non-Biological Complex Drugs: The Science and the Regulatory Landscape 149-170 (Daan J.A. Crommelin & Jon S. B. de Vlieger eds., 2015).
U.S. Appl. No 10/519,252 patent prosecution history, dated Aug. 13, 2015 Office Action.
U.S. Appl. No 10/519,252 patent prosecution history, dated Feb. 12, 2016 Response.
U.S. Appl. No 10/519,252 patent prosecution history, Feb. 22, 2016 Supplemental Response, including Feb. 15, 2016 Declaration of Erik Philipp.
U.S. Appl. No 10/519,252 patent prosecution history, dated Jun. 24, 2016 Office Action.
U.S. Appl. No 10/519,252 patent prosecution history, dated Dec. 22, 2016 Amendment and Response.
U.S. Appl. No 10/519,252 patent prosecution history, Nov. 17, 2017 Supplemental Response, including Nov. 8, 2017 Declaration of Erik Philipp.
U.S. Appl. No. 10/519,252 patent prosecution history, dated Jun. 26, 2019 Notice of Allowance.
U.S. Appl. No. 10/519,252 patent prosecution history, dated Nov. 14, 2019 Notice of Allowance.
The United States Pharmacopeia, The National Formulary. 25.20: 2557-58 (2002).
R. Michael Aslop, History, Chemical and Pharmaceutical Development of Icodextrin, Peritoneal Dialysis Int'L, 14:5-13 (1994).
Bo G. Danielson et al., Pharmacokinetics of Iron(lll)-Hydroxide Sucrose Complex after a Single Intravenous Dose in Healthy Volunteers, ARZNEIMITTEL-FORSCHUNG 46:615-621 (1996).
An excerpt from vol. X of The Oxford English Dictionary (Oxford Univ. Press 1978).
An excerpt from The Concise Oxford Dictionary of Current English 1387 (Della Thompson ed 9th ed. 1995).
*Pharmacosmos A/S* v. *Luitpold Pharma., Inc.*, IPR2015-01490, Paper 54 (P.T.A.B. Jan. 4, 2017).
Nancy Berliner, Disorders of Red Blood Cells, in Cecil Essentials of Medicine (Carpenter et al. eds., 5th ed. 2001).
Jay Umbreit, Iron Deficiency: A Concise Review, Am. J. Hematology 78:225-231 (2005).
Igor Maslovsky, Intravenous Iron in a Primary-Care Clinic, Am. J. Hematology 78:261-264 (2005).
Bo G. Danielson, Structure, Chemistry, and Pharmacokinetics of Intravenous Iron Agents, J. Am. Soc. Nephrol. 15:S93-S98 (2004).
Beckie Michael et al., Sodium Ferric Gluconate Complex in Hemodialysis Patients: Adverse Reactions Compared to Placebo and Iron Dextran, Kidney Int'L 61:1830 1839 (2002).
Steven Fishbane, Refractory Anemia in a Patient With Allergy to Intravenous Iron Drugs, Kidney Int'L 69:1910-1913 (2006).
Beckie Michael et al., Sodium Ferric Gluconate Complex in Haemodialysis Patients: A Prospective Evaluation of Long-Term Safety, Nephrol Dial Transplant 19:1576 1580 (2004).
Ferrlecit® and Venofer® Labels, dated 2002.
Daniel W. Coyne, Sodium Ferric Gluconate Complex in Hemodialysis Patients. II. Adverse Reactions in Iron Dextran-Sensitive and Dextran-Tolerant Patients, Kidney Int'L 63:217-224 (2003).
Steven Fishbane et al., The Safety of Intravenous Iron Dextran in Hemodialysis Patients, Am. J. Kidney Diseases 28(4):529- 534 (1996).
Madhuresh K. Sethi, et al., Significance of Redox Studies on Branched Polysaccharides During Metal Complex Formation, Der Pharma Chemica 9:13-18 (2017).
Jesus M. Frias, et al., Modeling and Parameter Identification of a Maltodextrin DE 12 Drying Process in a Convection Oven, Applied Mathematical Modeling 25:449-462 (2001).
Defendant's Joint Opening Claim Construction Brief. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Dated Aug. 24, 2020.
Defendant's Opening Markman Brief. In the U.S. District Court for the District of New Jersey. Civil Action No. 19-13955. *Vifor (International) AG and American Regent, Inc.*, Plaintiffs, v. *Mylan Laboratories Ltd.* and *Sandoz, Inc.*, Defendants. Filed Aug. 24, 2020.
Declaration of Geert-Jan Boons, Ph.D. in Support of Plaintiffs' Opening Markman Brief. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Filed Aug. 24, 2020.
Declaration of James A. Cowan, Ph.D. in Support of Plaintiffs' Opening Markman Brief. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Filed Aug. 24, 2020.
Opening Expert Declaration of Dr. Daniel Coyne. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Filed Aug. 24, 2020.
Declaration of M. David Weingarten in Support of Plaintiffs' Opening Markman Brief. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Filed Aug. 24, 2020.
Corrected Declaration of Anthony L. Defranco, Ph.D. In the U.S. District Court for the District of New Jersey. Civil Action No. 19-13955. *Vifor (International) AG* and *American Regent, Inc.*, Plaintiffs, v. *Mylan Laboratories Ltd.* and *Sandoz, Inc.*, Defendants. Dated Aug. 24, 2020.
Defendants' Brief in Opposition to Plaintiffs' Motion for Judicial Correction. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 2, 2020. 22 pages.
Declaration of Alexei Demchenko, PhD., In Opposition to Plaintiffs' Motion for Judicial Correction of Claim 1 of U.S. Pat. No. 10,519,252. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 2, 2020. 110 pages.
Declaration of Adam D. Sussman in Support of Defendants' Brief in Opposition to Plaintiffs' Motion for Judicial Correction. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 2, 2020. 3 pages.
Exhibit 1. Declaration Under 37 CFR Section 1.132 of Dr. Erik Phillipp. In re Patent Application of Peter Geisser et al. U.S. Appl. No. 13/835,400, filed Mar. 15, 2013. Dated Feb. 15, 2016. 45 pages.
Exhibit 2. Defendants' Invalidity Contentions Regarding U.S. Patent Nos. 7612109, 7754702, 8895612, 9376505 and 10519252 Made Under Local Patent Rules 3.3 and 3.6. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Mar. 17, 2020. 15 pages.
Exhibit 3. Excerpt from Plaintiffs' Response to Defendants' Invalidity Contentions Regarding US Patent Nos. 7612109, 9376505, 10519252, 7754702 and 8895612. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Jun. 15, 2020. 22 pages.
Exhibit 4. Certified Copy dated Jun. 13, 2019 of original filed Claims of U.S. Appl. No. 11/620,986, filed Jan. 8, 2007, now U.S. Pat. No. 7,754,702. 12 pages.
Exhibit 5. Excerpt from Certified Copy dated Jan. 16, 2020 of File History Wrapper of U.S. Appl. No. 13/835,400, filed Mar. 15, 2013, now U.S. Pat. No. 10,519,252. 39 pages.

(56) References Cited

OTHER PUBLICATIONS

Exhibit 5-A. Excerpt from File History Wrapper of U.S. Appl. No. 13/835,400, filed Mar. 15, 2013, now U.S. Pat. No. 10,519,252. 40 pages.
Exhibit 5-B. Excerpt from File History Wrapper of U.S. Appl. No. 13/835,400, filed Mar. 15, 2013, now U.S. Pat. No. 10,519,252. 47 pages.
Exhibit 5-C. Excerpt from File History Wrapper of U.S. Appl. No. 13/835,400, filed Mar. 15, 2013, now U.S. Pat. No. 10,519,252. 101 pages.
Exhibit 6. Prosecution History of the '252 Patent, Recitations of "3(S)" Chemical Name. 26 pages.
Exhibit 7. U.S. Pat. No. 6587550 B2 issued Jul. 1, 2003 from U.S. Appl. No. 09/783,340, filed Feb. 14, 2001. 9 pages.
Exhibit 8. U.S. Pat. No. 9,120,838 B2 issued Sep. 1, 2015 from U.S. Appl. No. 14/112,830, filed Apr. 18, 2012. 26 pages.
Exhibit 9. Thaburet, Jean-Francois, et al. TEMPO-mediated oxidation of maltodextrins and D-glucose: effect of pH on the selectivity and sequestering ability of the resulting polycarboxylates. Carbohydrate Research 330 (2001) pp. 21-29. 10 pages.
Exhibit 10. Suzukamo, G., et al. C3 Epimerization and Selective C2-C3 Bond Fission of Alkyl Chrysanthemate. Tetrahedron Letters, vol. 25, No. 15, pp. 1595-1598, 1984 Pergamon Press Ltd. Great Britain.
Exhibit 11. Guerinot, Amandine, et al. FeCl3—6H20-catalyzed synthesis of substituted cis-2,6-tetrahydropyrans from—hydroxy allylic derivatives. Tetrahedron. vol. 67 (2011) pp. 5024-5033. 11 pages.
Plaintiffs' Reply Brief in Support of Motion for Judicial Correction. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 13, 2020. 15 pages.
Reply Declaration of Brian M. Stoltz, Ph.D. in Support of Plaintiffs' Motion for Judicial Correction. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 13, 2020. 15 pages.
Reply Declaration of Geert-Jan Boons, Ph.D. in Support of Plaintiffs' Motion for Judicial Correction. United States District Court. District of New Jersey. Civil Action No. 19-13955 (FLW) (DEA) (CONSOLIDATED) *Vifor (International) AG* and *American Regent, Inc.*, Plaintiffs v. *MYLAN Laboratories Ltd.* and *Sandoz Inc.*, Defendants. Dated Nov. 13, 2020. 80 pages.
Reply to the Patentee's Appeal. Appeal No. T1139/19-3.3.01; Opposition in European Patent No. 1973549 (Vifor(International) AG); Opponent:Generics [UK] Limited (07). Filed in the European Patent Office Oct. 2, 2020, 16 pages.
Response to the communication dated May 19, 2020, forwarding the statements setting out the grounds of appeal of the opponents 03, 06, and 07. Appeal No. T1139/19-3.3.01 to Opposition in European Patent No. 1973549 Appellant: Vifor (International) AG; Respondents: Hoffmann Eitle Patent- und Rechtsanwalte, Partnerschaftsgesellschaft mbB, Pharmacosmos Holding A/S,Teva Pharmaceutical Industries Ltd., HGF Limited, STADA Arzneimittel AG, Taylor Wessing LLP, Generics Limited. Filed in the European Patent Office Oct. 2, 2020.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Oct. 2, 2020, 330 pages.
Auxiliary requests during appeals procedure. Appeal No. T1139/19-3.3.01. Amended claims with annotations, filed Sep. 29, 2020 in European Appl. No. 07716309.5/ European Patent No. EP 1973549 (Vifor (International) AG), 145 pages.
Auxiliary requests during appeals procedure. Appeal No. T1139/19-3.3.01. Claims in European Appl. No. 07716309.5/European Patent No. EP 1973549 (Vifor (International) AG), submitted to European Patent Office Sep. 29, 2020, 67 pages.
Letter accompanying subsequently filed items. Filed in European Appl. No. 07716309.5 / European Patent No. EP 1973549 (Vifor (International) AG), submitted to European Patent Office Sep. 29, 2020, 4 pages.
Letter accompanying subsequently filed items. Filed in European Appl. No. 07716309.5 / European Patent No. EP 1973549 (Vifor (International) AG), submitted to European Patent Office Sep. 28, 2020, 1 page.
Letter relating to appeal procedure. Filed in European Appl. No. 07716309.5 / European Patent No. EP 1973549 (Vifor (International) AG), submitted to European Patent Office Sep. 25, 2020, 1 page.
Reply to Appeal. Response to the communication dated May 19, 2020, forwarding the statements setting out the grounds of appeal of the opponents 03, 06, and 07. Appeal No. T1139/19-3.3.01 to Opposition in European Patent No. 1973549; Appellant: Vifor (International) AG; Respondents: Hoffmann Eitle Patent- und Rechtsanwalte, Partnerschaftsgesellschaft mbB, Pharmacosmos Holding A/S,Teva Pharmaceutical Industries Ltd., HGF Limited, STADA Arzneimittel AG, Taylor Wessing LLP, Generics Limited. Filed in the European Patent Office Sep. 29.
Non Patent Literature cited during appeal. Appeal No. T1139/19-3.3.01. European Patent No. EP 1973549 (Vifor (International) AG). New Zealand Data Sheet—Ferrosig Solution for Injection 50 mg/mL.
Non Patent Literature cited during appeal. Appeal No. T1139/19-3.3.01. European Patent No. EP 1973549 (Vifor (International) AG). Single total dose infusion of ferumoxytol (1020 mg in 30 minutes) is an improved method of administration of intravenous iron. Correspondence. AJH. Wiley, pp. E228-E232.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Sep. 28, 2020, 14 pages.
Reply to the Patentee's Appeal. Appeal No. T1139/19-3.3.01; Opposition in European Patent No. 1973549 (Vifor (International) AG); Opponent:Generics [UK] Limited (07). Filed in the European Patent Office Sep. 28, 2020, 15 pages.
Reply to the Patentee's Appeal. Appeal No. T1139/19-3.3.01; Opposition in European Patent No. 1973549 (Vifor (International) AG); Opponent: Teva Pharmaceutical Industries Ltd (03). Filed in the European Patent Office Sep. 17, 2020, 12 pages.
Defendant's Responsive Claim Construction Brief. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Filed electronically in the Court on Sep. 28, 2020. 39 pages.
Plaintiffs Responsive Markman Brief (Redacted) In the United States District Court, District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Sep. 28, 2020. 36 pages.
Responsive Expert Declaration of Daniel Coyne, MD (Redacted). In the United States District Court, District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Sep. 28, 2020. 22 pages.
Fishbane M.D., Steven. Safety in Iron Management. Amer. Jour. Kidney Dis. Vol. 41, No. 6, Supp. 5, Jun. 2003, pp. S16-S26.
Aronoff, George, et al. Iron sucrose in hemodialysis patients: Safety of replacement and maintenance regimens. Kidney International, vol. 66 (2004), pp. 1193-1198.
Bailie, George R., et al. Hypersensitivity reactions and deaths associated with intravenous iron preparations. Nephrol Dial Transplant (2005) 20: 1443-1449 Advance Access publication Apr. 26, 2005.
Funk, Felix, et al. The new generation of intravenous iron: chemistry, pharmacology, and toxicology of ferric carboxymaltose. Arzneimittelforschung 2010: 60 (6a) pp. 345-353.
Declaration of Jieun Lee in Support of Defendants' Responsive Claim Construction Brief. In the United States District Court for the District of New Jersey. Civil Action No. 19-13955. *Vifor (Interna-*

(56) References Cited

OTHER PUBLICATIONS

*tional) AG* and *American Regent, Inc.*, Plaintiffs v. *Mylan Laboratories Ltd.* and *Sandoz, Inc.*, Defendants. Dated Sep. 28, 2020.
Markman Response Exhibit 40. Excerpt from the United States Pharmacopeia (USP 24) The National Formulary (NF 19) Jan. 1, 2000, 28 pages.
Markman Response Exhibit 41. Published International Application No. WO 02/46241 A2 published Jun. 13, 2002 in International Application No. PCT//YUOI/00031 filed Dec. 7, 2001, 34 pages.
Markman Response Exhibit 42. Excerpt from Dorland's Illustrated Medical Dictionary, vol. 27th Edition.
Markman Response Exhibit 43. Excerpt from Stedman's Medical Dictionary, Illustrated in Color, vol. 27th Edition.
Markman Response Exhibit 44. Transcript of Videotaped Deposition of Geert-Jan Boons, Ph.D. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Deposition date Sep. 9, 2020. 217 pages.
Markman Response Exhibit 45. Transcript of Videotaped Deposition of Daniel Coyne, M.D. in the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Deposition date Sep. 11, 2020. 161 pages.
Markman Response Exhibit 46. Chemical structure.
Declaration of M. David Weingarten in Support of Plaintiffs' Responsive Markman Brief. (Redacted) In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Sep. 28, 2020.
Plaintiffs Exhibit A. Transcript of Videotaped Deposition of Daniel Coyne, M.D. (Redacted) In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Deposition date Sep. 11, 2020. 77 pages.
Plaintiffs Exhibit B. Transcript of Virtual Videotaped Deposition of Anthony L. DeFranco Ph.D. (Redacted) In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Deposition date Sep. 14, 2020. 74 pages.
Plaintiffs Exhibit D. van Zyl-Smit, R., et al. Experience with the Use of an Iron Polymaltose (Dextrin) Complex Given by Single Total Dose Infusion to Stable Chronic Haemodialysis Patients. Nephron 2002;92:316-323 Accepted Dec. 12, 2007. 9 pages.
Plaintiffs Exhibit E. Kennedy, J.F et al. Maltodextrins. Excerpt from Handbook of Starch Hydrolysis Products and their Derivatives. First Edition. 1995. 7 pages.
Plaintiffs Exhibit F. New Search [Code of Federal Regulations][Title 2i;vol. 3][-Revised as of Apr. 1, 2015] [Cite: 21CFR184.1444] Title 21-FOOD and Drugs Chapter 1 Food and Drug Administration Department of Health and Human Services Subchapter B-Food for Human Consumption (continued) Part 184—Direct Food Substances Affirmed as Generally-Recognized as Safe Subpart B-Listing of Specific Substances Affirmed as GRAS Sec.184.1444. Maltodextrin. 3 pages.
Plaintiffs Exhibit G. Dokic, P., et al. Molecular characteristics of maltodextrins and rheological behaviour of diluted and concentrated solutions. Colloids and Surfaces A: Physicochemical and Engineering Aspects 141 ( 1998) 435-440.
Plaintiffs Exhibit M. Published European Patent Application No. EP 3339329 A1 published Jun. 27, 2018 from European Patent Application No. 16206398.6 filed on Dec. 22, 2016.
Plaintiffs Exhibit N. Transcript of Videotaped Deposition of Geert-Jan Boons, Ph.D. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Deposition date Sep. 9, 2020. 100 pages.
Plaintiffs Exhibit O. European Patent No. EP 1231903 B1 issued on Jan. 11, 2006 from European Patent Application No. 00987277.1 filed Nov. 21, 2000. Proprietor: Sandoz AG. 11 pages.
Plaintiffs Exhibit Q. International Patent Publication No. WO 2016/151367 A1 published Sep. 29, 2016 from International Patent Application No. PCT/IB15/53305 filed on May 6, 2015. Assignee: Suven Life Sciences Limited (IN). 24 pages.
Plaintiffs Exhibit R. International Patent Publication No. WO 2016/181195 A1 published Nov. 17, 2016 from International Patent Application No. PCT/IB15/54655 filed on May 8, 2015. Assignee: Suven Life Sciences Limited (IN). 22 pages.
Plaintiffs Exhibit S. International Patent Publication No. WO 2011/055374 A2 published May 12, 2011 from International Patent Application No. PCT/IN09/00624 filed on Nov. 4, 2009. Assignee: Symed Labs Limited (IN). 22 pages.
Letter from Plaintiffs Counsel to the Honorable Freda L. Wilson, United States District Court, District of New Jersey. RE: Vifor (International) AG, et al. v. Mylan Laboratories Ltd., et al. Civil Action No. 19-13955 (FLW) (DEA) (CONSOLIDATED). Dated Oct. 5, 2020. 1 page.
Letter from Defendant's Counsel to the Honorable Freda L. Wilson, United States District Court, District of New Jersey. RE: *Vifor (International) AG*, et al. v. *Mylan Laboratories Ltd.*, et al. Civil Action No. 19-13955 (FLW) (DEA) (CONSOLIDATED). Dated Oct. 9, 2020. 3 pages.
Plaintiffs Notice of Motion for Judicial Correction. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Oct. 9, 2020. 2 pages.
Plaintiffs Briefs in Support of Motion for Judicial Correction. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Oct. 9, 2020. 13 pages.
Declaration of Brian Stoltz, Ph.D. in Support of Plaintiffs' Motion for Judicial Correction of Claim 1 Of U.S. Pat. No. 10,519,252. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Oct. 9, 2020. 66 pages.
Declaration of Erik Philipp, Ph.D. in Support of Plaintiffs' Motion for Judicial Correction of Claim 1 Of U.S. Pat. No. 10,519,252. In the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Oct. 9, 2020. 5 pages.
Declaration of William P. Deni, Jr. in Support of Plaintiffs' Motion for Judicial Correction. in the United States District Court for the District of New Jersey. Civil Action No. 19-13955. *Vifor (International) AG* and *American Regent, Inc.*, Plaintiffs v. *Mylan Laboratories Ltd.* and *Sandoz, Inc.*, Defendants. Dated Oct. 9, 2020. 2 pages.
Opening Claim Construction Expert Declaration of Todd L. Lowary, Ph.D. United States District Court, District of Newjersey. *American Regent, Inc.*, Plaintiff v. *Pharmacosmos Therapeutics Inc.* and *Pharmacosmos A/S*, Defendants. Civil Action No. 3:20-1350 (BRM) (LHG). Filed Apr. 5, 2021.
Opening Claim Construction Expert Declaration of Dr. Daniel Coyne. United States District Court, District of Newjersey. *American Regent, Inc.*, Plaintiff, v. *Pharmacosmos Therapeutics Inc.* and *Pharmacosmos A/S*, Defendants. Civil Action No. 20-1350 (BRM) (LHG). Filed Apr. 5, 2021.
Plaintiff American Regent'S Opening Claim Construction Brief. United States District Court, District of Newjersey. *American Regent, Inc.*, Plaintiff, v. *Pharmacosmos Therapeutics Inc.* and *Pharmacosmos A/S*, Defendants. Civil Action No. 20-1350 (BRM) (LHG). Filed Apr. 5, 2021.
Defendants Pharmacosmos A/S and Pharmacosmos Therapeutics Inc.'S Opening Claim Construction Brief. in the United States

(56) References Cited

OTHER PUBLICATIONS

District Court for the District of New Jersey. American Regent, Inc., Plaintiff-Counter-Defendant, v. Pharmacosmos Therapeutics Inc. and Pharmacosmos A/S, Defendants-Counter-Plaintiffc. Civil Action No. 20-1350 (Brm) (Lhg) Filed Apr. 5, 2021.
Declaration of Guillermo C. Artiles in Support of Defendants' Opening Claim Construction Brief. in the United States District Court for the District of Newjersey. *American Regent, Inc.*, Plaintiff-Counter-Defendant, v. *Pharmacosmos Therapeutics Inc.* and *Pharmacosmos A/S*, Defendants-Counter-Plaintiffs. Civil Action No. 20-1350 (BRM) (LHG). Filed Apr. 5, 2021.
Declaration of Robert G. Hamilton in Support of Defendants' Opening Claim Construction Brief. in the United States District Court for the District of Newjersey. *American Regent, Inc.*, Plaintiff-Counter-Defendant, v. *Pharmacosmos Therapeutics Inc.* and *Pharmacosmos A/S*, Defendants-Counter-Plaintiffs. Civil Action No. 20-1350 (BRM) (LHG). Filed Apr. 5, 2021.
Declaration of Parastoo Azadi Ph.D. in Support of Defendants' Opening Claim Construction Brief. in the United States District Court for the District of Newjersey. *American Regent, Inc.*, Plaintiff-Counter-Defendant, v. *Pharmacosmos Therapeutics Inc.* and *Pharmacosmos A/S*, Defendants-Counter-Plaintiffs. Civil Action No. 20-1350 (BRM) (LHG). Filed Apr. 5, 2021.
Letter dated Mar. 10, 2021 from William P. Deni, Jr., Director, Gibbons P.C., Newark, NJ to the Honorable Freda L. Wolfson, C.U.S.D.J., United States District Court, District of New Jersey, RE: *Vifor (International) AG*, et al. v. *Mylan Laboratories Ltd.* and *Sandoz Inc.*, Civil Action No. 19-13955 (FLW) (DEA) (CONSOLIDATED).
Exhibit A—Dec. 27, 2006 (Revised Feb. 2021) Statement On a Nonproprietary Name Adopted By the USAN Council: USAN Ferric Carboxymaltose.
Exhibit B—Dec. 27, 2006 (Revised Nov. 2016) Statement On a Nonproprietary Name Adopted By the USAN Council: USAN Ferric Carboxymaltose.
Exhibit C—USAN 2020 Winter Meeting minutes of the USAN Council—Meeting of Dec. 4, 2020 virtually via WebEx. Retrieved from the internet on Feb. 8, 2021 from URL https://www.ama-assn.org/about/united-states-adopted-names/usan-council.
Exhibit D—USAN Procedure for USAN Name Selection—Retrieved from the internet on Feb. 8, 2021 from URL https://www.ama-assn.org/about/united-states-adopted-names/procedure-usan-name-selection.
Letter dated Feb. 8, 2021 from William P. Deni, Jr., Director, Gibbons P.C., Newark, NJ to the Honorable Freda L. Wolfson, C.U.S.D.J., United States District Court, District of New Jersey, RE: *Vifor (International) AG*, et al. v. *Mylan Laboratories Ltd.* and *Sandoz Inc.*, Civil Action No. 19-13955 (FLW) (DEA) (CONSOLIDATED).
Letter dated Mar. 2, 2021 from Eric I. Abraham, Hill Wallack, LLP to the Honorable Freda L. Wolfson, C.U.S.D. J., United States District Court, District of New Jersey, RE: *Vifor (International) AG*, et al. v. *Mylan Laboratories Ltd.* and *Sandoz Inc.*, Civil Action No. 19-13955 (FLW) (DEA) (CONSOLIDATED).
Exhibit 3—Form D—USAN Revised Application dated Oct. 29, 2020 for SS-40 Ferric Carboxymaltose.
Exhibit 2—USPTO Non-Final Office Action dated Jan. 13, 2021 issued in U.S. Appl. No. 17/087,132, filed Nov. 2, 2020.
Reply Expert Report of Dr. Michael Auerbach, Md, FACP and Exhibit A (CV). United States District Court—District of New Jersey. *Vifor (International) AG and American Regent, Inc.*, Plaintiffs v. *Mylan Laboratories Ltd.* and *Sandoz, Inc.*, Defendants. Civil Action No. 19-13955 (FLW) (DEA) (CONSOLIDATED). Received Aug. 3, 2021.
Reply Expert Report of Dr. John Glaspy. United States District Court—District of New Jersey. *Vifor (International) AG* and *American Regent, Inc.*, Plaintiffs v. *Mylan Laboratories Ltd.* and *Sandoz, Inc.*, Defendants. Case No. 3.19-cv-13955 FLW-DEA (CONSOLIDATED). Received Aug. 3, 2021.
Reply Expert Report of Ivan T. Hoffman. United States District Court—District of New Jersey. *Vifor (International) AG* and *American Regent, Inc.*, Plaintiffs v. *Mylan Laboratories Ltd.* and *Sandoz, Inc.*, Defendants. Case No. 3.19-cv-13955 FLW-DEA (CONSOLIDATED). Received Aug. 3, 2021.
Reply Expert Report of James E. Kipp, Ph.D. United States District Court—District of New Jersey. *Vifor (International) AG* and *American Regent, Inc.*, Plaintiffs v. *Mylan Laboratories Ltd.* and *Sandoz, Inc.*, Defendants. Case No. 3.19-cv-13955 FLW-DEA (CONSOLIDATED). Received Aug. 3, 2021.
Reply Expert Report of Jerome Lewis, Ph. D. United States District Court—District of New Jersey. *Vifor (International) AG* and *American Regent, Inc.*, Plaintiffs v. *Mylan Laboratories Ltd.* and *Sandoz, Inc.*, Defendants. Case No. 3.19-cv-13955 FLW-DEA (CONSOLIDATED). Received Aug. 3, 2021.
Letter of Supplement Approval for Injectafer—Highlights of Prescribing Information package insert. U.S. Food and Drug Administration to American Regent, Inc. U.S. Food & Drug Administration, Silver Springs, MD 20993. Received Aug. 3, 2021.
Auerbach, et al., "Intravenous ferric derisomaltose for the treatment of iron deficiency anemia," Am. J. Hematol., 1-8 (2021).
Barresi, et al., "Maltooligosaccharides from Corn," in Oligosaccharides in Food and Agriculture 182-95 (ACS Symposium Series 2003).
Durup, et al., "Evaluation of the reported rates of hypersensitivity Yeactions associated with iron dextran and ferric carboxymaltose based on global data from VigiBaseTM and IQVIATM MIDAS® over a ten-year period from 2008 to 2017," Expert Rev. Hematol. 2020.
FDA, Draft Guidance on Ferric Carboxymaltose (Apr. 2016), available at https://www.accessdata.fda.gov/drugsatfda_docs/psg/FERRIC%20CARBOXYMALTOSE_injection_RLD%20203565_RC04-16.pdfn.
Freter, et al., "Pulmonary Edema: Atypical Anaphylactoid Reaction to Intravenous Iron Dextran," Am. J. Nephrol., 17:477-79 (1997).
Vifor's Response to Communication of Notices of Opposition dated Oct. 10, 2013 in Opposition to EP 2287204.
K. Lloyd & P. Williams, "Reactions to Total Dose Infusion of Iron Dextran in Rheumatoid Arthritis," British Med. J., 2:323 (1970).
Iain C. Macdougall, "Strategies for Iron Supplementation: Oral Versus Intravenous," Kidney Int'l, 55:S-61-S-66 (1999).
Drugs@FDA: FDA Approved Drug Products, "Proferdex".
R. Smith & A. Martell, Critical Stability Constants, vol. 2 Amines (Plenum Press 1975).
R. Stockman, "The Treatment of Chlorosis by Iron and Some Other Drugs," British Med. J., 1:881 (1893).
Furugouri, "Iron Binding Substances in the Intestinal Mucosa of Neonatal Piglets," J. Nutr. 107:487-494 (1977) (PTX-1446 at 2) (Ex. B).
Soskel et al., "A Copper-Deficient, Zinc-Supplemented Diet Produces Emphysema in Pigs," Am. Rev. Respir. Dis. 126:316-325 (1982) (PTX-1451 at 1) (Ex. C).
Silvestri et al., "The Serine Protease Matriptase-2 (TMPRSS6) Inhibits Hepcidin Activation by Cleaving Membrane Hemojuvelin," Cell Metabolism 8:502-511 (2008) (PTX-1449 at 9) (Ex. E).
Janet Amundson Romich, Fundamentals of Pharmacology for Veterinary Technicians 2d Ed. (2010) (PTX-1445 at 3) (Ex. F).
Lisa A. Martini-Johnson, Applied Pharmacology for Veterinary Technicians 6th Ed. (2021) (PTX-1443 at 3) (Ex. G).
1996 Pigdex 100 Label (PTX-1448) (Ex. H).
Ueberschär et al., "Histological studies after subcutaneous or intramuscular injections of high molecular weight iron polysaccharides in piglets,)" Can. Vet. J. 9(10): 236-37 (1968) (abstract) (PTX-1444) (Ex. I).
Eugene A. Gardner, "The Effects of Erythropoietin, Dibenzyline, and Iron Dextran on the Hemogram of Doe and Fetal Rabbits" (1971) (M.S. Thesis, S.D. State Univ.) (PTX-1460) (Ex. J).
Mohamed A. Amer, "Effect of Supplemental Copper and Vitamin E on the Chemical and Physical Characteristics of Swine Depot Lipids" (1972) (Ph.D. Thesis, McGill Univ.) (PTX-1461).

(56) References Cited

OTHER PUBLICATIONS

Certified Translation of PTX-1463 (Ex. M), E. Huber, "Etude des effets de Quadrex® sur la croissance, le taux d'hémoglobine et l'hématocrite du porcelet," Schweiz. Arch. Tierheilk. 121: 479-483 (1979) (PTX-1462) (Ex. L).
Tully, "Psittacine Therapeutics," Veterinary Clinics of North America: Exotic Animal Practice 3(1):59-90 (2000) (PTX-1464) (Ex. N).
Exhibit C (Lee, et al., "Ferritin From Different Organs of Man, Rat, Rabbit and Pig," Comp. Biochem. Physiol., 39B:325-333 at 327 (1971) (DTX-2910)).
Hoffren, et al., "The Effect of Iron Injection at Different Ages on Baby Pig Haemoglobin," Clinical Vet. Lab., pp. 106-111 at 107 (Apr. 7, 1964) (DTX-2913) (Ex. D).
Williams, et al., "Role of Copper in Mitochondrial Iron Metabolism," Blood, 48(1):77-85 at 84 (Jul. 1976) (DTX-2912) (Ex. E).
Deiss, et al., "Ferritin Metabolism in Reticulated-Siderocytes," J. Clin. Invest., 49:517-523 at 517 (1970) (DTX-2907) (Ex. G).
Deiss et al., "Experimental Production of Siderocytes," J. Clin.I Investigation, 45(3):353-364 at 364 (1966) (DTX-2909) (Ex. H).
Ferinject product label in Europe (Summary of Product Characteristics of Ferinject (Ferric Carboxymaltose). United Kingdom. Rev. Jun. 2012.
E. Frieden, "Ceruloplasmin, A Link Between Copper and Iron Metabolism," Bioinorganic Chemistry (Dessy, R et al.), Ch. 14, pp. 292-321 at 306 (1971) (DTX-2908) (Ex. I).
E. Letendre, "Regulation of Iron Metabolism During Neisseria Meningitidis Infection in Mice," McGill University (Feb. 22, 1984) (DTX-2915) (Ex. J), at 39.
Windels, et al., "Injectable Iron as a Preventative for Nutritional Anemia in the Young Pig," Technical Bulletin 250, Univ, of Minn. (Aug. 1966) (DTX-2916) (Ex. K) at 6.
The Florida Cattleman and Livestock Journal Advertisement (Dec. 1973) (DTX-2906) (Ex. L).
Qunibi, Qajeh Y. The efficacy and safety of current intravenous iron preparations for the management of iron-deficiency anaemia: a review. Arzneimittelforschung 2010; 60 (6a): 399-412.
Bundesgesundheitsamt (BGA). German marketing approval for Ferrum Hausmann. Dated Apr. 4, 1978.
La Direccion del Servicio Quimico Farmaceutico Nacional. Bolivian marketing approval for Ferrum Hausmann. Dated Jan. 25, 1960.
International Nonproprietary Names for Pharmaceutical Substances (INN). Who Drug Information, vol. 22, No. 1, 2008.
Plaintiffs Trial Brief. United States District Court—District of New Jersey. Civil Action No. 19-13955 (FLW) (DEA) (Consolidated). *Vifor (International) AG* and *American Regent, Inc.*, Plaintiffs v. *Mylan Laboratories Ltd.* and *Sandoz, Inc.*, Defendants. Dated Jul. 5, 2021.
Defendants Joint Trial Brief. United States District Court—District of New Jersey. Civil Action No. 19-13955 (FLW) (DEA) (Consolidated). *Vifor (International) AG* and *American Regent, Inc.*, Plaintiffs v. *Mylan Laboratories Ltd.* and *Sandoz, Inc.*, Defendants. Dated Jul. 2021.
William P. Deni, Jr., Gibbons PC, Letter to Hon. Freda L. Wolfson, U.S.C.D.J., United States District Court, District of New Jersey. RE: Civil Action No. 19-13955. *Vifor (International) AG* and *American Regent, Inc.*, Plaintiffs v. *Mylan Laboratories Ltd.* and *Sandoz, Inc.*, Defendants. Dated Jul. 29, 2021.
Arnold B. Calmann, Saiber Attorneys at Law, Letter to Hon. Freda L. Wolfson, U.S.C.D.J., United States District Court, District of New Jersey. RE: Civil Action No. 19-13955. *Vifor (International) AG* and *American Regent, Inc.*, Plaintiffs v. *Mylan Laboratories Ltd.* and *Sandoz, Inc.*, Defendants. Dated Jul. 23, 2021.
Protest pursuant to section 34.1 of the patent act and under section 12 of the patent rules, dated Sep. 7, 2021, filed in the Canadian IP Office in corresponding Canadian Patent Application No. 2953964 for Methods and Compositions for Administration of Iron.
Courtesy—Acknowledgment of Protest to Agent, Common Representative, or Applicant, issued by the Canadian IP Office in corresponding Canadian Patent Application No. 2953964 for Methods and Compositions for Administration of Iron. Dated Oct. 13, 2021.
Stipulation and Order of Dismissal as to Mylan Laboratories Ltd. United States District Court. District of New Jersey. *Vifor (International) AG* and *American Regent, Inc.*, Plaintiffs v. *Mylan Laboratories Ltd.* and *Sandoz, Inc.*, Defendants. Civil Action No. 19-13955 (FLW) (DEA) (CONSOLIDATED). Order Dated Dec. 15, 2021.
Stipulation and Order of Dismissal as to Sandoz, Inc. United States District Court. District of New Jersey. *Vifor (International) AG* and *American Regent, Inc.*, Plaintiffs v. *Mylan Laboratories Ltd.* and *Sandoz, Inc.*, Defendants. Civil Action No. 19-13955 (FLW) (DEA) (CONSOLIDATED). Order Dated Dec. 21, 2021.
Information for use: Information for patients Ferinject 50 mg iron/ml solution for injection and infusion Iron carboxymaltose. https://viforpharma-pro.de/sites/default/files/2020-07/Gebrauchsinformation%20Ferinject%202020_07.pdf (accessed Sep. 17, 2021) English translation provided (Google translate).
Wikipedia (English edition): Dextrin (Last edited Jul. 31, 2021, 17:03 (UTC), access date Sep. 13, 2021, 14:51)
TO-DAY'S DRUGS, British Medical Journal, Feb. 17, 1962, p. 468.
Ali, Omar. Commissioning cost-effective delivery of intravenous iron. Prescriber vol. 5, Oct. 2011, pp. 43-46.
BeMiller, J N. "Dextrins", Encyclopedia of Food Sciences and Nutrition, 2nd Edition, 2003, Elsevier Science Ltd; pp. 1773-1775. Purdue University, West Lafayette, IN, USA.
"American Regent's Injectafer (Ferric Carboxymaltose Injection) Now the Fastest Growing IV Iron in United States" Business Wire, Jul. 15, 2014. https://www.businesswire.com/news/home/20140715006480/en/American-Regent%E2%80%99s-Injectafer%C2%AE-Ferric-Carboxymaltose-Injection-Now-the-Fastest-Growing-IV-Iron-in-United-States (access date Sep. 17, 2021).
Auerbach, M. and Ballard, H., Clinical Use of Intravenous Iron: Administration, Efficacy, and Safety. Hematology 2010, p. 341.
Thiel, Holger et al.: Anästhesiologisohe Pharmakotherapie, vol. 3, Revised Edition, Georg Thieme Verlag, Stuttgart, 2014, pp. 86-87. English translation provided (Google translate).
Dextran. Römpp, 10th Edition, 1997. English translation provided (Google translate).
Collins, P.M, "Dictionary of Carbohydrates," Springer Science + Business Media Dordrecht, 1998, pp. 251-252 and 494.
"Dextrine" Excerpt from online encyclopedia Wikipedia. Retrieved from website URL: https://de.wikipedia.org/w/index.php?title=Dextrine&oldid=194706387 on Dec. 7, 2019. English translation provided (Google translate).
Maltodextrin, Römpp, 10th Edition, 1997. English translation provided (Google translate).
Bailie, George R. Arzneimittelforschung 2010; 60(63): 386-398.
Pugh-Clarke K., Cooper L., Turner J., Fermin J., An Evidence-Based Approach to Anaemia Management in Predialysis Chronic Kidney Disease, Journal of Renal Care 35(52); (2009), pp. 29-31.
Tagboto S., Cropper L., Turner J., Pugh-Clarke, K. "The efficacy of a single dose of intravenous ferric oarboxymaltose (Ferinjeot®) on anaemia in a pre-dialysis population of chronic kidney disease patients", Journal of Renal Care 35(1), (2009), pp. 18-22.
Bailie, George R. Breaking New Ground in Intravenous Iron Therapy. European Haematology (2008), pp. 58-60.
Dextrin, Römpp, 10th Edition, 1997. English translation provided (Google translate).
Bolger, A., et al. "Intravenous Iron Alone forthe Treatment of Anemia in Patients with Chronic Heart Failure," Journal ofthe American College of Cardiology, vol. 48, No. 6, 2006. American College of Cardiology Foundation. pp. 1225-1227.
Kearsley, M.W. et al., "Handbook of Starch Hydrolysis Products and their Derivatives", Springer Science + Business Media, 1995, pp. 65-68.

\* cited by examiner

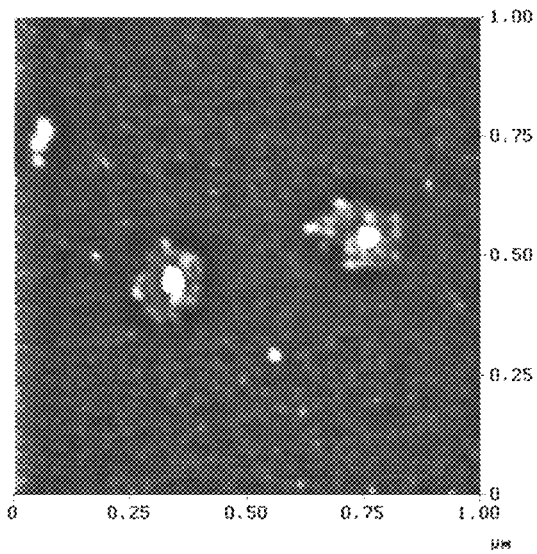 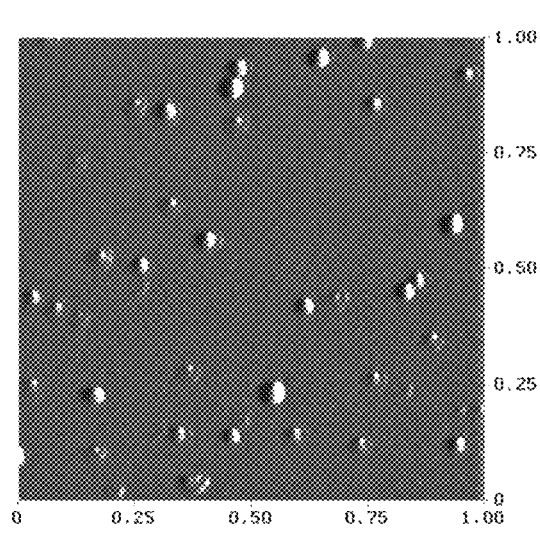
FIG. 1A  FIG. 1B
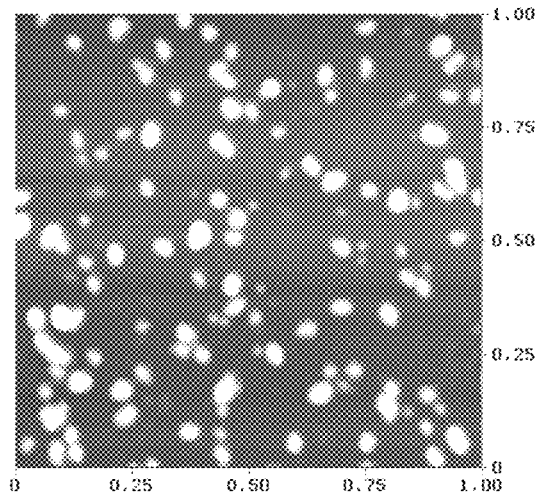
FIG. 1C

METHODS AND COMPOSITIONS FOR ADMINISTRATION OF IRON

CROSS-REFERENCE TO RELATED APPLICATIONS

This application is a continuation of U.S. application Ser. No. 15/958,930, filed Apr. 20, 2018, to Mary Jane Helenek, Marc L. Tokars and Richard P. Lawrence, which is a divisional of U.S. application Ser. No. 14/683,415, filed Apr. 10, 2015, to Mary Jane Helenek, Marc L. Tokars and Richard P. Lawrence, which is a continuation of U.S. application Ser. No. 13/847,254, filed Mar. 19, 2013, to Mary Jane Helenek, Marc L. Tokars and Richard P. Lawrence, which is a continuation of U.S. application Ser. No. 12/787,283, now issued as U.S. Pat. No. 8,431,549, filed May 25, 2010, to Mary Jane Helenek, Marc L. Tokars and Richard P. Lawrence, which is a continuation of U.S. application Ser. No. 11/620,986, now issued as U.S. Pat. No. 7,754,702, filed Jan. 8, 2007, to Mary Jane Helenek, Marc L. Tokars and Richard P. Lawrence, which claims the benefit of priority to U.S. Provisional Application No. 60/757,119, filed Jan. 6, 2006, to Mary Jane Helenek, Marc L. Tokars and Richard P. Lawrence. The subject matter of each of the above-noted U.S. Applications and Patents is incorporated by reference in its entirety.

This application also is a continuation of U.S. application Ser. No. 14/683,415, filed Apr. 10, 2015, to Mary Jane Helenek, Marc L. Tokars and Richard P. Lawrence, which is a continuation of U.S. application Ser. No. 13/847,254, filed Mar. 19, 2013, to Mary Jane Helenek, Marc L. Tokars and Richard P. Lawrence, which is a continuation of U.S. application Ser. No. 12/787,283, now issued as U.S. Pat. No. 8,431,549, filed May 25, 2010, to Mary Jane Helenek, Marc L. Tokars and Richard P. Lawrence, which is a continuation of U.S. application Ser. No. 11/620,986, now issued as U.S. Pat. No. 7,754,702, filed Jan. 8, 2007, to Mary Jane Helenek, Marc L. Tokars and Richard P. Lawrence, which claims the benefit of priority to U.S. Provisional Application No. 60/757,119, filed Jan. 6, 2006, to Mary Jane Helenek, Marc L. Tokars and Richard P. Lawrence. The subject matter of each of the above-noted U.S. Applications and Patents is incorporated by reference in its entirety.

FIELD OF THE INVENTION

The present invention generally relates to treatment of iron-related conditions with iron carbohydrate complexes.

BACKGROUND

Parenteral iron therapy is known to be effective in a variety of diseases and conditions including, but not limited to, severe iron deficiency, iron deficiency anemia, problems of intestinal iron absorption, intestinal iron intolerance, cases where regular intake of an oral iron preparation is not guaranteed, iron deficiency where there is no response to oral therapy (e.g., dialysis patients), and situations where iron stores are scarcely or not at all formed but would be important for further therapy (e.g., in combination with erythropoietin) (Geisser et al., (1992) *Arzneimittelforschung* 42(12), 1439-1452). There exist various commercially available parenteral iron formulations. But many currently available parenteral iron drugs, while purportedly effective at repleting iron stores, have health risks and dosage limitations associated with their use.

Currently available parenteral iron formulations approved for use in the U.S. include iron dextran (e.g., InFed®, Dexferrum®), sodium ferric gluconate complex in sucrose (Ferrlecit®), and iron sucrose (Venofer®). Although serious and life-threatening reactions occur most frequently with iron dextran, they are also known to occur with other parenteral iron products. In addition, non-life threatening reactions such as arthralgia, back pain, hypotension, fever, myalgia, pruritus, vertigo, and vomiting also occur. These reactions, while not life-threatening, often preclude further dosing and therefore iron repletion.

Iron dextran, the first parenteral iron product available in the United States (US), has been associated with an incidence of anaphylactoid-type reactions (i.e., dyspnea, wheezing, chest pain, hypotension, urticaria, angioedema). (See generally, Fishbane (2003) *Am. J. Kidney Dis.* 41(6, 5 Suppl): S18-526 and Landry et al. (2005) *Am. J. Nephrol.* 25:400-410, 407). This high incidence of anaphylactoid reactions is believed to be caused by the formation of antibodies to the dextran moiety. Other parenteral iron products (e.g., iron sucrose and iron gluconate) do not contain the dextran moiety, and the incidence of anaphylaxis with these products is markedly lower (Fishbane (2003) *Am. J. Kidney Dis.* 41(6, 5 Suppl): S18-S26; Geisser et al. (1992) *Arzneimittelforschung* 42(12): 1439-52). However, the physical characteristics of, for example, iron gluconate and iron sucrose lead to dosage and administration rate limitations. Negative characteristics include high pH, high osmolarity, low dosage limits (e.g., maximum 500 mg iron once per week, not exceeding 7 mg iron/kg body weight), and the long duration of administration (e.g., 100 mg iron over at least 5 minutes as an injection; 500 mg iron over at least 3.5 hours as a drip infusion). Furthermore, injectable high molecular mass substances produce more allergic reactions than the corresponding low molecular mass substances (Geisser et al. (1992) *Arzneimittelforschung* 42:1439-1452).

Ferumoxytol is a newer parenteral iron formulation but limited information is available as to its efficacy and administration. (See e.g., Landry et al. (2005) *Am. J. Nephrol.* 25:400-410, 408; Spinowitz et al. (2005) *Kidney Intl.* 68:1801-1807; and U.S. Pat. No. 6,599,498).

Various pharmacokinetic studies suggest that doses of iron complexes higher than 200 mg of iron are generally unsuitable and that the conventional therapy model prescribes repeated applications of lower doses over several days. (See Geisser et al. (1992) *Arzneimittelforschung* 42:1439-1452). For example, to achieve iron repletion under current therapy models, a total dose of 1 g typically requires 5 to 10 sessions over an extended period of time. These delivery modes incur significant expense for supplies such as tubing and infusate, costly nursing time, multiple administrations, and patient inconvenience.

SUMMARY OF THE INVENTION

Among the various aspects of the present invention is the provision of a method of treatment of iron-associated diseases, disorders, or conditions with iron formulations. Briefly, therefore, the present invention is directed to use of iron carbohydrate complexes that can be administered parenterally at relatively high single unit dosages, thereby providing a safe and efficient means for delivery of a total dose of iron in fewer sessions over the course of therapeutic treatment.

The present teachings include methods of treating a disease, disorder, or condition characterized by iron deficiency or dysfunctional iron metabolism through the administration of at least 0.6 grams of elemental iron via a single unit dosage of an iron carbohydrate complex to a subject that is in need of such therapy.

In various embodiments, the method treats anemia. In some embodiments, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents. In some aspects, the anemia is anemia of chronic disease, such as rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia. In some embodiments, the anemia is due to impaired iron absorption or poor nutrition, such as anemia associated with Crohn's Disease; gastric surgery; ingestion of drug products that inhibit iron absorption; and chronic use of calcium. In various embodiments, the method treats restless leg syndrome; blood donation; Parkinson's disease; hair loss; or attention deficit disorder.

In various embodiments, the single dosage unit of elemental iron is between at least about 0.6 grams and 2.5 grams. In some embodiments, the single dosage unit of elemental iron is at least about 0.7 grams; at least about 0.8 grams; at least about 0.9 grams; at least about 1.0 grams; at least about 1.1 grams; at least about 1.2 grams; at least about 1.3 grams; at least about 1.4 grams; at least about 1.5 grams; at least about 1.6 grams; at least about 1.7 grams; at least about 1.8 grams; at least about 1.9 grams; at least about 2.0 grams; at least about 2.1 grams; at least about 2.2 grams; at least about 2.3 grams; at least about 2.4 grams; or at least about 2.5 grams.

In various embodiments, the single dosage unit of elemental iron is administered in about 15 minutes or less. In some embodiments, the single dosage unit of elemental iron is administered in about 10 minutes or less, about 5 minutes or less, or about 2 minutes or less.

In various embodiments, the subject does not experience a significant adverse reaction to the single dosage unit administration.

In various embodiments, the iron carbohydrate complex has a pH between about 5.0 to about 7.0; physiological osmolarity; an iron core size no greater than about 9 nm; a mean diameter particle size no greater than about 35 nm; a blood half-life of between about 10 hours to about 20 hours; a substantially non-immunogenic carbohydrate component; and substantially no cross reactivity with anti-dextran antibodies.

In various embodiments, the iron carbohydrate complex contains about 24% to about 32% elemental iron; contains about 25% to about 50% carbohydrate; has a molecular weight of about 90,000 daltons to about 800,000 daltons, or some combination thereof.

In various embodiments, the iron carbohydrate complex is an iron monosaccharide complex, an iron disaccharide complex, or an iron polysaccharide complex. In some embodiments, the iron carbohydrate complex is iron carboxymaltose complex, iron mannitol complex, iron polyisomaltose complex, iron polymaltose complex, iron gluconate complex, iron sorbitol complex, or an iron hydrogenated dextran complex. In some embodiments, the iron carbohydrate complex is an iron polyglucose sorbitol carboxymethyl ether complex. In some preferred embodiments, the iron carboxymaltose complex contains about 24% to about 32% elemental iron, about 25% to about 50% carbohydrate, and is about 100,000 daltons to about 350,000 daltons. In some preferred embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between 5 and 20, and when a mixture of several maltodextrins is applied, the dextrose equivalent lies between 5 and 20 and the dextrose equivalent of each individual maltodextrin contained in the mixture lies between 2 and 20. In some preferred embodiments, the iron carboxymaltose complex has a chemical formula of $[FeO_x (OH)_y, (H_2O)_z]_n [\{(C_6H_{10}O_5)_m (C_6H_{12}O_7)\}_1]_k$, where n is about 103, m is about 8.1 is about 11, and k is about 4; contains about 28% elemental iron; and has a molecular weight of about 150,000 Da. In some preferred embodiments, the iron carboxymaltose complex is polynuclear iron (III)-hydroxide 4(R)-(poly-(1→4)-O-α-D-glucopyranosyl)-oxy-2(R),3(R),5(R),6-tetrahydroxy-hexanoate.

In various embodiments, the iron carbohydrate complex comprises an iron core with a mean iron core size of no greater than about 9 nm. In some embodiments, the mean iron core size is at least about 1 nm but no greater than about 9 nm; at least about 3 nm but no greater than about 7 nm; or at least about 4 nm but not greater than about 5 nm.

In various embodiments, the mean size of a particle of the iron carbohydrate complex is no greater than about 35 nm. In some embodiments, the particle mean size is no greater than about 30 nm. In some embodiments, the particle mean size is no greater than about 25 nm. In some embodiments, the particle mean size is no greater than about 20 nm; no greater than about 15 nm; no greater than about 10 nm; or at least about 6 nm but no greater than about 7 nm.

In various embodiments, the iron carbohydrate complex is administered parenterally, for example intravenously or intramuscularly. In some embodiments, the iron carbohydrate complex is intravenously infused. In certain embodiments, the single unit dose of iron carbohydrate complex is intravenously infused at a concentration of about 1000 mg elemental iron in about 200 ml to about 300 ml of diluent, for example, about 250 ml of diluent or about 215 ml of diluent. In some embodiments, the iron carbohydrate complex is intravenously injected as a bolus. In certain embodiments, the iron carbohydrate complex is intravenously injected as a bolus at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 500 mg elemental iron in less than about 10 ml diluent.

In various embodiments, the method also includes a second administration of the iron carbohydrate complex upon recurrence of at least one symptom of the treated disease, disorder, or condition.

In various embodiments, the method also includes a second administration of the iron carbohydrate complex after 1 day to 12 months after the first administration.

In a preferred embodiment, the method of treating a disease, disorder, or condition characterized by iron deficiency or dysfunctional iron metabolism comprises intravenously administering to a subject in need thereof an iron carboxymaltose complex in a single dosage unit of at least about 1000 mg of elemental iron in about 200 ml to about 300 ml of diluent in about 5 minutes or less; wherein the iron carboxymaltose complex comprises an iron core with a mean iron core size of at least about 1 nm but no greater than about 9 nm; mean size of a particle of the iron carboxymaltose complex is no greater than about 35 nm; and the iron carboxymaltose complex is administered intravenously infused or intravenously injected at a concentration of about 1000 mg elemental iron in about 200 ml to about 300 ml of diluent. In some of these embodiments, the iron carboxymaltose complex is polynuclear iron (III)-hydroxide 4(R)-(poly-(1→4)-O-α-D-glucopyranosyl)-oxy-2(R),3(R),5(R),6-tetrahydroxy-hexanoate. In some of these embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between about 5 and about 20, and when a mixture of several maltodextrins is applied, the dextrose equivalent lies between about 5 and about 20 and the dextrose equivalent of each individual maltodextrin contained in the mixture lies between about 2 and about 20.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1C are a series of electron micrographs that depict the particle size of three iron carbohydrate complexes. FIG. 1A is an electron micrograph depicting the particle size of Dexferrum® (an iron dextran). FIG. 1B is an electron micrograph depicting the particle size of Venofer® (an iron sucrose). FIG. 1C is an electron micrograph depicting the particle size of polynuclear iron (III)-hydroxide 4(R)-(poly-(1→4)-O-α-D-glucopyranosyl)-oxy-2(R),3(R),5(R),6-tetrahydroxy-hexanoate ("VIT-45", an iron carboxymaltose complex).

DETAILED DESCRIPTION OF THE INVENTION

Figure 2:
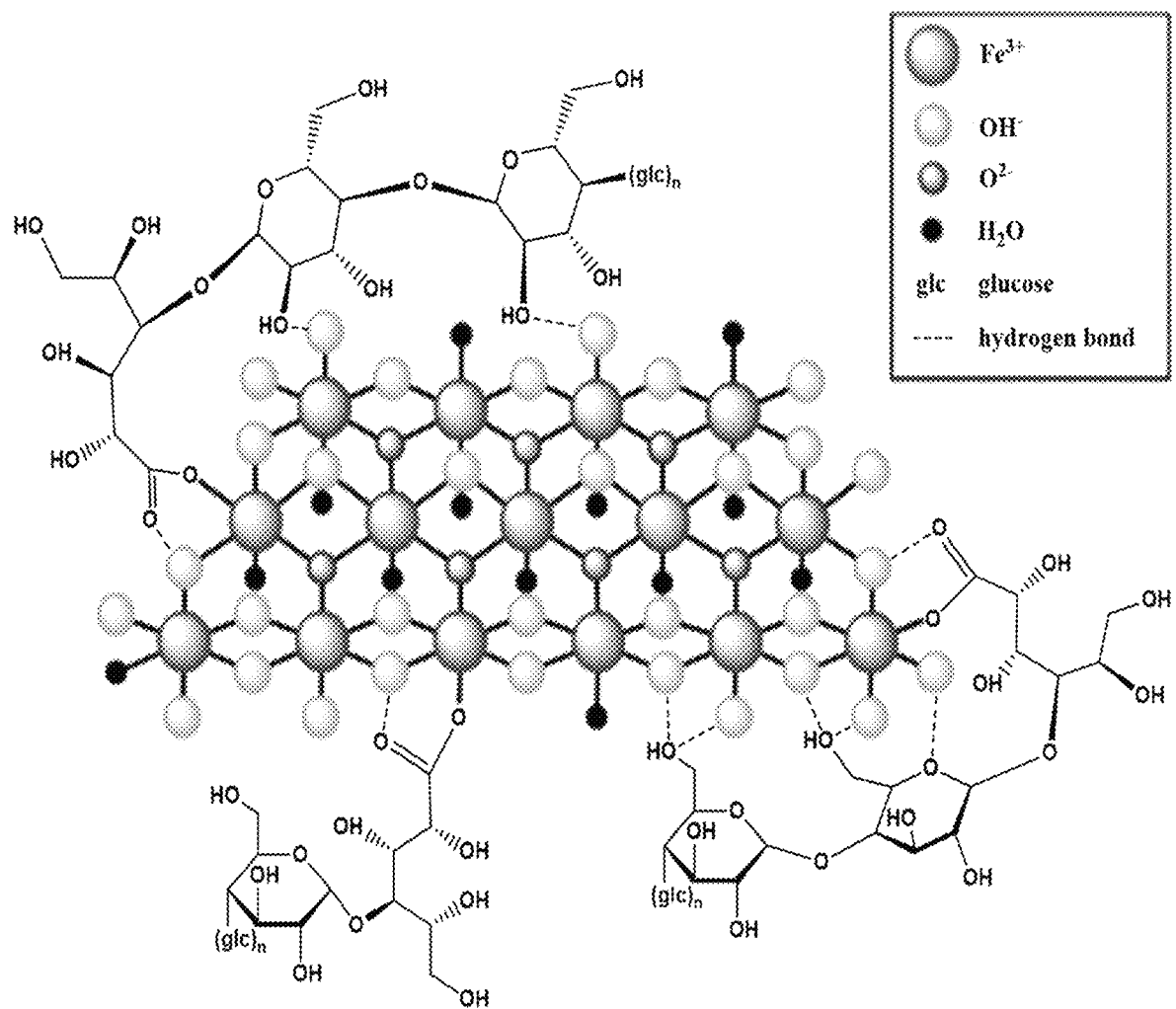
FIG. 2 is a schematic representation of an exemplary iron carboxymaltose complex.

The present invention makes use of iron carbohydrate complexes that can be administered parenterally at relatively high single unit dosages for the therapeutic treatment of a variety of iron-associated diseases, disorders, or conditions. Generally, states indicative of a need for therapy with high single unit dosages of iron carbohydrate complexes include, but are not limited to iron deficiency anemia, anemia of chronic disease, and states characterized by dysfunctional iron metabolism. Efficacious treatment of these, and other, diseases and conditions with parenteral iron formulations (supplied at lower single unit dosages than those described herein) is generally known in the art. See e.g., Van Wyck et al. (2004) *J. Am. Soc. Nephrol.* 15: S91-S92. The present invention is directed to use of iron carbohydrate complexes that can be administered parenterally at relatively high single unit dosages, thereby providing a safe and efficient means for delivery of a total dose of iron in fewer sessions over the course of therapeutic treatment.

Iron deficiency anemia is associated with, for example, chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents.

Anemia of chronic disease is associated with, for example, rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjogren's syndrome; congestive heart failure/cardiomyopathy; and idiopathic geriatric anemia.

Anemia is also associated with, for example, Crohn's Disease; gastric surgery; ingestion of drug products that inhibit iron absorption; and chronic use of calcium.

States characterized by dysfunctional iron metabolism and treatable with the single unit dosages of iron carbohydrate complexes described herein include, but are not limited to, restless leg syndrome; blood donation; Parkinson's disease; hair loss; and attention deficit disorder.

Again, each of the above listed states, diseases, disorders, and conditions, as well as others, can benefit from the treatment methodologies described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms.

The benefit to a subject to be treated is either statistically significant or at least perceptible to the patient or to the physician. Measures of efficacy of iron replacement therapy are generally based on measurement of iron-related parameters in blood. The aim of treatment is usually to return both Hb and iron stores to normal levels. Thus, efficacy of iron replacement therapy can be interpreted in terms of the ability to normalize Hb levels and iron stores. The effectiveness of treatment with one or more single unit doses of iron carbohydrate complex, as described herein, can be demonstrated, for example, by improvements in ferritin and transferrin saturation, and in raising hemoglobin levels in anemic patients. Iron stores can be assessed by interpreting serum ferritin levels. TfS is frequently used, in addition, to diagnose absolute or functional iron deficiencies. In patients with iron deficiency, serum transferrin is elevated and will decrease following successful iron treatment.

Administration

Methods of treatment of various diseases, disorders, or conditions with iron complex compositions comprise the administration of the complex in single unit dosages of at least 0.6 grams of elemental iron to about at least 2.5 grams of elemental iron. Administration of single unit dosages can be, for example, over pre-determined time intervals or in response to the appearance and/or reappearance of symptoms. For example, the iron carbohydrate complex can be re-administered upon recurrence of at least one symptom of the disease or disorder. As another example, the iron carbohydrate complex can be re-administered at some time period after the initial administration (e.g., after 4 days to 12 months).

Any route of delivery of the single unit dose of iron carbohydrate complex is acceptable so long as iron from the iron complex is released such that symptoms are treated. The single unit dose of iron carbohydrate complex can be administered parenterally, for example intravenously or intramuscularly. Intravenous administration can be delivered as a bolus or preferably as an infusion. For example, the single unit dose of iron carbohydrate complex can be intravenously infused at a concentration of about 1000 mg elemental iron in about 200 ml to about 300 ml of diluent, preferably about 215 ml of diluent or about 250 ml of diluent. The iron carbohydrate complex can be intravenously injected as a bolus. For example, the iron carbohydrate complex can be intravenously injected as a bolus at a concentration of about 1000 mg elemental iron in about 200 ml to about 300 ml of diluent, preferably about 215 ml of diluent or about 250 ml of diluent. The iron carbohydrate complex can be intramuscularly infused at a concentration of, for example, about 1000 mg elemental iron in about 200 ml to about 300 ml of diluent, preferably, about 250 ml of diluent or about 215 ml of diluent. If applied as an infusion, the iron carbohydrate complex can be diluted with sterile saline (e.g., polynuclear iron (III)-hydroxide 4(R)-(poly-(1→4)-O-α-D-glucopyranosyl)-oxy-2(R),3(R),5(R),6-tetra-hydroxy-hexanoate ("VIT-45") 0.9% m/V NaCl or 500 mg iron in up to 250 mL NaCl). The iron carbohydrate complex can be intravenously injected as a bolus without dilution. As an example, the iron carbohydrate complex can be intramuscularly injected at a concentration of about 500 mg elemental iron in less than about 10 ml diluent, preferably about 5 ml.

Generally, total iron dosage will depend on the iron deficit of the patient. One skilled in the art can tailor the total iron dose required for a subject while avoiding iron overload, as overdosing with respect to the total required amount of iron has to be avoided, as is the case for all iron preparations.

The total iron dosage can be delivered as a single unit dosage or a series of single unit dosages. An appropriate single unit dosage level will generally be at least 0.6 grams of elemental iron, particularly at least 0.7 grams; at least 0.8 grams; at least 0.9 grams; at least 1.0 grams; at least 1.1 grams; at least 1.2 grams; at least 1.3 grams; at least 1.4 grams; at least 1.5 grams; at least 1.6 grams; at least 1.7 grams; at least 1.8 grams; at least 1.9 grams; at least 2.0 grams; at least 2.1 grams; at least 2.2 grams; at least 2.3 grams; at least 2.4 grams; or at least 2.5 grams. For example, a single unit dosage is at least 1.0 grams of elemental iron. As another example, a single unit dosage is at least 1.5 grams of elemental iron. As a further example, a single unit dosage is at least 2.0 grams of elemental iron. In yet another example, a single unit dosage is at least 2.5 grams of elemental iron.

An appropriate single unit dosage level can also be determined on the basis of patient weight. For example, an appropriate single unit dosage level will generally be at least 9 mg of elemental iron per kg body weight, particularly at least 10.5 mg/kg, at least 12 mg/kg, at least 13.5 mg/kg, at least 15 mg/kg, at least 16.5 mg/kg, at least 18 mg/kg, at least 19.5 mg/kg, at least 21 mg/kg, at least 22.5 mg/kg, at least 24 mg/kg, at least 25.5 mg/kg, at least 27 mg/kg, at least 28.5 mg/kg, at least 30 mg/kg, at least 31.5 mg/kg, at least 33 mg/kg, at least 34.5 mg/kg, at least 36 mg/kg, or at least 37.5 mg/kg.

Preferably, a single unit dosage can be administered in 15 minutes or less. For example, the single unit dosage can be administered in 14 minutes or less, 13 minutes or less, 12 minutes or less, 11 minutes or less, 10 minutes or less, 9 minutes or less, 8 minutes or less, 7 minutes or less, 6 minutes or less, 5 minutes or less, 4 minutes or less, 3 minutes or less, or 2 minutes or less.

Administration of iron can occur as a one-time delivery of a single unit dose or over a course of treatment involving delivery of multiple single unit doses. Multiple single unit doses can be administered, for example, over pre-determined time intervals or in response to the appearance and reappearance of symptoms. The frequency of dosing depends on the disease or disorder being treated, the response of each individual patient, and the administered amount of elemental iron. An appropriate regime of dosing adequate to allow the body to absorb the iron from the bloodstream can be, for example, a course of therapy once every day to once every eighteen months.

Such consecutive single unit dosing can be designed to deliver a relatively high total dosage of iron over a relatively low period of time. For example, a single unit dose (e.g., 1000 mg) can be administered every 24 hours. As illustration, a total dose of 2000, 2500, 3000, 3500, 4000, 4500, or 5000 mg of elemental iron can be delivered via consecutive daily single unit doses of about 600 mg to about 1000 mg of elemental iron. Given that a single unit dose of 1000 mg can be intravenously introduced into a patient in a concentrated form over, for example, two minutes, such administrative protocol provides a practitioner and patient with an effective, efficient, and safe means to deliver elemental iron.

As another example, a single unit dose can be administered every 3-4 days. As a further example, a single unit dose can be administered once per week. Alternatively, the single unit doses of iron complex may be administered ad hoc, that is, as symptoms reappear, as long as safety precautions are regarded as practiced by medical professionals.

It will be understood, however, that the specific dose and frequency of administration for any particular patient may be varied and depends upon a variety of factors, including the activity of the employed iron complex, the metabolic stability and length of action of that complex, the age, body weight, general health, sex, diet, mode and time of administration, rate of excretion, drug combination, the severity and nature of the particular condition, and the host undergoing therapy.

The following provides but a few examples of treatment protocols for various diseases or disorders.

Iron carbohydrate complex can be given as a single unit dose for the treatment of Restless Leg Syndrome. For example, 1000 mg of elemental iron from an iron carboxymaltose (e.g., polynuclear iron (III)-hydroxide 4(R)-(poly-(1→4)-O-α-D-glucopyranosyl)-oxy-2(R),3(R),5(R),6-tetrahydroxy-hexanoate) can be intravenously injected as a single dose (e.g., 1.5-5 mg iron/ml in normal saline) to a subject suffering from Restless Leg Syndrome. A single intravenous treatment can provide relief of symptoms for an extended period of time, approximately two to twelve months, although relief may be granted for shorter or longer periods. See, U.S. Patent Pub. No. 2004/0180849, incorporated herein by reference. If desired, post-infusion changes in central nervous system iron status can be monitored using measurements of cerebral spinal fluid (CSF) ferritin (and other iron-related proteins) and of brain iron stores using MM. Post-infusion changes in Restless Leg Syndrome are assessed using standard subjective (e.g., patient diary, rating scale) and objective (e.g., P50, SIT, Leg Activity Meters) measures of clinical status. If desired, to better evaluate RLS symptom amelioration, CSF and serum iron values, MRI measures of brain iron and full clinical evaluations with sleep and immobilization tests are obtained prior to treatment, approximately two weeks after treatment, and again twelve months later or when symptoms return. Clinical ratings, Leg Activity Meter recordings and serum ferritin are obtained monthly after treatment. CSF ferritin changes can also be used to assess symptom dissipation.

Iron carbohydrate complex can be given as a single unit dose for the treatment of iron deficiency anemia secondary to heavy uterine bleeding. For example, a single unit dose of 1,000 mg of elemental iron from an iron carboxymaltose in about 250 cc normal saline can be intravenously injected into a subject suffering from iron deficiency anemia secondary to heavy uterine bleeding over 15 minutes every week until a calculated iron deficit dose has been administered. The iron deficit dose can be calculated as follows:

If baseline TSAT<20% or Baseline Ferritin <50 ng/ml:
Dose=Baseline weight (kg)×(15-Baseline Hgb [g/dL])×2.4+500 mg
OR
If baseline TSAT>20% and Baseline Ferritin >50 ng/mL:
Dose=Baseline weight (kg)×(15-Baseline Hgb [g/dL])×2.4
(NOTE: Baseline Hgb equals the average of the last two central lab Hgb's)

Iron carbohydrate complex can be given as a single unit dose for the treatment of iron deficiency anemia. A subject diagnosed as suffering from iron deficiency anemia can be, for example, intravenously injected with a dose of 1,000 mg of iron as VIT-45 (or 15 mg/kg for weight<66 kg) in 250 cc of normal saline over 15 minutes. Subjects with iron deficiency anemia secondary to dialysis or non-dialysis dependent-Chronic Kidney Disease (CKD) as per K/DOQI guidelines will generally have Hgb<12 g/dL; TSAT<25%; and Ferritin <300 ng/mL. Subjects with iron deficiency anemia secondary to Inflammatory Bowel Disease will generally have Hgb<12 g/dL; TSAT<25%; and Ferritin <300 ng/mL. Subjects with iron deficiency anemia secondary to other conditions will generally have Hgb<12 g/dL; TSAT<25%; and Ferritin <100 ng/mL.

Subject in Need Thereof

Single unit dosages of intravenous iron described herein can be administered to a subject where there is a clinical need to deliver iron rapidly or in higher doses and/or in subjects with functional iron deficiency such as those on erythropoietin therapy. A determination of the need for treatment with parenteral iron is within the abilities of one skilled in the art. For example, need can be assessed by monitoring a patient's iron status. The diagnosis of iron deficiency can be based on appropriate laboratory tests, for example, haemoglobin (Hb), serum ferritin, serum iron, transferrin saturation (TfS), and hypochromic red cells.

A determination of the need for treatment with high dosages of parenteral iron can be also be determined through diagnosis of a patient as suffering from a disease, disorder, or condition that is associated with iron deficiency or dysfunctional iron metabolism. For example, many chronic renal failure patients receiving erythropoietin will require intravenous iron to maintain target iron levels. As another example, most hemodialysis patients will require repeated intravenous iron administration, due to dialysis-associated blood loss and resulting negative iron balance.

Monitoring frequency can depend upon the disease, disorder, or condition the patient is afflicted with or at risk for. For example, in a patient initiating erythropoietin therapy, iron indices are monitored monthly. As another example, in patients who have achieved target range Hb or are receiving intravenous iron therapy, TSAT and ferritin levels can be monitored every 3 months.

A patient's iron status can be indicative of an absolute or a functional iron deficiency, both of which can be treated with the compositions and methods described herein. An absolute iron deficiency occurs when an insufficient amount of iron is available to meet the body's requirements. The insufficiency may be due to inadequate iron intake, reduced bioavailability of dietary iron, increased utilization of iron, or chronic blood loss. Prolonged iron deficiency can lead to iron deficiency anemia—a microcytic, hypochromic anemia in which there are inadequate iron stores. Absolute iron deficiency is generally indicated where TSAT<20% and Ferritin <100 ng/mL.

Functional iron deficiency can occur where there is a failure to release iron rapidly enough to keep pace with the demands of the bone marrow for erythropoiesis, despite adequate total body iron stores. In these cases, ferritin levels may be normal or high, but the supply of iron to the erythron is limited, as shown by a low transferrin saturation and an increased number of microcytic, hypochromic erythrocytes. Functional iron deficiency can be characterized by the following characteristics: Inadequate hemoglobin response to erythropoietin; Serum ferritin may be normal or high; Transferrin saturation (TSAT) usually <20%; and/or reduced mean corpuscular volume (MCV) or mean corpuscular hemoglobin concentration (MCHC) in severe cases. Functional iron deficiency (i.e., iron stores are thought to be adequate but unavailable for iron delivery) is generally indicated where TSAT<20% and Ferritin >100 ng/mL.

Assessing the need for intravenous iron therapy as described herein can be according to the National Kidney Foundation's Kidney Disease Outcomes Quality Initiative. See, NKF-K/DOQI, Clinical Practice Guidelines for Anemia of Chronic Kidney Disease (2000), *Am. J. Kidney. Dis* (2001) 37(supp 1):5182-5238. The DOQI provides optimal clinical practices for the treatment of anemia in chronic renal failure. The DOQI guidelines specify intravenous iron treatment of kidney disease based on hemoglobin, transferrin saturation (TSAT), and ferritin levels.

Assessment of need for intravenous iron therapy can also be according to a patient's target iron level. For example, the target hemoglobin level of a patient can be selected as 11.0 g/dL to 12.0 g/dL (hematocrit approximately 33% to 36%). To achieve target hemoglobin with optimum erythropoietin doses, sufficient iron, supplied via an iron carbohydrate complex, is provided to maintain TSAT≥20% and ferritin ≥100 ng/mL. In erythropoietin-treated patients, if TSAT levels are below 20%, the likelihood that hemoglobin will rise or erythropoietin doses fall after iron administration is high. Achievement of target hemoglobin levels with optimum erythropoietin doses is associated with providing sufficient iron to maintain TSAT above 20%.

Iron therapy can be given to maintain target hemoglobin while preventing iron deficiency and also preventing iron overload. Adjusting dosage of iron to maintain target levels of hemoglobin, hematocrit, and laboratory parameters of iron storage is within the normal skill in the art. For example, where a patient is anemic or iron deficient, intravenous iron can be administered when a patient has a ferritin <800, a TSAT<50, and/or a Hemoglobin <12. Iron overload can be avoided by withholding iron for TSAT>50% and/or ferritin >800 ng/mL.

Where a patient is not anemic or iron deficient but is in need of iron administration, for example a patient suffering from Restless Leg Syndrome, hemoglobin and TSAT levels are not necessarily relevant, while ferritin >800 can still provide a general cut off point for administration.

Iron Carbohydrate Complex

Iron carbohydrate complexes are commercially available, or have well known syntheses. Examples of iron carbohydrate complexes include iron monosaccharide complexes, iron disaccharide complexes, iron oligosaccharide complexes, and iron polysaccharide complexes, such as: iron carboxymaltose, iron sucrose, iron polyisomaltose, iron polymaltose, iron gluconate, iron sorbitol, iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

Applicants have discovered that certain characteristics of iron carbohydrate complexes make them amenable to administration at dosages far higher than contemplated by current administration protocols. Preferably, iron carbohydrate complexes for use in the methods described herein are those which have one or more of the following characteristics: a nearly neutral pH (e.g., about 5 to about 7); physiological osmolarity; stable carbohydrate component; an iron core size no greater than about 9 nm; mean diameter particle size no greater than about 35 nm, preferably about 25 nm to about 30 nm; slow and competitive delivery of the complexed iron to endogenous iron binding sites; serum half-life of over about 7 hours; low toxicity; non-immunogenic carbohydrate component; no cross reactivity with anti-dextran antibodies; and/or low risk of anaphylactoid/hypersensitivity reactions.

It is within the skill of the art to test various characteristics of iron carbohydrate complexes as so determine amenability to use in the methods described herein. For example, pH and osmolarity are straightforward determinations performed on a sample formulation. Likewise, techniques such as electron micrograph imaging, transmission electron microscopy, and atomic force microscopy provide direct methods to analyze both iron core and particle size. See e.g., FIG. 1; Table 1. The stability of the carbohydrate complex can be assessed through physicochemical properties such as kinetic characteristics, thermodynamic characteristics, and degradation kinetics. See, Geisser et al. (1992) *Arzneimittelforschung* 42(12):1439-1452. Useful techniques to assess physical and electronic properties include absorption spectroscopy, X-ray diffraction analysis, transmission electron microscopy, atomic force microscopy, and elemental analysis. See, Kudasheva et al. (2004) *J. Inorg. Biochem.* 98:1757-1769. Pharmacokinetics can be assessed, for example, by iron tracer experiments. Hypersensitivity reactions can be monitored and assessed as described in, for example, Bailie et al. (2005) *Nephrol. Dial. Transplant* 20(7):1443-1449. Safety, efficacy, and toxicity in human subjects can be assessed, for example, as described in Spinowitz et al. (2005) *Kidney Intl.* 68:1801-1807.

A particularly preferred iron carbohydrate complex will have a pH between 5.0-7.0; physiological osmolarity; an iron core size no greater than 9 nm; mean diameter particle size no greater than 30 nm; serum half-life of over 10 hours; a non-immunogenic carbohydrate component; and no cross reactivity with anti-dextran antibodies. One example of a preferred iron carbohydrate complex for use in the methods described herein is an iron carboxy-maltose complex (e.g., polynuclear iron (III)-hydroxide 4(R)-(poly-(1→4)-O-α-D-glucopyranosyl)-oxy-2(R),3(R),5(R),6-tetrahydroxy-hexanoate, "VIT-45"). Another example of a preferred iron carbohydrate complex for use in the methods described herein is a carboxyalkylated reduced polysaccharide iron oxide complex (e.g., ferumoxytol, described in U.S. Pat. No. 6,599,498).

Preferably, an iron carbohydrate complex, for use in methods disclosed herein, contains about 24% to about 32% elemental iron, more preferably about 28% elemental iron. Preferably, an iron carbohydrate complex, for use in methods disclosed herein, contains about 25% to about 50% carbohydrate (e.g., total glucose). Preferably, an iron carbohydrate complex, for use in methods disclosed herein, is about 90,000 daltons to about 800,000 daltons, more preferably 100,000 daltons to about 350,000 daltons.

Iron Carboxymaltose Complex

One preferred iron carbohydrate complex for use in the methods described herein is an iron carboxymaltose complex. An example of an iron carboxymaltose complex is polynuclear iron (III)-hydroxide 4(R)-(poly-(1→4)-O-α-D-glucopyranosyl)-oxy-2(R),3(R),5(R),6-tetrahydroxy-hexanoate ("VIT-45"). VIT-45 is a Type I polynuclear iron (III) hydroxide carbohydrate complex that can be administered as parenteral iron replacement therapy for the treatment of various anemia-related conditions as well as other iron-metabolism related conditions. VIT-45 can be represented by the chemical formula: $[FeO_x(OH)_y(H_2O)_z]_n[\{(C_6H_{10}O_5)_m (C_6H_{12}O_7)\}_1]_k$, where n is about 103, m is about 8.1 is about 11, and k is about 4. The molecular weight of VIT-45 is about 150,000 Da. An exemplary depiction of VIT-45 is provided in FIG. 2.

The degradation rate and physicochemical characteristics of the iron carbohydrate complex (e.g., VIT-45) make it an efficient means of parenteral iron delivery to the body stores. It is more efficient and less toxic than the lower molecular weight complexes such as iron sorbitol/citrate complex, and does not have the same limitations of high pH and osmolarity that leads to dosage and administration rate limitations in the case of, for example, iron sucrose and iron gluconate.

The iron carboxymaltose complex (e.g., VIT-45) generally does not contain dextran and does not react with dextran antibodies; therefore, the risk of anaphylactoid/hypersensitivity reactions is very low compared to iron dextran. The iron carboxymaltose complex (e.g., VIT-45) has a nearly neutral pH (5.0 to 7.0) and physiological osmolarity, which makes it possible to administer higher single unit doses over shorter time periods than other iron-carbohydrate complexes. The iron carboxymaltose complex (e.g., VIT-45) can mimic physiologically occurring ferritin. The carbohydrate moiety of iron carboxymaltose complex (e.g., VIT-45) is metabolized by the glycolytic pathway. Like iron dextran, the iron carboxymaltose complex (e.g., VIT-45) is more stable than iron gluconate and sucrose. The iron carboxymaltose complex (e.g., VIT-45) produces a slow and competitive delivery of the complexed iron to endogenous iron binding sites resulting in an acute toxicity one-fifth that of iron sucrose. These characteristics of the iron carboxymaltose complex (e.g., VIT-45) allow administration of higher single unit doses over shorter periods of time than, for example, iron gluconate or iron sucrose. Higher single unit doses can result in the need for fewer injections to replete iron stores, and consequently is often better suited for outpatient use.

After intravenous administration, the iron carboxymaltose complex (e.g., VIT-45) is mainly found in the liver, spleen, and bone marrow. Pharmacokinetic studies using positron emission tomography have demonstrated a fast initial elimination of radioactively labeled iron (Fe) $^{52}$Fe/$^{59}$Fe VIT-45 from the blood, with rapid transfer to the bone marrow and rapid deposition in the liver and spleen. See e.g., Beshara et al. (2003) *Br. J. Haematol.* 120(5): 853-859. Eight hours after administration, 5 to 20% of the injected amount was observed to be still in the blood, compared with 2 to 13% for iron sucrose. The projected calculated terminal half-life ($t_{1/2}$) was approximately 16 hours, compared to 3 to 4 days for iron dextran and 6 hours for iron sucrose.

The iron in the iron carboxymaltose complex (e.g., VIT-45) slowly dissociates from the complex and can be efficiently used in the bone marrow for Hgb synthesis. Under VIT-45 administration, red cell utilization, followed for 4 weeks, ranged from 61% to 99%. Despite the relatively higher uptake by the bone marrow, there was no saturation of marrow transport systems. Thus, high red cell utilization of iron carboxymaltose complex occurs in anemic patients. In addition, the reticuloendothelial uptake of this complex reflects the safety of polysaccharide complexes. Non-saturation of transport systems to the bone marrow indicated the presence of a large interstitial transport pool (e.g., transferrin).

Other studies in patients with iron deficiency anemia revealed increases in exposure roughly proportional with VIT-45 dose (maximal total serum iron concentration was approximately 150 μg/mL and 320 μg/mL following 500 mg and 1000 mg doses, respectively). In these studies, VIT-45 demonstrated a monoexponential elimination pattern with a $t_{1/2}$ in the range 7 to 18 hours, with negligible renal elimination.

Single-dose toxicity studies have demonstrated safety and tolerance in rodents and dogs of intravenous doses of an iron carboxymaltose complex (VIT-45) up to 60 times more than the equivalent of an intravenous infusion of 1,000 mg iron once weekly in humans. Pre-clinical studies in dogs and rats administered VIT-45 in cumulative doses up to 117 mg iron/kg body weight over 13 weeks showed no observed adverse effect level in dose-related clinical signs of iron accumulation in the liver, spleen, and kidneys. No treatment-related local tissue irritation was observed in intra-arterial, perivenous, or intravenous tolerance studies in the rabbit. In vitro and in vivo mutagenicity tests provided no evidence that VIT-45 is clastogenic, mutagenic, or causes chromosomal damage or bone marrow cell toxicity. There were no specific responses to VIT-45 in a dextran antigenicity test.

Approximately 1700 subjects have been treated with an iron carboxymaltose complex (VIT-45) in open label clinical trials (see e.g., Example 5). Many of these subjects have received at least one dose of 15 mg/kg (up to a maximum dose of 1,000 mg) of VIT-45 over 15 minutes intravenously. Few adverse events and no serious adverse events or withdrawals due to adverse events related to VIT-45 administration have been reported. No clinically relevant adverse changes in safety laboratories have been seen.

The physicochemical characteristics of the iron carboxymaltose complex (e.g., VIT-45), the pattern of iron deposition, and the results of the above described studies demonstrate that iron carboxymaltose complex can be safely administered at high single unit therapeutic doses as described herein.

Polyglucose Sorbitol Carboxymethyl Ether-Coated Non-Stoichiometric Magnetite

Another preferred iron carbohydrate complex for use in the methods described herein is a polyglucose sorbitol carboxymethyl ether-coated non-stoichiometric magnetite (e.g., "ferumoxytol"). Ferumoxytol is known in the art to be effective for treating anemia (at single unit doses lower than described herein). See e.g., Spinowitz et al. (2005) *Kidney Intl.* 68:1801-1807. Ferumoxytol is a superparamagnetic iron oxide that is coated with a low molecular weight semi-synthetic carbohydrate, polyglucose sorbitol carboxymethyl ether. Ferumoxytol and its synthesis are described in U.S. Pat. No. 6,599,498, incorporated herein by reference. Safety, efficacy, and pharmacokinetics of ferumoxytol are as described, for example, in Landry et al. (2005) *Am. J. Nephrol.* 25:400-410, 408; and Spinowitz et al. (2005) *Kidney Intl.* 68:1801-1807.

The iron oxide of ferumoxytol is a superparamagnetic form of non-stoichiometric magnetite with a crystal size of 6.2 to 7.3 nm. Average colloidal particle size can be about 30 nm, as determined by light scattering. Molecular weight is approximately 750 kD. The osmolarity of ferumoxytol is isotonic at 297 mOsm/kg and the pH is neutral. The blood half-life of ferumoxytol is approximately 10-14 hours. It has been previously reported that ferumoxytol can be given by direct intravenous push over 1-5 minutes in doses up to 1,800 mg elemental iron per minute, with maximal total dose up to 420 mg per injection (Landry et al. (2005) *Am. J. Nephrol.* 25:400-410, 408).

Core and Particle Size

Intravenous iron agents are generally spheroidal iron-carbohydrate nanoparticles. At the core of each particle is an iron-oxyhydroxide gel. The core is surrounded by a shell of carbohydrate that stabilizes the iron-oxyhydroxide, slows the release of bioactive iron, and maintains the resulting particles in colloidal suspension. Iron agents generally share the same core chemistry but differ from each other by the size of the core and the identity and the density of the surrounding carbohydrate. See, Table 1; FIG. 1.

TABLE 1

Core and Particle Size of Iron Carbohydrate Complexes

| | Iron (III) Control Release Test | Size of the Particle (nm) +/− SEM | |
|---|---|---|---|
| | $T_{75}$ (min) | Iron core | Total Particle |
| Dexferrum ® (an iron dextran) | 122.5 | 11.8 ± 4 | 27 ± 6 |
| VIT-45 (an iron carboxymaltose) | 117.8 | 4.4 ± 1.4 | 6.7 ± 2.5 |
| Venofer ® (an iron sucrose) | 10.2 | 2.8 ± 1 | 6.5 ± 4 |

Differences in core size and carbohydrate chemistry can determine pharmacological and biological differences, including clearance rate after injection, iron release rate in vitro, early evidence of iron bioactivity in vivo, and maximum tolerated dose and rate of infusion.

One of the primary determinants of iron bioactivity is the size of the core and the surface area to volume ratio.

Generally, the rate of labile iron release in each agent is inversely related to the size of its iron core (Van Wyck (2004) *J. Am. Soc. Nephrology* 15:S107-5111, S109) Furthermore, in vitro iron donation to transferrin is inversely related to core size. Core size can depend upon the number of iron atoms contained within. For example, the number of iron atoms contained within a 1 nm core is calculated to be 13, while a 10 nm core is calculated to contain 12770 iron atoms. Where agents share the same core chemistry, the rate of iron release per unit surface area is likely similar, differing perhaps by the strength of the carbohydrate ligand-core iron bound. But for the same total amount of core iron, surface area available for iron release increases dramatically as core radius decreases. That is to say, for equal amounts of iron, the smaller the core, the greater the surface area available for iron release. Of course, the explanation for this non-linear trend is the fact that volume is radius cubed. In short, a collection of many small spheres exposes a greater total surface area than does a collection of an equal mass of fewer, larger spheres.

A smaller iron core size of an iron complex administered for the treatment of various diseases, disorders, or conditions allows wider distribution through tissues, a greater rate of labile iron release, and increased in vitro iron donation to transferrin. Furthermore, the iron complex is more evenly distributed and metabolizes faster due to the smaller core size. But if the core size is too small, the iron complex can move into cells unable to metabolize iron. In one embodiment, an iron complex with a mean iron core size of no greater than about 9 nm is administered. In various embodiments, mean iron core size is less than about 9 nm but greater than about 1 nm, about 2 nm, about 3 nm, about 4 nm, about 5 nm, about 6 nm, about 7 nm, or about 8 nm. Mean iron core size can be, for example, between about 1 nm and about 9 nm; between about 3 nm and about 7 nm; or between about 4 nm and about 5 nm.

The molecular weight (i.e., the whole molecular weight of the agent) is considered a primary determinant in the pharmacokinetics, or in other words, how quickly it is cleared from the blood stream. The amount of labile (i.e., biologically available) iron is inversely correlated with the molecular weight of the iron-carbohydrate complex (Van Wyck (2004) *J. Am. Soc. Nephrology* 15:S107-S111). That is to say, the magnitude of labile iron effect is greatest in iron-carbohydrate compounds of lowest molecular weight and least in those of the highest molecular weight. Generally, there is a direct relationship between the molecular weight of the agent and the mean diameter of the entire particle (i.e., the iron core along with the carbohydrate shell). In various embodiments, the mean diameter size of a particle of the iron carbohydrate complex is no greater than about 35 nm. For example, the particle mean size can be no greater than about 30 nm. As another example, the particle mean size can be no greater than about 25 nm. As another example, the particle mean size can be no greater than about 20 nm. As another example, the particle mean size can be no greater than about 15 nm. As a further example, the particle mean size can be no greater than about 10 nm. As another example, the particle mean size can be no greater than about 7 nm.

Absence of Significant Adverse Reaction to the Single Dosage Unit Administration Generally, a safe and effective amount of an iron carbohydrate complex is, for example, that amount that would cause the desired therapeutic effect in a patient while minimizing undesired side effects. The dosage regimen will be determined by skilled clinicians, based on factors such as the exact nature of the condition being treated, the severity of the condition, the age and general physical condition of the patient, and so on. Generally, treatment-emergent adverse events will occur in less than about 5% of treated patients. For example, treatment-emergent adverse events will occur in less than 4% or 3% of treated patients. Preferably, treatment-emergent adverse events will occur in less than about 2% of treated patients.

For example, minimized undesirable side effects can include those related to hypersensitivity reactions, sometimes classified as sudden onset closely related to the time of dosing, including hypotension, bronchospasm, laryngospasm, angioedema or urticaria or several of these together. Hypersensitivity reactions are reported with all current intravenous iron products independent of dose. See generally, Bailie et al. (2005) *Nephrol. Dial. Transplant* 20(7):1443-1449. As another example, minimized undesirable side effects can include those related to labile iron reactions, sometimes classified as nausea, vomiting, cramps, back pain, chest pain, and/or hypotension. Labile iron reactions are more common with iron sucrose, iron gluconate, and iron dextran when doses are large and given fast.

Pharmaceutical Formulations

In many cases, a single unit dose of iron carbohydrate complex may be delivered as a simple composition comprising the iron complex and the buffer in which it is dissolved. However, other products may be added, if desired, for example, to maximize iron delivery, preservation, or to optimize a particular method of delivery.

A "pharmaceutically acceptable carrier" includes any and all solvents, dispersion media, coatings, antibacterial and anti-fungal agents, isotonic and absorption delaying agents, and the like, compatible with pharmaceutical administration (see e.g., Banker, Modern Pharmaceutics, Drugs and the Pharmaceutical Sciences, 4th ed. (2002) ISBN 0824706749; Remington The Science and Practice of Pharmacy, 21st ed. (2005) ISBN 0781746736). Preferred examples of such carriers or diluents include, but are not limited to, water, saline, Finger's solutions and dextrose solution. Supplementary active compounds can also be incorporated into the compositions. For intravenous administration, the iron carbohydrate complex is preferably diluted in normal saline to approximately 2-5 mg/ml. The volume of the pharmaceutical solution is based on the safe volume for the individual patient, as determined by a medical professional.

An iron complex composition of the invention for administration is formulated to be compatible with the intended route of administration, such as intravenous injection. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; buffers such as acetates, citrates or phosphates, and agents for the adjustment of tonicity such as sodium chloride or dextrose. The pH can be adjusted with acids or bases, such as hydrochloric acid or sodium hydroxide. Preparations can be enclosed in ampules, disposable syringes or multiple dose vials made of glass or plastic.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, Cremophor EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating an iron complex in the required amount in an appropriate solvent with a single or combination of ingredients as required, followed by sterilization. Methods of preparation of sterile solids for the preparation of sterile injectable solutions include vacuum drying and freeze-drying to yield a solid containing the iron complex and any other desired ingredient.

Active compounds may be prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

A single unit dose of iron carbohydrate complex may be intravenously administered in a volume of pharmaceutically acceptable carrier of, for example, about 1000 mg of elemental iron in about 200 ml to about 300 ml of diluent. For example, a single unit dose of iron carbohydrate complex may be intravenously administered in a volume of pharmaceutically acceptable carrier of about 1000 mg of elemental iron in about 250 ml of diluent. As another example, a single unit dose of iron carbohydrate complex may be intravenously administered in a volume of pharmaceutically acceptable carrier of about 1000 mg of elemental iron in about 215 ml of diluent.

A preferred pharmaceutical composition for use in the methods described herein contains VIT-45 as the active pharmaceutical ingredient (API) with about 28% weight to weight (m/m) of iron, equivalent to about 53% m/m iron (III)-hydroxide, about 37% m/m of ligand, <6% m/m of NaCl, and <10% m/m of water.

Kits for Pharmaceutical Compositions

Iron complex compositions can be included in a kit, container, pack or dispenser, together with instructions for administration according to the methods described herein. When the invention is supplied as a kit, the different components of the composition may be packaged in separate containers, such as ampules or vials, and admixed immediately before use. Such packaging of the components separately may permit long-term storage without losing the activity of the components. Kits may also include reagents in separate containers that facilitate the execution of a specific test, such as diagnostic tests.

The reagents included in kits can be supplied in containers of any sort such that the life of the different components are preserved and are not adsorbed or altered by the materials of the container. For example, sealed glass ampules or vials may contain lyophilized iron complex or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that, upon removal, permits the components to mix. Removable membranes may be glass, plastic, rubber, etc.

Kits may also be supplied with instructional materials. Instructions may be printed on paper or other substrate, and/or may be supplied on an electronic-readable medium, such as a floppy disc, CD-ROM, DVD-ROM, mini-disc, SACD, Zip disc, videotape, audio tape, etc. Detailed instructions may not be physically associated with the kit; instead, a user may be directed to an internet web site specified by the manufacturer or distributor of the kit, or supplied as electronic mail.

Having described the invention in detail, it will be apparent that modifications, variations, and equivalent embodiments are possible without departing the scope of the invention defined in the appended claims. It should be understood that all references cited are incorporated herein by reference. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1: Non-Toxicity Studies

Nonclinical toxicity of VIT-45 is very low, as is normal for Type I polynuclear iron (III)-hydroxide carbohydrate complexes. The single dose toxicity is so low that the $LD_{50}$ could not be estimated and is higher than 2000 mg iron/kg b.w. Mice tested with a single dose of 250 mg iron/kg b.w., injected within 2 seconds, showed no signs of illness. The highest non-lethal dose level of 1000 mg iron/kg b.w. in mice and rats is also very high in comparison to a single unit dose of, for example, 15 mg iron/kg b.w. once per week in humans. These results provide factors of about 70-fold a human dose, demonstrating a large safety margin for acute toxicity of the product.

Example 2: Pharmokinetic Studies

Pharmacokinetic and red blood cell measurements of $^{52}Fe/^{59}Fe$ labelled VIT-45 following i.v. administration using PET in 6 patients showed a red blood cell utilization from 61 to 99%. The 3 patients with iron deficiency anemia showed a utilization of radiolabelled iron of 91 to 99% after 24 days, compared to 61 to 84% for 3 patients with renal anaemia. The terminal $t_{1/2}$ for VIT-45 was calculated to be approximately 16 hours, compared to about 6 hours for iron sucrose. In two further studies in patients with iron deficiency anemia, pharmacokinetic analyses revealed increases in exposure roughly proportional with VIT-45 dose (Cmax approximately 150 μg/mL and 320 μg/mL following 500 mg and 1000 mg doses, respectively). VIT-45 demonstrated a monoexponential elimination pattern with a $t_{1/2}$ in the range 7 to 18 hours. There was negligible renal elimination.

Example 3: Efficacy Studies

The main pharmacodynamic effects of VIT-45 were transient elevations of serum iron levels, TfS and serum ferritin. These effects were seen in all studies (where measured), following both single doses and repeated doses. The increase in serum ferritin levels illustrated the replenishment of the depleted iron stores, which is a well-identified and desired effect of iron therapy. In addition, transiently elevated TfS indicated that iron binding capacity was almost fully utilized following VIT-45 infusion.

Efficacy of iron replacement therapy is interpreted mainly in terms of the ability to normalize Hb levels and iron stores. In the multiple dose studies, patients demonstrated a slowly-developing, sustained increase in Hb levels during study participation. In one study, 37% and 48% of patients in Cohorts 1 and 2, respectively, had achieved normal Hb levels at the 4-week follow-up visit, and 75% and 73%, respectively, had achieved a >20 g/L increase in Hb on at least 1 occasion.

In another study (patients receiving regular hemodialysis), the majority of patients (61.7%) achieved an increase of Hb of >10 g/L at any point during the study. Serum ferritin and TfS levels showed a more prolonged elevation following repeated VIT-45 infusions, indicating a sustained replenishment of iron stores. However, elevated levels of ferritin and TfS indicating iron overload were avoided. In both of these studies, there was a gradual decrease in transferrin over time, also indicating successful iron replacement.

Example 4: Safety Assessments

Safety assessments were made in 73 patients with iron deficiency anemia (27 single-dose, 46 repeated-dose), and 166 patients with renal anemia (3 single-dose, 163 repeated-dose) who received VIT-45 at individual iron doses of 100 mg up to 1000 mg (cumulative doses of 100 to 2200 mg). These studies showed a safety profile equal to, or exceeding, currently available parenteral iron formulations.

In the single-dose studies, there were few adverse events and no serious adverse events or withdrawals due to adverse events. There were also no related clinically relevant adverse changes in vital signs, 12-lead ECGs or laboratory safety tests.

In the repeated-dose studies, there were no deaths attributed to VIT-45, while 10 patients experienced serious adverse events. All of these cases occurred in patients with renal anemia receiving hemodialysis and were considered not related to the VIT-45 treatment. Very few patients were withdrawn from the studies due to treatment-emergent adverse events, and only 2 withdrawals (due to allergic skin reactions) were considered possibly related to treatment. In each of the repeated-dose studies, no patients experienced clinically significant changes in 12-lead ECGs that were related to treatment. There were no consistent changes in laboratory safety parameters, although there was a low incidence (total 6 patients) of laboratory values reported as treatment-related treatment-emergent adverse events (elevated CRP, AST, ALT and GGT, abnormal liver function tests and elevated WBC).

Although many patients in these 2 studies had serum ferritin above 500 μg/L on at least 1 occasion during the study, very few patients also had TfS values >50%. Generally, the elevations of ferritin and TfS were of short duration. Iron overload was avoided using the dosing schedules defined in the studies.

Example 5: Integrated Safety Studies

The following example demonstrates the safety and effectiveness of parenteral VIT-45 in the treatment of anemia in a variety of patient populations, as determined from several integrated safety studies.

A total of 2429 subjects were treated with VIT-45 or control agents over 10 studies that provide safety data for VIT-45. Of these, 1709 subjects received VIT-45 (1095 in completed multicenter studies, 584 in placebo-controlled, single-dose, crossover studies and 30 in pharmacokinetic studies). The mean total dose of VIT-45 administered among the 1095 subjects in the completed multicenter studies was approximately 1300 mg; however, some subjects received VIT-45 doses as high as 3400 mg. The majority of the subjects treated were able to receive their calculated iron requirement in only 1 or 2 doses.

Table 2 provides a summary of VIT-45 studies described in this example.

Study A was a single-center, single-dose escalation, randomized, double-blind, placebo-controlled pharmacokinetic study. Subjects were male and female, between 18 and 45 years of age, inclusive, with mild iron-deficiency anemia. Treatment was a single IV bolus injection of VIT-45 at 100 mg, 500 mg, 800 mg, or 1000 mg. Examined pharmacokinetic parameters included total serum iron and pharmacodynamic (serum ferritin and transferrin, iron binding capacity, % TSATpost, hemoglobin, reticulocyte, and serum transferrin receptor concentrations) endpoints. Examined safety parameters included adverse events, clinical laboratory evaluations, vital signs, ECG, and physical examinations.

Study B was a single-center, single-dose, open label, uncontrolled pharmacokinetic study. Subjects were between 18 and 75 years of age with iron-deficiency or renal anemia with no other cause of anemia. Inclusion criteria included hemoglobin concentration between 9 and 13 g/dL, no blood transfusions in the previous 3 months, and no history of treatment with intravenous iron in the last 2 weeks. Treatment was a single IV bolus injection of VIT-45 at 100 mg labelled with $^{52}$Fe and $^{59}$Fe. Examined primary pharmacokinetic parameters included the distribution of $^{52}$Fe and incorporation of $^{59}$Fe into red blood cells. Examined safety parameters included adverse events, clinical laboratory evaluations, vital signs, and physical examinations.

Study C was an open-label, multicenter, randomized, multiple-dose, active-controlled postpartum anemia study. Subjects were female, postpartum within 10 days after delivery, with hemoglobin ≤10 g/dL at Baseline based on the average of 2 hemoglobin values drawn 18 hours postpartum. Treatment was once weekly doses of VIT-45 for six weeks. VIT-45 dosage was based on the calculated iron deficit (2500 mg total). Where screening serum transferrin saturation (TSAT) was ≤20% or screening ferritin was 50 ng/mL, dosage=pre-pregnancy weight (kg)×(15-baseline hemoglobin [g/dL])×2.4+500 mg. Where screening TSAT was >20% and screening ferritin was >50 ng/mL, dosage=pre-pregnancy weight (kg)×(15-baseline hemoglobin [g/dL])×2.4. Infusion of VIT-45 was as follows: ≤200 mg, administered as an undiluted intravenous push (IVP) over 1-2 minutes; 300-400 mg, administered in 100 cc normal saline solution (NSS) over 6 minutes; 500-1,000 mg administered in 250 cc NSS over 15 minutes. For primary efficacy, "success" was defined as an increase in hemoglobin of ≥2 g/dL anytime between baseline and end of study or time of intervention, while "failure" was defined as <2 g/dL increase in hemoglobin at all times between baseline and end of study or time of intervention. Examined safety parameters included adverse events, clinical laboratory evaluations, vital signs, and physical examinations.

Study D was a multicenter, open-label, randomized, active-controlled, multiple-dose postpartum anemia study. Subjects were adult women 18 years old with postpartum anemia within 6 days after delivery. Treatment was administered once-weekly for a maximum of 3 infusions. Patients received IV infusions of 16.7 mL/min to deliver a maximum dose of 1000 mg iron per infusion. Patients received VIT-45 infusions once weekly for up to 3 occasions until the calculated cumulative dose was reached. Patients 66 kg received a minimum dose of 200 mg and a maximum dose of 15 mg iron/kg during each infusion. Patients >66 kg received a dose of 1000 mg on the first dosing occasion, and a minimum dose of 200 mg and a maximum dose of 1000 mg at each subsequent dosing. Doses of 200-400 mg were diluted in 100 cc NSS and 500-1000 mg were diluted in 250 cc NSS. Primary efficacy was examined as change from baseline levels of hemoglobin to Week 12. Examined safety parameters included adverse events in the mother and breast-fed infant, adverse events leading to discontinuation of treatment, vital signs, 12-lead electrocardiogram (ECG), physical examinations, and clinical laboratory panels.

Study E was a multicenter, open-label, randomized, active-controlled, multiple-dose hemodialysis-associated anemia study. Subjects were adult male or female subjects between the ages of 18 and 80 years (inclusive) requiring hemodialysis with iron deficiency secondary to chronic renal failure. Dosing started on Day 1, Week 0 for both treatment arms and continued 2 or 3 times weekly until the individual calculated cumulative dose was reached. Patients received 200 mg VIT-45 during their scheduled hemodialysis sessions (2-3 sessions/week) until the calculated cumulative dose was reached. Cumulative total iron requirement was calculated for each patient using the Ganzoni formula. Primary Efficacy was examined as the percentage of patients reaching an increase in hemoglobin 10 g/L at 4 weeks after baseline. Examined safety parameters included adverse events, vital signs, 12-lead ECG, physical examinations, and clinical laboratory evaluations.

Study F was a multicenter, open-label, multiple dose, uncontrolled hemodialysis-associated anemia study. Subjects were male and female patients 18-65 years of age, inclusive, with hemodialysis-associated anemia undergoing maintenance hemodialysis. Treatment duration was a maximum of six weeks. Patients received 200 mg VIT-45 during their scheduled hemodialysis sessions (2-3 sessions/week) until the calculated cumulative dose was reached. Cumulative total iron requirement was calculated for each patient using the Ganzoni formula. Efficacy was examined as correction of iron deficiency and hemoglobin concentration of the patient. Examined safety parameters included adverse events, vital signs, 12-lead ECG, physical examinations, hematology and blood chemistry profiles, and urea reduction ratio.

Study G was a multicenter, multiple-dose open-label, uncontrolled gastrointestinal disorder-associated anemia study. Subjects were males and females between 18 and 60 years of age, inclusive, with moderate stable iron-deficiency anemia secondary to a gastrointestinal disorder and a calculated total iron requirement ≥1000 mg; ≥50% of patients in each cohort were to require ≥1500 mg total iron. Duration of treatment was single doses at weekly intervals for up to 4 weeks (Cohort 1) or 2 weeks (Cohort 2). Administration of VIT-45 was by IV bolus injection of 500 mg (Cohort 1) or 1000 mg (Cohort 2), where total iron requirement for each patient, which determined how many weekly infusions were received, was calculated using the formula of Ganzoni. Examined pharmacokinetic parameters included total serum iron and pharmacodynamic (hemoglobin, ferritin, TSAT) endpoints. Examined safety parameters included adverse events, clinical laboratory evaluations, vital signs, ECG, physical examinations, and elevated serum ferritin (>500 μg/L) AND elevated TSAT (>45%).

Study H was a multicenter, multiple-dose randomized, open-label, active-controlled gastrointestinal disorder-associated anemia study. Subjects were males and females aged 18 to 80 years, inclusive, with iron-deficiency anemia secondary to chronic inflammatory bowel disease (ulcerative colitis or Crohn's disease) and a calculated total iron requirement of at least 1000 mg total iron. Treatment was weekly VIT-45 infusions, with a maximum of 3 infusions permitted in a single treatment cycle. Administration consisted of an infusion on Day 1, with subsequent infusions at weekly intervals up to a maximum of 1000 mg iron per dose. The doses were continued until the patient received the cumulative dose based on their individual requirement for iron. Primary efficacy was examined as change from baseline to Week 12 in hemoglobin. Examined safety parameters included adverse events, vital signs, 12-lead ECG, physical examinations, and clinical laboratory evaluations.

Study I was an open label, multiple-dose, multicenter, randomized, active-control anemia due to heavy uterine bleeding study. Subjects were females at least 18 years of age with iron-deficiency anemia secondary to heavy uterine bleeding. Duration of treatment was six weeks. VIT-45 dosage was based on the calculated iron deficit as follows: where baseline TSAT≤20% or baseline ferritin 50 ng/mL, VIT-45 total dose in mg=baseline weight (kg)×(15-baseline hemoglobin [g/dL])×2.4+500; where baseline TSAT>20% and baseline ferritin >50 ng/mL, VIT-45 total dose in mg=baseline weight (kg)×(15-baseline hemoglobin [g/dL])×2.4. For administration, 200 mg was administered as an undiluted IVP over 1-2 minutes; 300-400 mg was administered in 100 cc NSS over 6 minutes; and 500-1,000 mg was administered in 250 cc NSS over 15 minutes. Primary efficacy was examined as the proportion of subjects achieving success, defined as an increase in hemoglobin of ≥2.0 g/dL anytime between baseline and end of study or time of intervention. Examined safety parameters included adverse events, clinical laboratory evaluations, vital signs, and physical examinations.

Study J was a multicenter, single-dose blinded, randomized, placebo-controlled crossover iron deficiency anemia study. Subjects were male or female, at least 18 years of age, with a hemoglobin≤12 g/dL, TSAT≤25%, and ferritin <300 ng/mL (iron-deficiency anemia due to dialysis or non-dialysis dependent chronic kidney disease or inflammatory bowel disease), or ferritin ≤100 ng/mL (iron-deficiency anemia due to other conditions). Treatment was two single doses seven days apart. Administration of VIT-45 occurred over 15 minutes and was ≤1000 mg (15 mg/kg for weight≤66 kg). For pharmacokinetic variables, total serum iron was assessed using Atomic Absorption methodology. Examined safety parameters included adverse events, clinical laboratory evaluations, vital signs, and physical examinations.

TABLE 2

Summary of Safety Studies of VIT-45

| Study Number | Subjects | Intravenous Dose(s) of VIT-45 | Comparator |
|---|---|---|---|
| | | Pharmacokinetic Studies | |
| A | Total: 32 VIT-45: 24 | Single doses of: 100 mg via bolus injection 500 mg, 800 mg, 1000 mg diluted in 250 mL of NSS administered by IV infusion over 15 minutes | Placebo |
| B | Total: 6 VIT-45: 6 | Single dose of 100 mg labelled with $^{52}$Fe and $^{59}$Fe administered as an IV injection over 10 minutes | None |
| | | Studies in Subjects with Postpartum Anemia | |
| C | Total: 352 VIT-45: 174 | Cumulative total iron requirement was calculated for each patient. Patients received IV infusions to deliver a maximum dose of 1000 mg iron per infusion. Patients received VIT-45 infusions once weekly until the calculated cumulative dose was reached or a maximum of 2500 mg had been administered. Doses ≤200 mg were administered IV push over 1-2 minutes; doses of 300-400 mg were diluted in 100 cc NSS and administered over 6 minutes; doses of 500-1000 mg were diluted in 250 cc NSS and administered over 15 minutes. | Oral iron (ferrous sulfate) 325 mg TID for 6 weeks |
| D | Total: 344 VIT-45: 227 | Cumulative total iron requirement was calculated for each patient using the Ganzoni formula. | Oral iron (ferrous sulfate) 100 mg BID for 12 weeks |
| | | Studies in Subjects Undergoing Hemodialysis | |
| E | Total: 237 VIT-45: 119 | Patients received 200 mg IV bolus injection of study drug during their scheduled hemodialysis sessions (2-3 sessions/week) until the calculated cumulative dose was reached. Cumulative total iron requirement was calculated for each patient using the Ganzoni formula, | Venofer ®; patients received 200 mg IV injection over 10 minutes of study drug during their scheduled hemodialysis sessions (2-3 sessions/week) until the calculated cumulative dose was reached. Cumulative total iron requirement was calculated for each patient using the Ganzoni formula.[a] |
| F | Total: 163 VIT-45: 162 | Patients received 200 mg IV push of study drug during their scheduled hemodialysis sessions (2-3 sessions/week) until the calculated cumulative dose was reached. Cumulative total iron requirement was calculated for each patient using the Ganzoni formula. | None |
| | | Studies in Subjects with Gastrointestinal Disorders | |
| G | Total: 46 VIT-45: 46 | 500 mg or 1000 mg iron by IV infusion at weekly intervals for up to 4 weeks (500 mg) or 2 weeks (1000 mg); maximum total dose of 2000 mg. The last dose could have been less, depending on the calculated total iron requirement. Doses were diluted in 250 cc NSS and administered by IV infusion over 15 minutes. | None |
| H | Total: 200 VIT-45: 137 | Cumulative total iron requirement was calculated for each patient using the Ganzoni formula. | Oral iron (ferrous sulfate) 100 mg BID for 12 weeks |
| | | Study in Subjects with Heavy Uterine Bleeding | |
| I | Total: 456 VIT-45: 230 | ≤1000 mg/week (15 mg/kg for weight ≤66 kg); patients received VIT-45 infusions once weekly until the calculated cumulative dose was reached or a maximum of 2500 mg had been administered. Doses ≤200 mg were administered IV push over 1-2 minutes; doses of 300-400 mg were diluted in 100 cc NSS and administered over 6 minutes; doses | Oral iron (ferrous sulfate) 325 mg TID for 6 weeks |

TABLE 2-continued

Summary of Safety Studies of VIT-45

| Study Number | Subjects | Intravenous Dose(s) of VIT-45 | Comparator |
|---|---|---|---|
| | | of 500-1000 mg were diluted in 250 cc NSS and administered over 15 minutes. Study in Subjects with Iron Deficiency Anemia | |
| J | Total: 594 VIT-45: 584 | Single dose of ≤1000 mg by IV infusion over 15 minutes (15 mg/kg for weight ≤66 kg). Doses ≤500 mg were diluted in 100 cc NSS and doses of >500-1000 mg were diluted in 250 cc NSS. Pharmacokinetic subjects: single 1,000 mg dose by IV infusion | Placebo |

The majority of the subjects who received VIT-45 completed the study. The incidence of premature discontinuations in the completed multicenter studies was 10% in the VIT-45 group which is comparable to that observed in the oral iron (9.6%) and Venofer® (13.6%) groups. Reasons for premature discontinuation were generally comparable among the treatment groups, except that the incidence of adverse events leading to discontinuation were higher in the Venofer® group (5.9%) compared to the VIT-45 (1.8%) and oral iron (2.1%) groups, demonstrating the overall tolerability of VIT-45.

The overall incidences of treatment-emergent adverse events were comparable between the VIT-45 (49.5%) and oral iron (51.2%) groups in the completed multicenter studies; the incidence in the Venofer® group was lower (39.0%); however, the number of subjects in the VIT-45 group is almost 10-fold that of the Venofer® group. Treatment-emergent adverse events experienced by ≥2% of the 1095 VIT-45 subjects included headache (8.6%), abdominal pain (2.5%), nausea (2.4%), blood phosphate decreased (2.4%), hypertension (2.2%), nasopharyngitis (2.0%), and hypotension (2.0%). As expected, the most notable difference between subjects treated with VIT-45 and those treated with oral iron was for the incidence of gastrointestinal events (31.0% vs. 12.8%), specifically the incidences of constipation, diarrhea, nausea, and vomiting, which were more than double that observed in the VIT-45 group.

In the calculated dose/first-dose 1,000 mg studies, no statistically significant difference was observed between the VIT-45 (49.5%) and oral iron (51.2%) groups for the overall incidence of treatment-emergent adverse events. The incidence of gastrointestinal disorders was statistically significantly ($p<0.0001$) higher in the oral iron group (31.0%) compared to the VIT-45 group (15.2%), while the incidences of adverse events associated with investigations and skin and subcutaneous tissue disorders were statistically significantly higher in the VIT-45 group (9.1% and 7.3%, respectively) compared to the oral iron group (3.9% and 2.4%, respectively). Among the gastrointestinal disorders, greater proportions of subjects in the oral iron group than the VIT-45 group experienced constipation, nausea, diarrhea, and vomiting, while a greater proportion of VIT-45 subjects experienced abdominal pain than oral iron subjects. Among the adverse events associated with investigations, greater proportions of VIT-45 subjects experienced blood phosphate decreased and GGT increased than oral iron subjects. Among the adverse events associated with skin and subcutaneous tissue disorders, greater proportions of VIT-45 subjects experienced rash and pruritus than oral iron subjects.

The only drug-related treatment-emergent adverse events reported by at least 2% of VIT-45 subjects in the calculated dose/first-dose 1,000 mg studies were headache (3.9%) and blood phosphate decreased (3.3%). The incidence of treatment-emergent adverse events reported on the first day of dosing in the calculated dose/first-dose 1,000 mg studies was statistically significant higher in the VIT-45 group compared to the oral iron group (6.8% vs. 2.7%). On the first day of dosing, the VIT-45 group had statistically significantly greater proportions of subjects who experienced general disorders and administration site conditions, primarily events associated with the site of study drug infusion, and skin and subcutaneous tissue disorders, primarily rash and urticaria, compared to the oral iron group.

The overall incidence of treatment-emergent adverse events was similar among VIT-45 subjects treated with either the 200 mg or 1000 mg doses. The only notable difference was for the higher incidence of headache in the 1000-mg group, which was almost double that observed for the 200-mg group. No meaningful trends were apparent with respect to the incidence of treatment-emergent adverse events when analyzed by gender, age, race, weight, or etiology of anemia.

There were no deaths in the study attributed to VIT-45. The incidence of other serious adverse events among VIT-45 subjects was low (3% in all completed multicenter studies and 0.3% in the placebo-controlled, single-dose crossover study) and none were considered related to study drug. The incidence of premature discontinuation due to adverse events was comparable between the VIT-45 group (2.1%) and the other active treatment groups (3.1% oral iron and 2.5% Venofer®). The incidence of drug-related treatment-emergent adverse events of hypersensitivity was 0.2%, the same as that observed with oral iron (0.2%). Drug-related mild or moderate hypotension was observed in 4 (0.2%) VIT-45 subjects, none of which were considered serious, led to premature discontinuation, or were symptomatic. Treatment-emergent adverse events indicative of potential allergic reactions including rash, pruritus, and urticaria were reported by <2% of subjects who were treated with VIT-45; none of these events was considered serious and few led to premature discontinuation.

Laboratory evaluations of mean changes from baseline and potentially clinically significant values demonstrated no clinically meaningful changes for the majority of the parameters evaluated. However, during the conduct of the latter portion of the clinical program, transient, asymptomatic decreases in blood phosphate levels were observed among subjects treated with VIT-45. The decreases were apparent approximately 7 days after the initial dose of VIT-45 and the median time to recovery was approximately 2 weeks. No subjects reported an adverse event that was related to serum phosphate and no subject discontinued from the study due to decreased serum phosphate. The only predictor of change in serum phosphate was that subjects with higher baseline serum phosphate values had larger decreases in serum phosphate. The fact that the majority of oral iron-treated subjects also had a post-baseline decrease in phosphate and the negative correlation of baseline serum phosphate with changes in serum phosphate for both the VIT-45 and oral iron treatment groups suggest that the mechanism is intrinsic to iron therapy in this severely anemic population.

Overall, no clinically meaningful changes in vital signs evaluations were associated with VIT-45 administration.

Safety data from more than 1700 subjects demonstrate the safety and tolerability of VIT-45.

What is claimed:

1. A method of treating a disease, disorder, or condition characterized by iron deficiency or dysfunctional iron metabolism resulting in reduced bioavailability of dietary iron, comprising administering to a human subject in need thereof an iron carbohydrate complex in a single dosage of at least 9 mg of elemental iron per kg of body weight, wherein:
   a) the disease, disorder or condition is an anemia selected from among:
      iron deficiency anemia;
      anemia of chronic disease; and
      an anemia due to impaired iron absorption or poor nutrition;
   b) the iron carbohydrate complex is substantially non-immunogenic, and has substantially no cross reactivity with anti-dextran antibodies;
   c) the iron carbohydrate complex is an iron polyisomaltose complex or an iron polyglucose sorbitol carboxymethyl ether complex; and
   d) the disease, disorder or condition is not Restless Leg Syndrome.

2. The method of claim 1, wherein the iron carbohydrate complex is an iron polyisomaltose complex.

3. The method of claim 2, wherein the polyisomaltose is reduced polyisomaltose.

4. The method of claim 1, wherein the iron carbohydrate complex is an iron polyglucose sorbitol carboxymethyl ether complex.

5. The method of claim 4, wherein the iron carbohydrate complex is a polyglucose sorbitol carboxymethyl ether-coated non-stoichiometric magnetite complex.

6. The method of claim 5, wherein the iron carbohydrate complex has a crystal size of 6.2 to 7.3 nm.

7. The method of claim 5, wherein the iron carbohydrate complex has an average colloidal particle size of about 30 nm.

8. The method of claim 5, wherein the iron carbohydrate complex has a molecular weight of approximately 750 kD.

9. The method of claim 4, wherein the iron carbohydrate complex has a crystal size of 6.2 to 7.3 nm.

10. The method of claim 4, wherein the iron carbohydrate complex has an average colloidal particle size of about 30 nm.

11. The method of claim 4, wherein the iron carbohydrate complex has a molecular weight of approximately 750 kD.

12. The method of claim 4, wherein the iron carbohydrate complex has a blood half-life of approximately 10-14 hours.

13. The method of claim 4, wherein the iron carbohydrate complex has neutral pH and isotonic osmolarity.

14. The method of claim 4, wherein the iron carbohydrate complex is administered in about 15 minutes or less.

15. The method of claim 4, wherein the single dose of the iron carbohydrate complex is at least about 0.6 grams of elemental iron.

16. The method of claim 4, wherein administration of the single dose is repeated.

17. The method of claim 4, further comprising a second administration of said iron carbohydrate complex upon recurrence of at least one symptom of the disease, disorder, or condition.

18. The method of claim 17, wherein the second administration is 3-4 days after the first administration.

19. The method of claim 17, wherein the second administration is one week after the first administration.

20. The method of claim 1, wherein the iron carbohydrate complex is administered in about 15 minutes or less.

21. The method of claim 1, wherein the single dose of the iron carbohydrate complex is at least about 0.6 grams of elemental iron.

22. The method of claim 1, wherein the iron carbohydrate complex is administered parenterally.

23. The method of claim 21, wherein the single dosage unit of elemental iron is about 1000 mg.

24. The method of claim 1, wherein the anemia comprises iron deficiency anemia.

25. The method of claim 1, wherein the anemia comprises an iron deficiency anemia associated with chronic blood loss, acute blood loss, pregnancy, childbirth, childhood development, psychomotor and cognitive development in children, breath holding spells, heavy uterine bleeding, menstruation, chronic recurrent hemoptysis, idiopathic pulmonary siderosis, chronic internal bleeding, gastrointestinal bleeding, parasitic infections, chronic kidney disease, dialysis, surgery or acute trauma, chronic ingestion of alcohol, chronic ingestion of salicylates, chronic ingestion of steroids, chronic ingestion of non-steroidal anti-inflammatory agents, or chronic ingestion of erythropoiesis stimulating agents.

26. The method of claim 1, wherein the anemia is of a chronic disease selected from among rheumatoid arthritis, cancer, Hodgkin's leukemia, non-Hodgkin's leukemia, cancer chemotherapy, inflammatory bowel disease, ulcerative colitis, thyroiditis, hepatitis, systemic lupus erythematosus, polymyalgia rheumatica, scleroderma, mixed connective tissue disease, Sjogren's syndrome, congestive heart failure/cardiomyopathy, and idiopathic geriatric anemia.

27. The method of claim 1, wherein the anemia is due to impaired iron absorption or poor nutrition.

28. The method of claim 1, wherein the anemia is associated with Crohn's Disease, gastric surgery, ingestion of drug products that inhibit iron absorption, or chronic use of calcium.

29. The method of claim 1, wherein the iron carbohydrate complex is administered intravenously.

30. The method of claim 25, wherein the single dosage unit of elemental iron is about 1000 mg.

* * * * *